US011718648B2

(12) United States Patent
Møller et al.

(10) Patent No.: US 11,718,648 B2
(45) Date of Patent: Aug. 8, 2023

(54) **VACCINES TARGETING *PSEUDOMONAS AERUGINOSA***

(71) Applicant: Evaxion Biotech A/S, Hørsholm (DK)

(72) Inventors: Niels Iversen Møller, Hørsholm (DK); Andreas Holm Mattsson, Hørsholm (DK)

(73) Assignee: Evaxion Biotech A/S, Hørsholm (DK)

( * ) Notice: Subject to any disclaimer, the term of this patent is extended or adjusted under 35 U.S.C. 154(b) by 0 days.

(21) Appl. No.: 16/473,443

(22) PCT Filed: Jan. 5, 2018

(86) PCT No.: PCT/EP2018/050226

§ 371 (c)(1),
(2) Date: Jun. 25, 2019

(87) PCT Pub. No.: WO2018/127545

PCT Pub. Date: Jul. 12, 2018

(65) Prior Publication Data

US 2019/0330281 A1 Oct. 31, 2019

(30) Foreign Application Priority Data

Jan. 5, 2017 (EP) .................................... 17150419

(51) Int. Cl.

| | |
|---|---|
| ***C07K 14/21*** | (2006.01) |
| ***A61P 31/04*** | (2006.01) |
| ***A61K 39/104*** | (2006.01) |
| ***C07K 14/33*** | (2006.01) |
| ***C07K 14/34*** | (2006.01) |
| ***C07K 14/435*** | (2006.01) |
| ***C07K 16/12*** | (2006.01) |
| ***C12Q 1/689*** | (2018.01) |
| ***G01N 33/569*** | (2006.01) |
| ***A61K 39/00*** | (2006.01) |

(52) U.S. Cl.

CPC ............ *C07K 14/21* (2013.01); *A61K 39/104* (2013.01); *A61P 31/04* (2018.01); *C07K 14/33* (2013.01); *C07K 14/34* (2013.01); *C07K 14/43504* (2013.01); *C07K 16/1214* (2013.01); *C12Q 1/689* (2013.01); *G01N 33/56911* (2013.01); *A61K 2039/505* (2013.01); *A61K 2039/55505* (2013.01); *A61K 2039/6037* (2013.01); *A61K 2039/6081* (2013.01); *A61K 2039/627* (2013.01)

(58) Field of Classification Search

CPC ................................ C07K 14/21; A61P 31/04
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,684,611 | A | 8/1987 | Schilperoot et al. |
| 4,800,159 | A | 1/1989 | Mullis et al. |
| 4,879,236 | A | 11/1989 | Smith et al. |
| 4,952,500 | A | 8/1990 | Finnerty et al. |
| 5,302,523 | A | 4/1994 | Coffee et al. |
| 5,322,783 | A | 6/1994 | Tomes et al. |
| 5,384,253 | A | 1/1995 | Krzyzek et al. |
| 5,464,765 | A | 11/1995 | Coffee et al. |
| 5,538,877 | A | 7/1996 | Lundquist et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,656,610 | A | 8/1997 | Shuler et al. |
| 5,702,932 | A | 12/1997 | Hoy et al. |
| 5,736,524 | A | 4/1998 | Content et al. |
| 5,780,448 | A | 7/1998 | Davis |
| 5,789,215 | A | 8/1998 | Berns et al. |
| 5,843,650 | A | 12/1998 | Segev |
| 5,846,709 | A | 12/1998 | Segev |
| 5,846,783 | A | 12/1998 | Wu et al. |
| 5,849,497 | A | 12/1998 | Steinman |
| 5,849,546 | A | 12/1998 | Sousa et al. |
| 5,849,547 | A | 12/1998 | Cleuziat et al. |
| 5,858,652 | A | 1/1999 | Laffler et al. |
| 5,866,366 | A | 2/1999 | Kallender |
| 5,871,986 | A | 2/1999 | Boyce |
| 5,916,776 | A | 6/1999 | Kumar |
| 5,922,574 | A | 7/1999 | Minter |

(Continued)

FOREIGN PATENT DOCUMENTS

| | | |
|---|---|---|
| EP | 0297291 | 1/1989 |
| EP | 0357024 | 3/1990 |

(Continued)

OTHER PUBLICATIONS

Skolnick et al., Trends in Biotechnology, 2000; 18: 34-39 (Year: 2000).*

Ellis, Vaccines, W.B. Saunders Company, 1988; Chapter 29, pp. 568-574 (Year: 1988).*

Boslego et al (Vaccines and Immunotherapy, 1991, Chapter 17 (Year: 1991).*

(Continued)

*Primary Examiner* — Brian Gangle

*Assistant Examiner* — Lakia J Jackson-Tongue

(74) *Attorney, Agent, or Firm* — McHale & Slavin, P.A.

(57) ABSTRACT

Disclosed are immunogenic proteins from *Pseudomonas aeruginosa* as well as nucleic acids, vectors and transformed cells useful for expression of the proteins. Also disclosed are methods for prophylaxis of infection with *Pseudomonas aeruginosa* using the proteins, nucleic acids, vectors or transformed cells.

9 Claims, 9 Drawing Sheets

Figure 2:
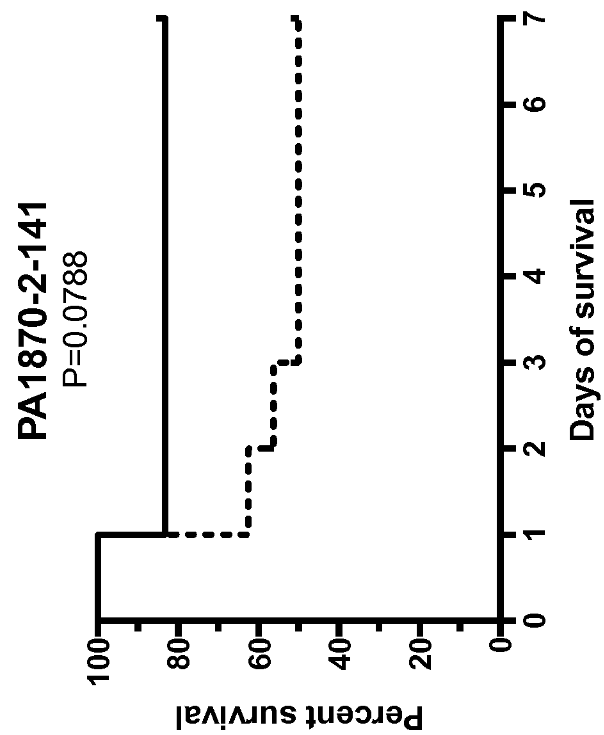

Specification includes a Sequence Listing.

(56) References Cited

U.S. PATENT DOCUMENTS

| | | | | |
|---|---|---|---|---|
| 5,928,905 | A | 7/1999 | Stemmer et al. | |
| 5,928,906 | A | 7/1999 | Koster et al. | |
| 5,932,451 | A | 8/1999 | Wang et al. | |
| 5,935,825 | A | 8/1999 | Nishimura et al. | |
| 5,939,291 | A | 8/1999 | Loewy et al. | |
| 5,942,391 | A | 8/1999 | Zhang et al. | |
| 5,945,100 | A | 8/1999 | Fick | |
| 5,981,274 | A | 11/1999 | Tyrrell et al. | |
| 5,994,624 | A | 11/1999 | Trolinder et al. | |
| 6,551,795 | B1 * | 4/2003 | Rubenfield | C07K 14/21 435/253.3 |
| 2004/0029129 | A1 * | 2/2004 | Wang | C07K 14/30 435/6.18 |
| 2007/0020624 | A1 * | 1/2007 | Rubenfield | C07K 14/21 435/6.15 |

FOREIGN PATENT DOCUMENTS

| | | |
|---|---|---|
| EP | 2192172 | 6/2010 |
| EP | 1769068 | 12/2014 |
| EP | 2853599 | 4/2015 |
| GB | 2202328 | 9/1988 |
| WO | WO9014837 | 12/1990 |
| WO | WO9409699 | 5/1994 |
| WO | WO9506128 | 3/1995 |
| WO | WO9820734 | 5/1998 |
| WO | WO 2002/077183 A9 * | 10/2002 |
| WO | WO2005081905 | 9/2005 |
| WO | WO2011125015 | 10/2011 |
| WO | WO2015189422 | 12/2015 |
| WO | WO2017005670 | 1/2017 |
| WO | WO2018127545 | 7/2018 |

OTHER PUBLICATIONS

Colman Res. Immunology, Jan. 1994; 145: 33-36 (Year: 1994).*

Gupta et al., Pharmaceutical Biotechnology, 1995; 6: 229-248 (Year: 1995).*

Brady et al., Carrier Protein Outsourcing—BioProcess InternationalBioProcess International, Nov. 1, 2012 (Year: 2012).*

Stover et al., Nature, 2000; 406:959-964 (Year: 2000).*

Campbell, A., Laboratory Techniques in Biochemistry And Molecular Biology, vol. 13, Chapter 1, pp. 1-33, 1984 (Year: 1984).*

Harris et al., Micron, 1999; 30: 597-623 (Year: 1999).*

Nishat et al., Vaccines 2016, 4;19:2-16 (Year: 2016).*

Petersen, B. et al, "A generic method for assignment of reliability scores applied to solvent accessibility predictions", BMC Structural Biology, vol. 9:51, pp. 1-10, (Jul. 2009).

Larsen, J. et al, "Improved method for predicting linear B-cell epitopes", Internet article: http.//www.Immunome-Research.com/content/2/1/2, BioMed Central, vol. 2:2, pp. 1-7, (Apr. 2006).

Petersen, B. et al, "NetTurnP-neural network prediction of Beta-turns by use of evolutionary information and predicted protein sequence features", PlosOne, vol. 5:11:e15079, pp. 1-9, (Nov. 2010).

Kohler, G. et al, "Continuous cultures of fused cells secreting antibody of predefined specificity", Nature, vol. 256, pp. 495-497, (1975).

Robinson, H. et al, "DNA vaccines", Seminars in Immunology, vol. 9:5, pp. 271-283, (Nov. 1997).

Donnelly, J. et al, "DNA Vaccines" Annual eview of Immunology, vol. 15, pp. 617-648, (Apr. 1997).

Anonymous, "CAS:2006_1231400_935964117_1", retrieved from Internet URL:http://ibis.internal.epo.org/exam/dbfetch.jsp?id=CAS:2006_1231400_935964117_1, (May 2007).

Lee, D. et al, "Genomic analysis reveals that pseudomonas aeruginosa virulence is combinatorial", Genome Biology, Biomed Central, Ltd., vol. 7(10), p. R90, XP021027293, (Oct. 2006).

* cited by examiner

VACCINES TARGETING *PSEUDOMONAS AERUGINOSA*

FIELD OF THE INVENTION

The present invention relates to the field of antimicrobial prophylaxis and therapy. In particular the present invention relates to novel proteins and polynucleotides derived from *Pseudomonas aeruginosa*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

*Pseudomonas aeruginosa* is an opportunistic gram-negative pathogen. It represents a major course of hospital-acquired infections, especially in burnt and other immunocompromised patients, including transplant or cancer patients. Therefore, it is regarded as a "problem microbe" in human medicine.

Many efforts have been made so far in order to develop a vaccine against *Pseudomonas aeruginosa*. For example, in the EP-0 297 291 the complete amino acid-sequence of the outer membrane protein F, as well as the nucleotide sequence coding for OprF is disclosed. In the EP-0 357 024 the complete amino acid sequence of the outer membrane protein I and, additionally, the nucleotide sequence coding for OprI is shown. Furthermore, with both proteins it was shown that they may be useful for conferring immunoprotection against *Pseudomonas aeruginosa* to an animal or human proband. However, improvement of procedures of vaccination against and treatment of a lethal *Pseudomonas aeruginosa* infection is still an object.

Vaccination is considered to be a very effective method of preventing infectious diseases in human and veterinary health care. Vaccination is the administration of immungenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

Applicant's international patent application publication WO 2017/005670 (PCT/EP2016/065647) discloses 30 protein vaccine antigens as well as fragments and variants derived from *P. aeruginosa*. This patent application also discloses immunogens/vaccines derived from these and the nucleic acids that encode the 30 protein vaccine antigens and their fragments and variants.

OBJECT OF THE INVENTION

It is an object of embodiments of the invention to provide *Pseudomonas aeruginosa* derived antigenic polypeptides that may serve as constituents in vaccines against *Pseudomonas aeruginosa* infections and in diagnosis of *Pseudomonas aeruginosa* infections. It is also an object to provide nucleic acids, vectors, transformed cells, vaccine compositions, and other useful means for molecular cloning as well as for therapy and diagnosis with relevance for *Pseudomonas aeruginosa*.

SUMMARY OF THE INVENTION

It has been found by the present inventor(s) that *Pseudomonas aeruginosa* expresses a number of hitherto unknown putatively surface exposed proteins which are candidates as vaccine targets as well as candidates as immunizing agents for preparation of antibodies that target *Pseudomonas aeruginosa*.

So, in a first aspect the present invention relates to a polypeptide comprising a) an amino acid sequence selected from the group consisting of any one of SEQ ID NOs: 1-14, or b) an amino acid sequence consisting of at least 5 contiguous amino acid residues from any one of SEQ ID NOs: 1-14, or c) an amino acid sequence having a sequence identity of at least 60% with the amino acid sequence of a), d) an amino acid sequence having a sequence identity of at least 60% with the amino acid sequence of b), or e) an assembly of amino acids derived from any one of SEQ ID NOs: 1-14 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or ii) a nucleotide sequence consisting of any one of SEQ ID NOs: 31-90.

iii) a nucleotide sequence consisting of at least 10 consecutive nucleotides in any one of SEQ ID NOs: 31-90, iv) a nucleotide sequence having a sequence identity of at least 60% with the nucleotide sequence in i) or ii), v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *Pseudomonas aeruginosa* in the animal.

In a seventh and eighth aspect, the invention relatas to 1) a polyclonal antibody in which the antibodies specifically bind to at least one polypeptide of the invention, and which is essentially free from antibodies binding specifically to other *Pseudomonas aeruginosa* polypeptides, and to 2) an isolated monoclonal antibody or antibody analogue which binds specifically to a polypeptide of the invention. In a related ninth aspect, the invention relates to a pharmaceutical composition comprising such a polyclonal or monoclona antibody and a pharmaceutically acceptable carrier, vehicle or diluent.

In a $10^{th}$ aspect, the invention relates to a method for prophylaxis, treatment or amelioration of infection with *Pseudomonas aeruginosa*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *Pseudomonas aeruginosa*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *Pseudomonas aeruginosa* in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *Pseudomonas aeruginosa*, in particular the presence of a nucleic acid characteristic of *Pseudomonas aeruginosa*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising
culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or
preparing said polypeptide by means of solid or liquid phase peptide synthesis.

In a $15^{th}$ aspect, the invention relates to a method for determining whether a substance, such as an antibody, is potentially useful for treating infection with *Pseudomonas aeruginosa*, the method comprising contacting the polypeptide of the invention with the substance and subsequently establishing whether the substance has at least one of the following characteristics:

1) the ability to bind specifically to said polypeptide,
2) the ability to competed with said polypeptide for specific binding to a ligand/receptor, and
3) the ability to specifically inactivate said polypeptide.

Finally, in a $16^{th}$ aspect, the invention relates to a method for determining whether a substance, such as a nucleic acid, is potentially useful for treating infection with *Pseudomonas aeruginosa*, the method comprising contacting the substance with the nucleic acid fragment of claim of the invention and subsequently establishing whether the substance has either the ability to 1) bind specifically to the nucleic acid fragment, or
2) bind specifically to a nucleic acid that hybridizes specifically with the nucleic acid fragment.

LEGENDS TO THE FIGURES

Figure 1:
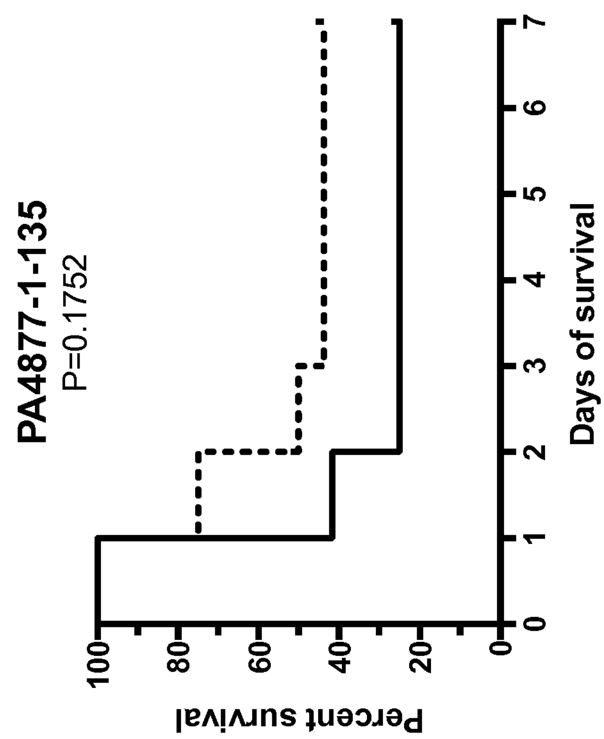
Figure 3:
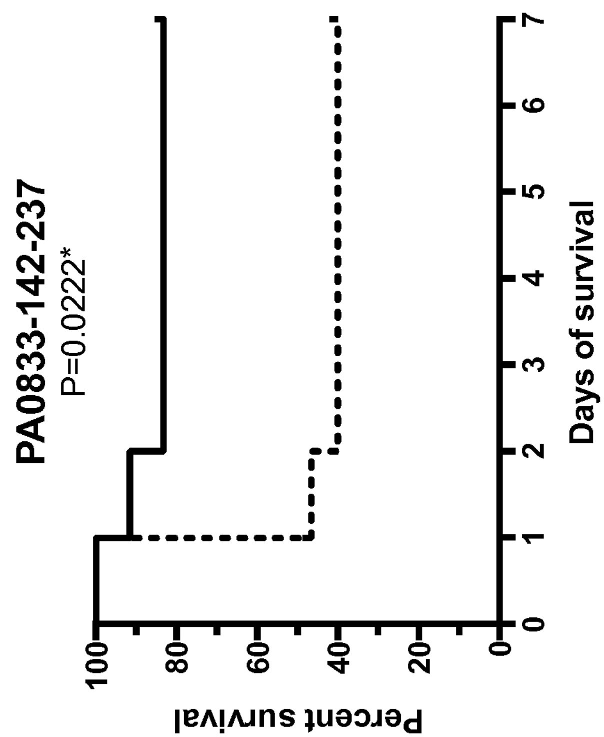
Figure 4:
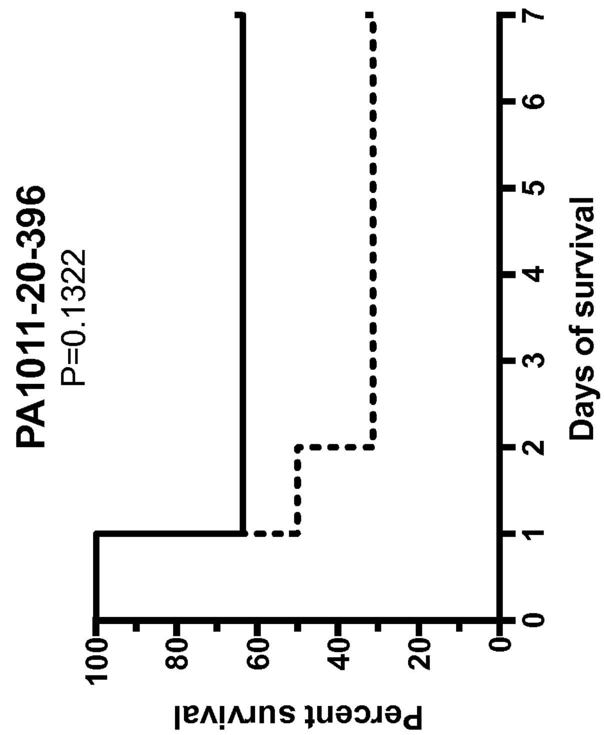
Figure 6:
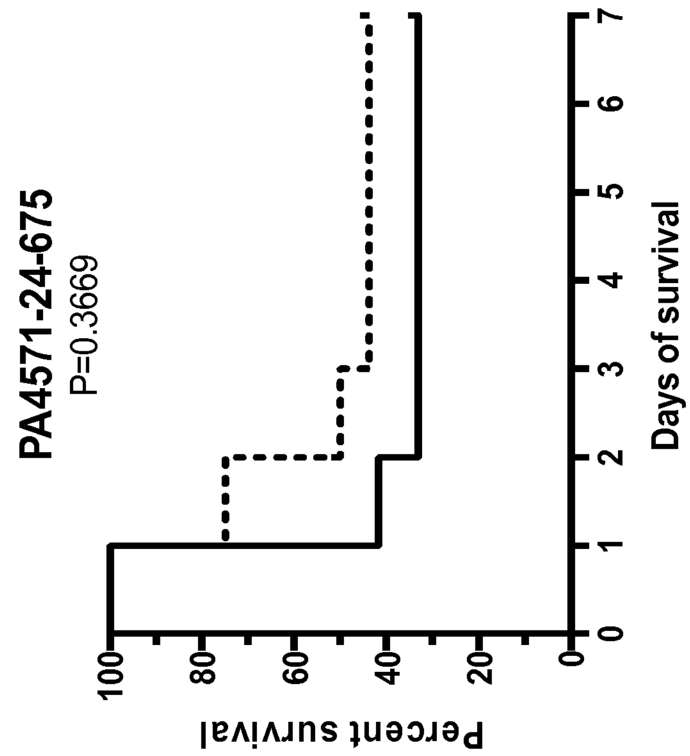
Figure 5:
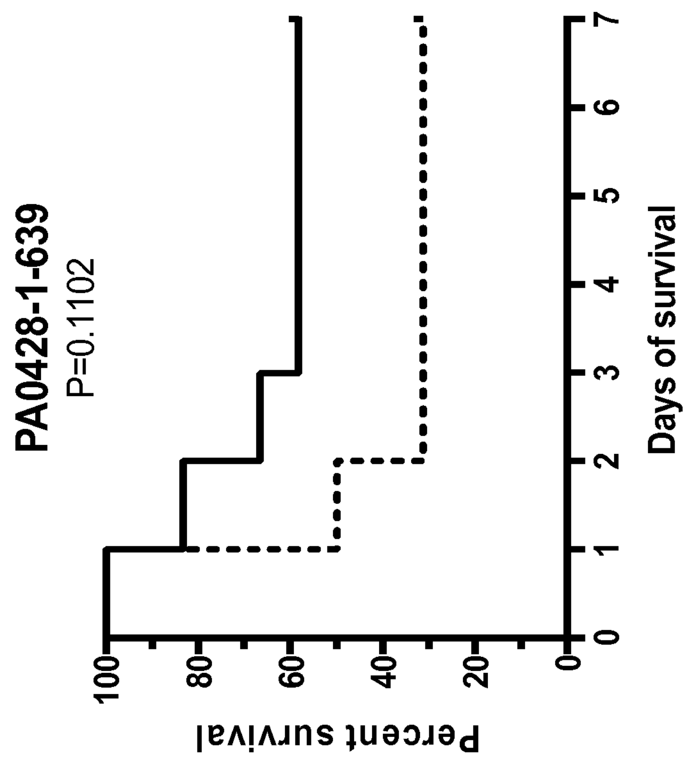
Figure 8:
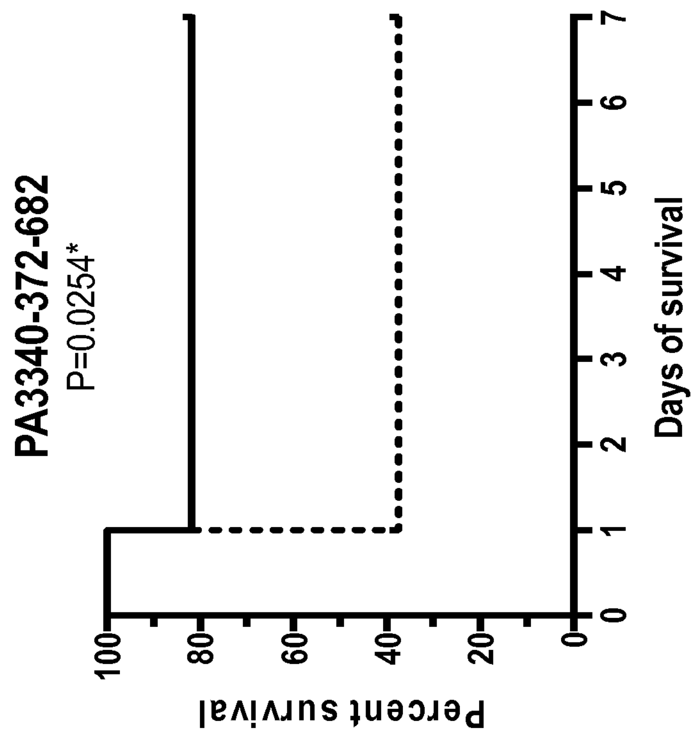
Figure 7:
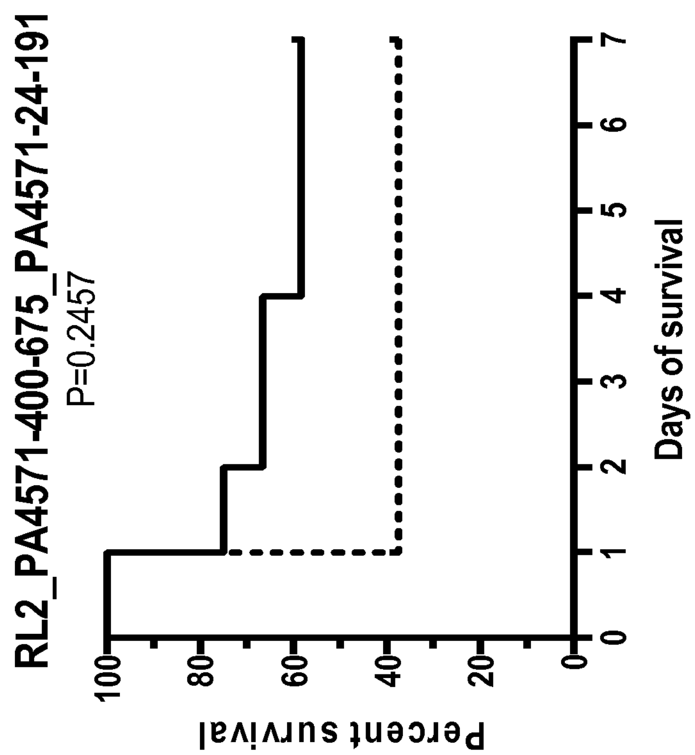
Figure 10:
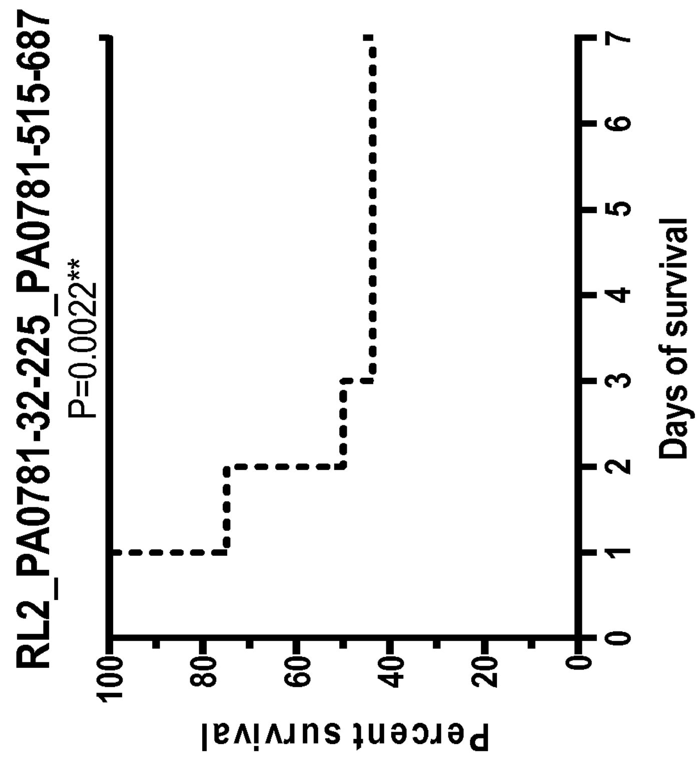
Figure 9:
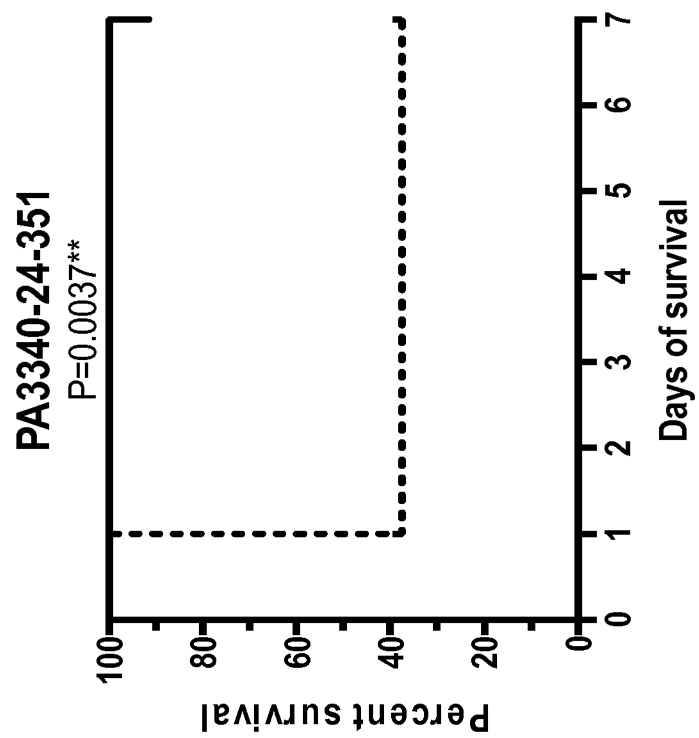
Figure 12:
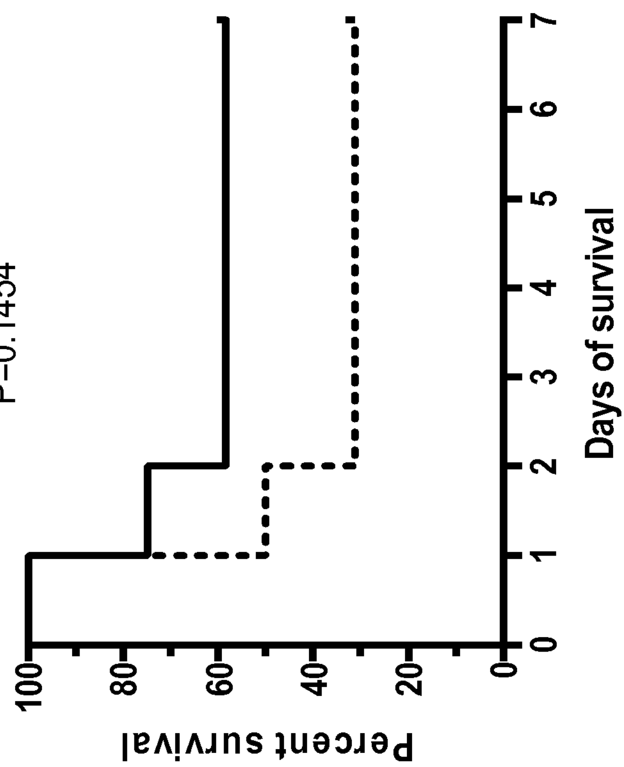
Figure 11:
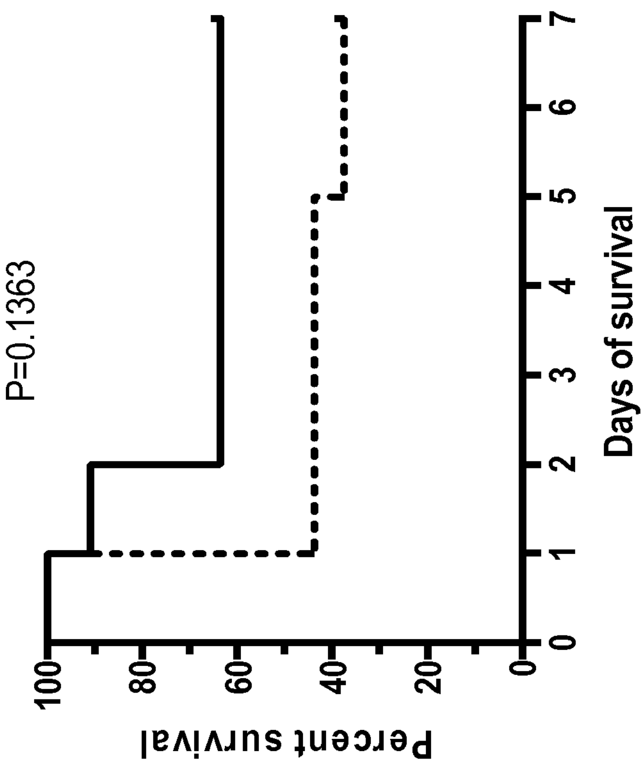
Figure 14:
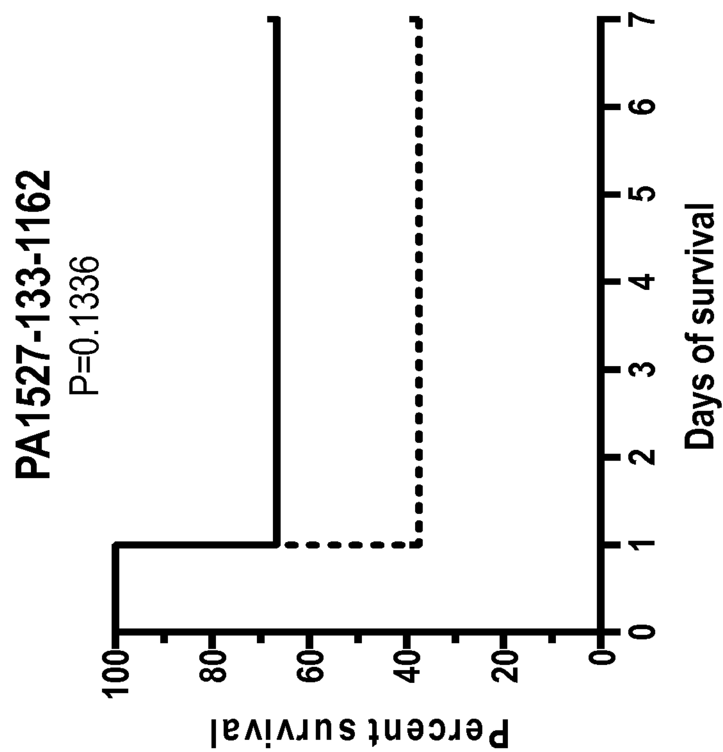
Figure 13:
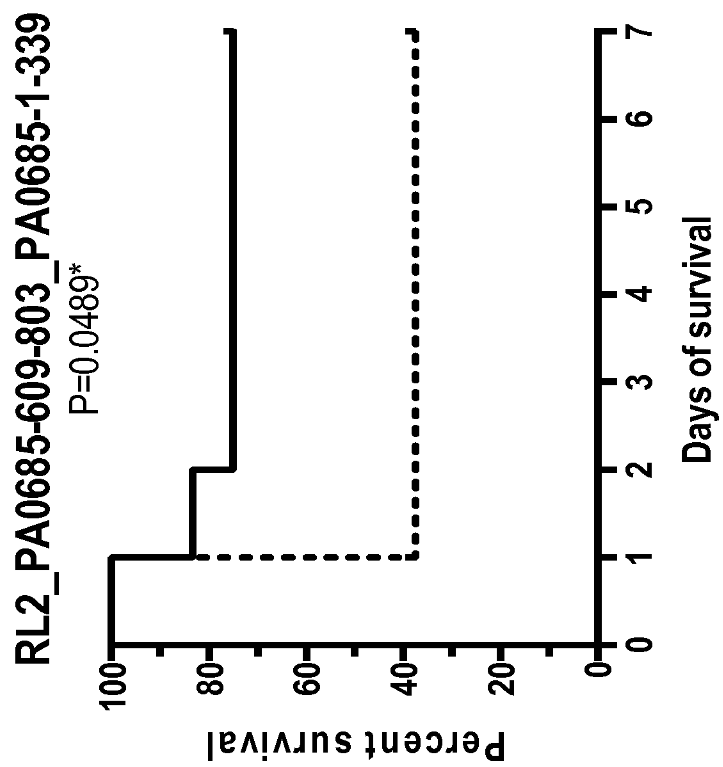
Figure 16:
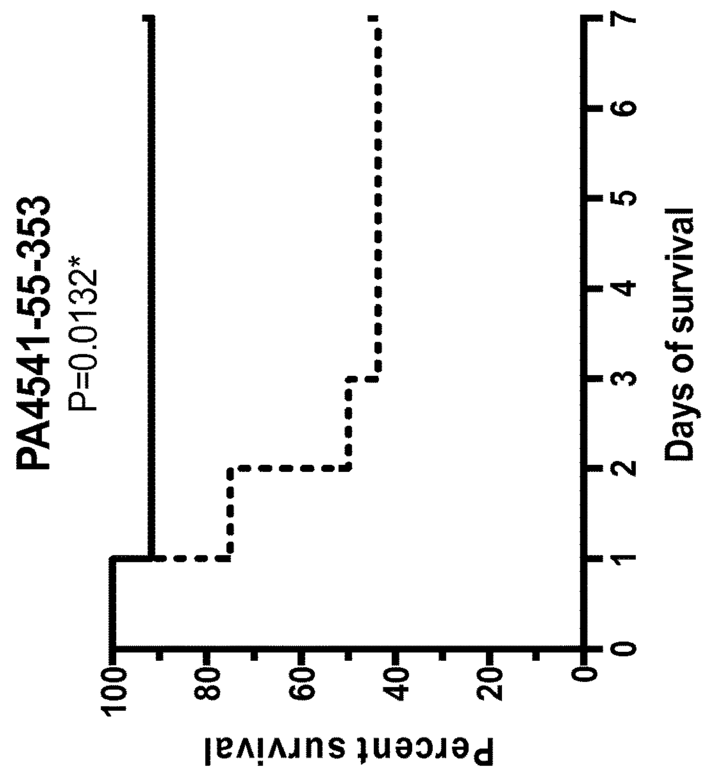
Figure 15:
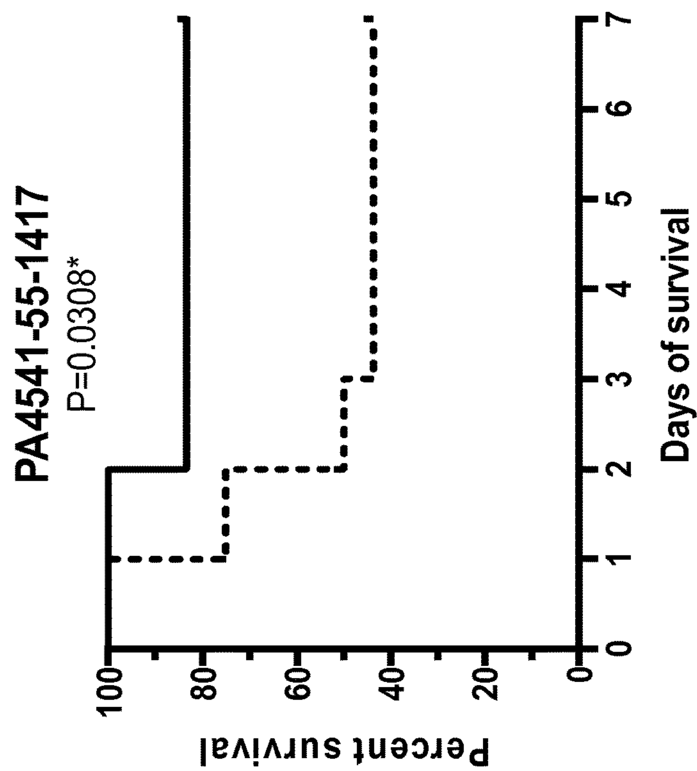
Figure 18:
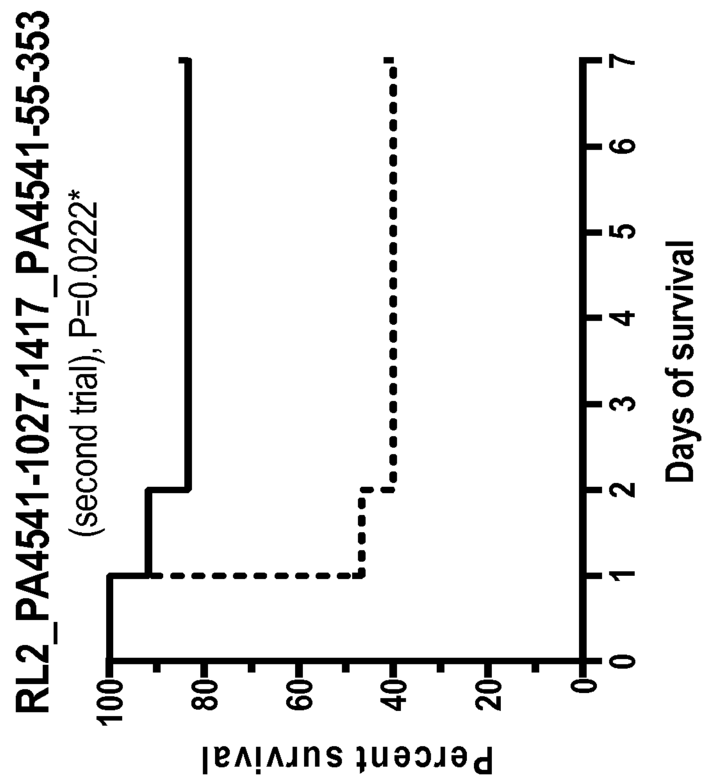
Figure 17:
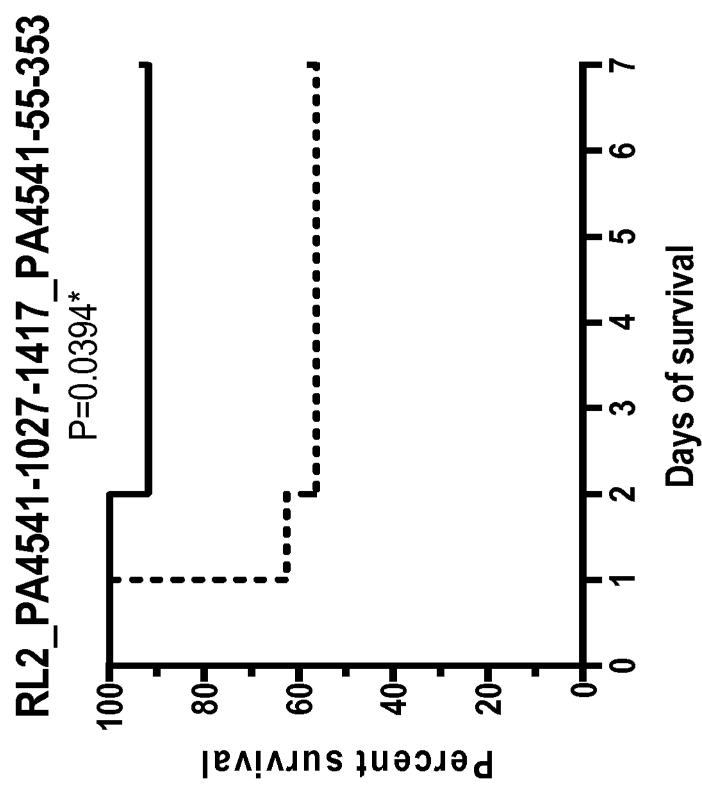

FIGS. 1-18: Effect of immunization with 17 different *P. aeruginosa* proteins on the survival of mice challenged with a lethal dose of *P. aeruginosa* PAO1.

FIGS. 1-18 show the survival curves of the protein-immunized mice (black line) and the control group challenged in parallel (dotted line). Group size 12-16 mice. The data were analyzed using log-rank (Mantel-Cox) test, where P 0.05 was regarded as significant. See also data in Table 2.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" s the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif})\cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAAC-3' and 5'-ATACGGGAC-3' will provide the sequence identity 77.8% ($N_{ref}=9$ and $N_{dif}=2$). It will be understood that such a sequence identity determination requires that the two aligned sequences are aligned so that there are no overhangs between the two sequences: each amino acid in each sequence will have to be matched with a counterpart in the other sequence.

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "linker" is an amino acid sequence, which is introduced between two other amino acid sequences in order to separate them spatially. A linker may be "rigid", meaning that it does substantially not allow the two amino acid sequences that it connects to move freely relative to each other. Likewise, a "flexible" linker allows the two sequences connected via the linker to move substantially freely relative to each other. In the fusion proteins, which are part of the present invention, both types of linkers are useful. However, one particular interesting linker useful in the present invention has the 12 amino acid residuce sequence AEAAAKEAAAKA (SEQ ID NO: 43). Other linkers of interet are listed below.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule prese An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens*, *Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterelogous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

Specific Embodiments of the Invention

The Polypeptides of the Invention

In some embodiments the at least 5 contiguous amino acids referred to in option b) in the definition of the first aspect of the invention constitute at least or exactly or at most 6, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, or at least or exactly or at most 134 contiguous amino acid residues.

The number of contiguous amino acids in option b) can be higher, for all of SEQ ID NOs. 2-30. Another way to phrase this is that for each of SEQ ID NOs: 1-14, the number of the contiguous amino acid residues is at least or exactly or at most N-n, where N is the length of the sequence ID in question and n is any integer between 1 and N-5; that is, the at least or exactly 5 contiguous amino acids can be at least any number between 5 and the length of the reference sequence minus one, in increments of one.

Insofar as embodiment b relates to SEQ ID NOs: 2-14, the at least 5 contiguous amino acids referred to in option b) in the definition of the first aspect of the invention may also constitute at least or exactly or at most 135, at least or exactly or at most 136, or at least or exactly or at most 137contiguous amino acid residues.

Insofar as embodiment b relates to SEQ ID NOs: 3-14, the at least 5 contiguous amino acids referred to in option b) in the definition of the first aspect of the invention may also constitute at least or exactly or at most 138, at least or exactly or at most 139, or at least or exactly or at most 140 contiguous amino acid residues.

Insofar as embodiment b relates to SEQ ID NOs: 4-14, the at least 5 contiguous amino acids referred to in option b) in the definition of the first aspect of the invention may also constitute at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, or at least or exactly or at most 149 contiguous amino acid residues.

Insofar as embodiment b relates to SEQ ID NOs: 5-15, the at least 5 contiguous amino acids referred to in option b) in the definition of the first aspect of the invention may also constitute at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, or at least or exactly or at most 236 contiguous amino acid residues.

Insofar as embodiment b relates to SEQ ID NOs: 6-14, the at least 5 contiguous amino acids referred to in option b) in the definition of the first aspect of the invention may also constitute at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, or at least or exactly or at most 395 contiguous amino acid residues.

Insofar as embodiment b relates to SEQ ID NOs: 7-14, the at least 5 contiguous amino acids referred to in option b) in the definition of the first aspect of the invention may also constitute at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, or at least or exactly or at most 542 contiguous amino acid residues.

Insofar as embodiment b relates to SEQ ID NOs: 8-14, the at least 5 contiguous amino acids referred to in option b) in the definition of the first aspect of the invention may also constitute at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, or at least or exactly or at most 638 contiguous amino acid residues.

Insofar as embodiment b relates to SEQ ID NOs: 9-14, the at least 5 contiguous amino acids referred to in option b) in the definition of the first aspect of the invention may also constitute at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, or at least or exactly or at most 674 contiguous amino acid residues.

Insofar as embodiment b relates to SEQ ID NOs: 10-14, the at least 5 contiguous amino acids referred to in option b) in the definition of the first aspect of the invention may also constitute at least or exactly or at most 675, at least or exactly or at most 676, at least or exactly or at most 677, at least or exactly or at most 678, at least or exactly or at most 679, at least or exactly or at most 680, or at least or exactly or at most 681 contiguous amino acid residues.

Insofar as embodiment b relates to SEQ ID NOs: 11-14, the at least 5 contiguous amino acids referred to in option b) in the definition of the first aspect of the invention may also constitute at least or exactly or at most 682, at least or exactly or at most 683, at least or exactly or at most 684, at least or exactly or at most 685, or at least or exactly or at most 686 contiguous amino acid residues.

Insofar as embodiment b relates to SEQ ID NOs: 12-14, the at least 5 contiguous amino acids referred to in option b) in the definition of the first aspect of the invention may also constitute at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, or at least or exactly or at most 802 contiguous amino acid residues.

Insofar as embodiment b relates to SEQ ID NOs: 13 or 14, the at least 5 contiguous amino acids referred to in option b) in the definition of the first aspect of the invention may also constitute at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, or at least or exactly or at most 1161 contiguous amino acid residues.

Insofar as embodiment b relates to SEQ ID NO: 14, the at least 5 contiguous amino acids referred to in option b) in the definition of the first aspect of the invention may also constitute at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, or at least or exactly or at most 1416 contiguous amino acid residues.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, and 131 in any one of SEQ ID NOs: 1-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 132, 133, and 134 in any on of SEQ ID NOs: 2-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 135, 136, and 137 in any one of SEQ ID NOs: 3-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 138, 139, 140, 141, 142, 143, 144, 145, and 146 in any one of SEQ ID NOs: 4-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, and 233 in any one of SEQ ID NOs: 5-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, and 392 in any one of SEQ ID NOs: 6-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, and 539 in any one of SEQ ID NOs: 7-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, and 635 in any one of SEQ ID NOs: 8-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, and 671 in any one of SEQ ID NOs: 9-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 672, 673, 674, 675, 676, 677, and 678 in any one of SEQ ID NOs: 10-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 679, 680, 681, 682, and 683 in any one of SEQ ID NOs: 11-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, and 799 in any one of SEQ ID NOs: 12-14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, and 1158 in SEQ ID NO: 13 or 14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, and 1413 in SEQ ID NO: 14, if the length of the at least 5 amino acid residues so permit—if the length of the at least 5 amino acids is higher than 5, the N-terminal first residue will not be higher numbered than N-L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-14. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra.

In embodiments, the polypeptides defined above may form part of other fusion polypeptides, in particular part of fusion polypeptides that include at least two of the polypeptides of the present invention or polypeptides derived from any one of SEQ ID NOs: 1-30 in WO 2017/005670. In those cases, the polypeptides disclosed herein (i.e. derived from SEQ ID NOs: 1-14) or in WO 2016/005670 (where they have SEQ ID NOs: 1-30) may be fused directly end-to-end or via a peptide linker, such as the linker having SEQ ID NO: 43.

Apart from the linker having SEQ ID NO: 43 (a rigid linker) other specific linkers are also of relevance for the present invention:

| Linker Type | Name | Sequence |
|---|---|---|
| Flexible (short) | FS | GSGGGA (SEQ ID NO: 61) |
| Flexible (long) | FL | GSGGGAGSGGGA (SEQ ID NO: 62) |
| Flexible (very long) | FV1 | GSGGGAGSGGGAGSGGGA (SEQ ID NO: 63) |
| Flexible (very long) | FV2 | GSGGGAGSGGGAGSGGGAGSGGGA (SEQ ID NO: 64) |
| Flexible (medium long) | FM | GENLYFQSGG (SEQ ID NO: 65) |
| Rigid (long) | RL1 | KPEPKPAPAPKP (SEQ ID NO: 66) |
| Rigid (long) | RL2 | AEAAAKEAAAKA (SEQ ID NO: 43) |
| Rigid (medium long) | RM | SACYCELS (SEQ ID NO: 67) |

However, any peptide linker may in principle be used.

Such fusion polypeptides can include 2, 3, 4, 5, 6, 7, 8, 9, 10 or more distinct polypeptides of the present invention, which may be derived from 1, 2, 3, 4, 5, 6, 7, 8, 9, 10, 11, 12, 13, or 14 of SEQ ID NOs: 1-14

In preferred embodiments, the polypeptide of the invention detailed above is capable of inducing an adaptive immune response against the polypeptide in a mammal, in particular in a human being. Preferably, the adaptive immune response is a protective adaptive immune response against infection with *Pseudomonas aeruginosa*. The polypeptide may in these cases induce a humeral and/or a cellular immune response.

Epitopes

SEQ ID NOs: 1-14 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised agains *Pseudomonas aeruginosa* or *Pseudomonas aeruginosa* derived proteins disclosed herein are tested for binding to overlapping oligomeric peptides derived from any one of SEQ ID NO: 1-14. Thereby, the regions of the *Pseudomonas aeruginosa* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-14 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; predictionof solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 15-28) or an RNA fragment (such as SEQ ID NOs 29-42).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 156, at least 157, at least 158, at least 159, at least 160, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200 and at least 201 consecutive nucleotides in any one of SEQ ID NOs: 15-42. Longer fragments are contemplated, i.e. fragments having at least 200, at least 300 at least 400, at least 500, at least 600, at least 700, at least 800, at least 900, at least 1000, at least 1500, at least 2000, at least 2500, at least 3000, at least 3500, and at least 4000 nucleotides from those of SEQ ID NOs: 15-42 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in *E coli*. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), al-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/Heavy metals; MMTV (mouse mammary tumor virus)—Glucocorticoids; β-Interferon—poly(rl)x/poly(rc); Adenovirus 5 E2-EIA; Collagenase—Phorbol Ester (TPA); Stromelysin—Phorbol Ester (TPA); SV40-Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70-E1A/SV40 Large T Antigen; Proliferin—Phorbol Ester/TPA; Tumor Necrosis Factor—PMA; and Thyroid Stimulating Hormonea Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

An interesting production system is the use of plants. For instance, proteins can be produced at low cost in plants using an *Agrobacterium* transfection system to genetically modify plants to express genes that encode the protein of interest. One commercially available platform are those provided by iBio CMO LLC (8800 HSC Pkwy, Bryan, Tex. 77807, USA) and iBio, Inc (9 Innovatoin Way, Suite 100, Newark, Del. 19711, USA) and disclosed in e.g. EP 2 853 599, EP 1 769 068, and EP 2 192 172. Hence, in such systems the vector is an *Agrobacterium* vector or other vector suitable for transfection of plants.

As noted above, stably transformed cells are preferred—these i.a. allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JM1 09, and KC8, as well as a number of commercially available bacterial hosts such as SURE(R) Competent Cells and SOLOP ACK(TM) Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL'" Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384,253); by calcium phosphate precipitation; by using DEAE dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563,055, 5,550,318, 5,538,877 and 5,538,880); by agitation with silicon carbide fibers (U.S. Pat. Nos. 5,302,523 and 5,464,765); by *Agrobacterium* mediated transformation (U.S. Pat. Nos. 5,591,616 and 5,563,055); or by PEG mediated transformation of protoplasts (U.S. Pat. Nos. 4,684,611 and 4,952,500); by desiccation/inhibition mediated DNA uptake. Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *Pseudomonas* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 10-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Köhler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 1251), electron-dense reagents, enzymes, and ligands having specific binding partners. Enzymes are typically detected by their activity. For example, horseradish peroxidase is usually detected by its ability to convert 3,3', 5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 1251, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

An embodiment of a pharmaceutical composition of the invention comprises exactly Y or at least Y distinct (i.e. having non-identical primary structure) polypeptides of the invention described herein, where each of said Y or at least Y distinct polypeptides comprises an immunogenic amino acid sequence present in or derived from any one of SEQ ID NOs: 1-14 and wherein said Y or at least Y distinct polypeptides together comprise immunogenic amino acid sequences present in or derived from Y or at least Y of SEQ ID NOs. 1-14, wherein Y is an integer selected from 2, 3, 4, 5, 6, 7, 8, 9, 10, 11, 12, 13, 14.

A related embodiment of a pharmaceutical composition of the invention comprises exactly Y' or at least Y' distinct (i.e. having non-identical primary structure) polypeptides, wherein at least one is a polypeptide including an immunogenic amino acid sequence present in or derived from any one of SEQ ID NOs: 1-14 of the present invention and described herein, and wherein at least one other polypeptide in the composition is disclosed in WO 2017/005670 as being present in or derived from any one of SEQ ID NOs 1-30 in WO 2017/005670, and wherein said Y' or at least Y' distinct polypeptides together comprise immunogenic amino acid sequences present in or derived from Y' or at least Y' of SEQ ID NOs. 1-14 and SEQ ID NOs 1-30 in WO 2017/005670, wherein Y' is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, and 44.

Another embodiment of a pharmaceutical composition of the invention comprises a peptide/polypeptide comprising or consisting of an immunogenic amino acid sequence present in or derived from SEQ ID NO: 1 in combination with at least one *P. aeruginosa* peptide/polypeptide, in particular with at least one peptide/polypeptide comprising or consisting of an immunogenic amino acid sequence present in or derived from any one of SEQ ID NOs: 2-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 2 in combination with at least one *P. aeruginosa* peptide/polypeptide, in particular with at least one peptide/polypeptide comprising or consisting of an immunogenic amino acid sequence present in or derived from any one of SEQ ID NOs: 1, and 3-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 3 in combination with at least one *P. aeruginosa* peptide/polypeptide, in particular with at least one peptide/polypeptide comprising or consisting of an immunogenic amino acid sequence present in or derived from any one of SEQ ID NOs: 1, 2, and 4-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 4 in combination with at least one *P. aeruginosa* peptide/polypeptide, in particular with at least one peptide/polypeptide comprising or consisting of an immunogenic amino acid sequence present in or derived from any one of SEQ ID NOs: 1-3, and 5-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 5 in combination with at least one *P. aeruginosa* peptide/polypeptide, in particular with at least one peptide/polypeptide comprising or consisting of an immunogenic amino acid sequence present in or derived from any one of SEQ ID NOs: 1-4, and 6-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 6 in combination with at least one *P. aeruginosa* peptide/polypeptide, in particular with at least one peptide/polypeptide comprising or consisting of an immunogenic amino acid sequence present in or derived from any one of SEQ ID NOs: 1-5, and 7-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 7 in combination with at least one *P. aeruginosa* peptide/polypeptide, in particular with at least one peptide/polypeptide comprising or consisting of an immunogenic amino acid sequence present in or derived from any one of SEQ ID NOs: 1-6, and 8-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 8 in combination with at least one *P. aeruginosa* peptide/polypeptide, in particular with at least one peptide/polypeptide comprising or consisting of an immunogenic amino acid sequence present in or derived from any one of SEQ ID NOs: 1-7, and 9-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 9 in combination with at least one *P. aeruginosa* peptide/polypeptide, in particular with at least one peptide/polypeptide comprising or consisting of an immunogenic amino acid sequence present in or derived from any one of SEQ ID NOs: 1-8, and 10-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 10 in combination with at least one *P. aeruginosa* peptide/polypeptide, in particular with at least one peptide/polypeptide comprising or consisting of an immunogenic amino acid sequence present in or derived from any one of SEQ ID NOs: 1-9, and 11-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 11 in combination with at least one *P. aeruginosa* peptide/polypeptide, in particular with at least one peptide/polypeptide comprising or consisting of an immunogenic amino acid sequence present in or derived from any one of SEQ ID NOs: 1-10, and 12-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 12 in combination with at least one *P. aeruginosa* peptide/polypeptide, in particular with at least one peptide/polypeptide comprising or consisting of an immunogenic amino acid sequence present in or derived from any one of SEQ ID NOs: 1-11, and 13-14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 13 in combination with at least one *P. aeruginosa* peptide/polypeptide, in particular with at least one peptide/polypeptide comprising or consisting of an immunogenic amino acid sequence present in or derived from any one of SEQ ID NOs: 1-12, and 14 or disclosed in WO 2017/005670 as being present in or derived from any one of SEQ ID NOs 1-30 in WO 2017/005670. Another embodiment of a pharmaceutical composition of the invention comprises a peptide/polypeptide comprising or consisting of an immunogenic amino acid sequence present in or derived from SEQ ID NO: 14 in combination with at least one *P. aeruginosa* peptide/polypeptide, in particular with at least one peptide/polypeptide comprising or consisting of an immunogenic amino acid sequence present in or derived from any one of SEQ ID NOs: 1-13 or disclosed in WO 2017/005670 as being present in or derived from any one of SEQ ID NOs 1-30 in WO 2017/005670.

These embodiments entail combinations of peptides/polypepides which are admixed with each other. Alternatively, the same combinations of peptides/polypeptides can be constructed as fusion polypeptides, optionally separated by linkers such as the linker having SEQ ID NO: 43. Another alternative entails compositions where the immunogens are nucleic acids (DNA or RNA) encoding the peptide combinations or, preferably, encoding such fusion polypeptides.

Another embodiment of the pharmaceutical composition of the invention comprises Z or at least Z distinct nucleic acid molecules each encoding a polypeptide of the invention, where each of said Z or at least Z distinct nucleic acid molecules encodes an immunogenic amino acid sequence present in or derived from any one of SEQ ID NOs: 1-14, and wherein said at Z or least Z distinct nucleic acid molecules together encode immunogenic amino acid sequences present in or derived from at Z or least Z of SEQ ID NOs. 1-14, wherein Z is an integer selected from 1, 2, 3, 4, 5, 6, 7, 8, 9, 10, 11, 12, 13, and 14. Also, such a pharmaceutical composition may include nucleic acids that encode several immunogenic amino acid sequences disclosed herein, either as separate encoded species or as peptides fused to each other. So one variation of this embodiment is one single nucleic acid molecule, which encodes one or more of the polypeptides disclosed above or one or more of the combinations of peptides disclosed above.

A related embodiment of the pharmaceutical composition of the invention comprises Z' or at least Z' distinct nucleic acid molecules each encoding a polypeptide of the present invention, where each of said Z' or at least Z' distinct nucleic acid molecules encodes an immunogenic amino acid sequence present in or derived from any one of SEQ ID NOs: 1-14 and wherein the Z' or at least Z' distinct nucleic acids in addition encodes at least one protein or polypeptide being present in or derived from any one of SEQ ID NOs 1-30 in WO 2017/005670 and wherein said at Z or least Z distinct nucleic acid molecules together encode immunogenic amino acid sequences present in or derived from Z' or at least Z' of SEQ ID NOs. 1-14 and SEQ ID NOs 1-30 in WO 2017/005670, wherein Z' is an integer selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, and 44. Also, such a pharmaceutical composition may include nucleic acids that encode several immunogenic amino acid sequences disclosed herein, either as separate encoded species or as peptides fused to each other. So one variation of this embodiment is one single nucleic acid molecule, which encodes one or more of the polypeptides disclosed above or one or more of the combinations of peptides disclosed above.

Vaccines of the invention typically comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition or targeting the protein/pathogen. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, eg, by injection, either subcutaneously, intramuscularly, or transdermally/transcutaneously (eg. WO98/20734). Additional formulations suitable for other modes of administration include oral, pulmonary and nasal formulations, suppositories, and transdermal applications. In the case of nucleic acid vaccination and antibody treatment, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in ImIllunol 9: 271-283; Donnelly et al. (1997) Avnu Rev Innnunol 15: 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 μg of the polypeptide of the invention per administration.

In preferred embodiments of the sixth aspect, the immuniation scheme includes that the animal (e.g. the human) receives a priming administration and one or more booster administrations.

Preferred embodiments of the $6^{th}$ aspect of the invention comprise that the administration is for the purpose of inducing protective immunity against *Pseudomonas aeruginosa*. In this embodiment it is particularly preferred that the protective immunity is effective in reducing the risk of attracting infection with *Pseudomonas aeruginosa* or is effective in treating or ameliorating infection with *Pseudomonas aeruginosa.*

As mentioned herein, the preferred vaccines of the invention induce humoral immunity, so it is preferred that the administration is for the purpose of inducing antibodies specific for *Pseudomonas aeruginosa* and wherein said antibodies or B-lymphocytes producing said antibodies are subsequently recovered from the animal.

But, as also mentioned the method of the $6^{th}$ aspect may also be useful in antibody production, so in other embodiments the administration is for the purpose of inducing antibodies specific for *Pseudomonas aeruginosa* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where

- the polypeptide of the invention is for use as a pharmaceutical, in particular for use as a pharmaceutical in the treatment, prophylaxis or amelioration of infection with *Pseudomonas aeruginosa;*
- the nucleic acid fragment of the invention or the vector of the invention is for use as a pharmaceutical, in particular for use as a pharmaceutical in the treatment, prophylaxis or amelioration of infection with *Pseudomonas aeruginosa;*
- the transformed cell of the invention is for use as a pharmaceutical, in particular for use as a pharmaceutical in the treatment, prophylaxis or amelioration of infection with *Pseudomonas aeruginosa.*
- the antibody, antibody fragment or antibody analogue of the invention is for use as a pharmaceutical, in particular for use as a pharmaceutical in the treatment, prophylaxis or amelioration of infection with *Pseudomonas aeruginosa.*

Biologic Sequence Information

The full-length, native polypeptides of the invention have the following designations used herein:

| Sequence number | Polypeptide designation |
|---|---|
| SEQ ID NO: 1: | PA4877 |
| SEQ ID NO: 2: | PA4874 |
| SEQ ID NO: 3: | PA1870 |
| SEQ ID NO: 4: | PA4697 |
| SEQ ID NO: 5: | PA0833 |
| SEQ ID NO: 6: | PA1011 |
| SEQ ID NO: 7: | PA3075 |
| SEQ ID NO: 8: | PA0428 |
| SEQ ID NO: 9: | PA4571 |
| SEQ ID NO: 10: | PA3340 |
| SEQ ID NO: 11: | PA0781 |
| SEQ ID NO: 12: | PA0685 |
| SEQ ID NO: 13: | PA1527 |
| SEQ ID NO: 14: | PA4541 |

A number of the polypeptides of the invention are fragments of the full-length, native polypeptides. Such fragments are named as follows: PAXXXX_Y-Z or PAXXXX-Y-Z, where XXXX is the number in the polypeptide designation, X is the number of the N-terminal amino acid residue in the fragment and Z is the number of the C-terminal amino acid residue. For instance, PA1011_100-880 would be the polypeptide having the amino acid sequence SEQ ID NO: 6, residues 100-880.

Furthermore, some constructs of the invention are fusion polypeptides constituted by more than one of the above polypeptides. The will typically have the designation PP1 PP2, where each of PP1 and PP2 are polypeptides designated as above. An example would be PA1011_100-880_PA0685_600-700, which would be the polypeptide having the amino acid sequence SEQ ID NO: 6, residues 100-880, fused at its C-terminus to the polypeptide having SEQ ID NO: 12, residues 600-700.

Finally, some constructs have the amino acid sequence AEAAAKEAAAKA (SEQ ID NO: 43) inserted between two fusion partners. Such constructs are named as above, but prefixed with "RL2". An example would be RL2_PA1011_100-880_PA0685_600-700, which would be the polypeptide having the amino acid sequence SEQ ID NO: 6, residues 100-880, fused C-terminally to SEQ ID NO: 43, which in turn is fused C-terminally to the polypeptide having SEQ ID NO: 12, residues 600-700.

The polypeptides of the present invention have the following amino acid sequences:

SEQ ID NO: 1

MPRGDKSKYSDKQQRKAEHIEESYKAKGVSESEAEARAWATVNKQSGGGERKGGSGRAKSETAKRAD

RKDSAHRAAQARSGRPANRGSASRGKRQGSTSVSEMTREELMQLARKRDIRGRSTMRKAELIEALSRA

SEQ ID NO: 2

MNILRIPMFVLAMAVSAHGFAATAQQEKMTACNAEATTKALKGDERKAFMSGCLKAGAPAGGKATAQQE

KMKSCNADASAKSLKGDERKAFMSSCLKAGGSAKAATQQEKMKTCNADATAKALKGDERKAFMSTCLK

K

SEQ ID NO: 3

MATRRKTTPQEIDDIQDRMGSMRELDFDERRQARKARIGDERPEAEVEAEFSSRRVREAGHAGGQPDED

DGYQDNVGMDDLAPETLIDESGARSPAERGGESPADKRLRVVHGNEIGAGHGLDEAELARRDPLDGSS

DEER

SEQ ID NO: 4

MRRMILPASLLLALSSFAMAAPIYKWVDAEGVTHFGAQPPQGAQATTVNTQTAPPPDNFPLPPSTPAPTIQ

QKPADPEQKAIDDKVKQQVAKEEAERKQFCEETRNNLAQLKNNPRVRVDEGKGELRRLGEEERQERIAK

AEKAIQENCR

SEQ ID NO: 5

MFTSRCLPLAAAVTALALLAGCANNNPYDTQSQSQGGMSKTAKYGGLGALAGAVAGAAIDHNNRGKGAL

IGAAVAGAAAAGYGYYADKQEAELRRQMEGTGVEVQRQGDDIKLIMPGNITFATDSANIAPSFYAPLNNL

ANSFKQYNQNTIEIVGYTDSTGSRQHNMDLSQRRAQSVAGYLTAQGVDGTRLSTRGMGPDQPIASNST

ADGRAQNRRVEVNLRPVPGAQGPAQTQPQY

SEQ ID NO: 6

MKRLAGLTALALVIGNTSGCGWLWGPEGYFRDRGDDYLGARETPPMQLPEGVHSKPLDPLLPIPLNVATT

HEKEGEYEVPRPQPLANAGDISDYSLQRSGDSRWVVAQRPPAEVWPVARQFFEENGFRIADERPQTGEF

SSDWQSLSQLSAPLARRLSSRVSGVEPDGQARVRVRIEPGVQSNTSEVYVLSQTRAAGDTSSPSWPSKS

VAPSLDAALLDEMVASMARSAEQGGSVSLLAANSIYDTPGTFELSKDGSGNPVLTLQSDFDRSWVSVGR

ALDNADIRVDDLNRSLGVYYVNIAEGAKKPDEDKPGFFSRLFGGGEKTKEEEDAKAQRYQVRLTTVSDAV

QVTVDKDINTSAPADVAQNVLEKLQESMRNAVRGSGQRKPGQFGLGEQF

SEQ ID NO: 7

MIRLFCSLLLALLCVSAHASFSASVDRARLTEGESVELTLESDDPTLFGKPDLSPLDALFEVLGTRQVNRLA

TQNGRAQATTRWIVTLLPKQSGYVAIPPISLGASSTQPIRLHVLEARDRAKSSKLAPVFIDASVDQETVYV

QAQAILTLRIYHSVSLYDDSSLTPLAMNDAKVEQLGEARTYEKEINGIRHGVIEVRYAIFPQKSGTLEIPAQ

AFSATLVDRGSDDYNPFGPRPGRQMRVTSPSIPLQVRPKPADYPADAPWMPARALSISESWSPQPEQAQ

VGESLTRNVLLKVEGLSGTQLPPLPLPDVQGLRRYPDQPQLADQSTDQGLIGSREEREALVPEQAGRIELP

-continued

ALEVVWWNTREDRLERTSLPPRTLEVAAAPQAEAEPPAAALPLGERLEPTLWPWQLATAVLALTTLLGFGL

WWRARQLPAVIRAAANGPSSRSLLDELRRACLANDPQATRQALDAWARQQPDTLADMAARFVPLSDAL

DGLNGALYSESGHSWQGEDLWRAIRALPTTEQAPAGAVDNGGLPPLYPR

SEQ ID NO: 8

MSFSSLGLSEALARAVEAAGYSQPTPVQQRAIPAVLQGRDLMVAAQTGTGKTGGFALPVLERLFPAGHPD

REHRHGPRQARVLVLTPTRELAAQVHDSFKVYARDLPLNSTCIFGGVGMNPQIQALAKGVDVLVACPGRL

LDLAGQNKVDLSHVEILVLDEADRMLDMGFIHDVKKVLAKLPPKRQNLLFSATFSKDIVDLANKLLHNPER

IEVTPPNTTVERIEQRVFRLPAPQKRALLAHLVTVGAWEQVLVFTRTKHGANRLAEYLTKHGLPAAAIHGN

KSQNARTKALADFKANDVRILVATDIAARGLDIDQLPHVVNYELPNVEEDYVHRIGRTGRAGRSGEAISLV

APDEEKLLKAIEKMTRQRIPDGDAQGFDPEAVLPEVAQPEPREAPQKQPRRDKERRSSRERKPKDAQASN

PDSNVAAAQDGTEKPAGKRRRRGGKNKENREAGQAQQPRQSREARPAKPNRPPEVDGNRDPEEFLDDD

FDNFGNRADYVSPYQGQENKGRGRRGGQQKPQGGTGQQGRGQGQGQARGKSQGAAQGGARGQGA

GQGKAKKPRAGKPRGQGRENASRMSDAPLREPSEYGTGKQPSRQPVVINKRDLVRMDRFPTAEQLDELE

PRRKGERPALLTRNR

SEQ ID NO: 9

MPASFPRLGLLGALCSIVPLLHASEPTTDAALIEKGRYVAQLGDCIACHTGPQGAPMAGGLELKTPMGTIY

STNITPDRETGIGRYSFEEFDRAMRKGVTAEGVNLYPAMPYPSYAKISEEDMRALYAYLMHGVQPVTQAN

TPSAMSWPFNQRWGLSLWNWAFLDDAPFTPSSDADPVINRGAYLVQGLGHCGACHTPRGIAFQEKAMS

EAGRSGQFYLAGETVEQWQALSLRNLWTVEDTVQLLKTGQNRFATVSGSMTDVIHHSTQHFSDDDLLAI

ASYLKSLPAGKDDLPMPDSERPLAAPVDLYSSRGGLGYAQFCSDCHRKDGSGVPGMFPPLAGNPTVASA

NPSTLLHITLTGWKTAQTATHSRVYTMPGFAQLEDREIAEILSFVRSSWGNQGSSIDAGQVKKLRQRIEA

GNGPATTFVSPRLADMLAAPNAEQVVRGMRLHLETRELLPANVGNQLHCTSCHLNAGTVADGSPFVGVS

AFFPSYAPRAGKVIGLEERINGCFRRSMNGKPLPPDSADMQAMVAYFDWMKNNTRPQDKVAGRGVGKV

DPALKPDPENGRKVYARQCVVCHGENGEGLRNSAGEMLFPPLWGDESFNIGAGMARTFTAAAFVKHNM

PIGFQERFPLGQGGLSDQDAVDVAEYFSHQPRPDFPDKIKDWPKDKRPLDARY

SEQ ID NO: 10

MPGKALRVMLCAWSCLLAGQASALGVGDIILHSALNQPLDADIELLDVGDLGADEIEVRLAGADVFAAAG

VERLQFLNELRFSPVLQGRGGNRIHVSSIRPVQEPYLNFLVEVARPNGRIVREFTVLLDPLGYTPRMLPAAR

SGIEPQRQSSTPVPAPRSAAVVVDPALLEPGDEYLARPSDNLWAISGRLRGAGNADRAQLMEALYQLNPQ

AFVNADRHRLKAGARLRLPAGYQPERGAPGAVKEAAVEVLPPADAAVVENAPAALVEAQRQADAEAEALA

RQREELSQRMDDLQRQLQALQEQLQQRDHQVAELQQQLARRQAVRPAAPPPAAAAPSVAQPVETPTDS

QYWRWMIVLLLVLALLGVLLLRRRREEAPVPAVEPKRRVALNLPLRRAPRPPAAAPAPAKVEEQARPPVAAP

SSPPPSPPPAPAAAPRAAMAAADKLDGADIYIAYGRYGQARDLLRQVLAEQPQRLSARMKLLLVLAELGDA

AGFDALAEETLASGGNPEAIDELRGRYPALLQMPATETPAATTKDDDWSDLPLAESPVLQQPDATSGADG

FGDLNLDLDLDWGALENPLDNPDLPRRAAAGKAEPAEEPLAFESNLHELPDVAEYEHLELDQPEPATVPPE

EASASLDRARACIDSGDLDQASRILRLVVAHGDPWQKAEARELLALIA

SEQ ID NO: 11

MSSSGLFPSRPLWPLTPLALACLIVSGETLGADGRPSELPSQVITANPLGNESPATPSSVLEGDELTLRQKG

SLGETLNGLPGVSSTYFGPGASRPVIRGMDGDRIRLLRNGVGALDASSLSYDHAVPEDPNSVERLEVVRG

PAALLYGGNAIGGVVNSFDNRIPSEPVDGIHGSGELRYGGADTTRSRSGALEAGDGNFALHVDAASREFN

DVRIPGYAHSSRQRQIDGDTGKHRVQNSDGRQDGGAVGGSYHWEHGYAGLSYSGYDSNYGSPAEDDV

RLKMQQDRYAFASEIRDLEGPFTSLKLDAAYTKYEHKEIEDGETGTTFKNEGYEGRIEARNRPLGPLNGVV

GAQFANSRFSALGEEAFVPHTETDSAALFALEEWKLSDRLDLSFGARLEHTRVDPDAKGNERFAENDGSQ

-continued

SFTTGSLSTGAVYKLTPIWSLAATLSYTERAPTFYELYANGPHAATGTYEVGDADADKEKAVSTDLALRFD

NGVHKGSVGVFYSRFSNYIGLLASGRHRNEEGEVVAAGDDEALPEYLYSGVRADFYGVEAQDRIHLLESP

YGNFDLELSGDYTRAKNKDTGEPLPRIAPLRLNTALIWELQQWQARVDVEHAASQHRVPEEELSTDGYTT

LGASLGYNFDLGESRWLAFVKGTNLTNQTVRYASSILRDRVPAAGRGIEAGVKVAF

SEQ ID NO: 12

MRQSAFHHARRRWPVLGVALGALLVAACSETPKVPGVPPADEEVGRPLSSVRSGAPLRSADVRERPQAE

QARRALSAGRGVARSGGVAPVSATAAELGEQPVSLNFVDTEVEAVVRALSRATGRQFLVDPRVKGKLTLV

SEGQVPARTAYRMLTSALRMQGFSVVDVDGVSQVVPEADAKLLGGPVYGADRPAANGMVTRTFRLRYEN

AVNLIPVLRPIVAQNNPINAYPGNNTVVVTDYAENLDRVAGIIASIDIPSASDTDVVPIQNGIAVDIASTVS

ELLDSQGSGGAEQGQKTVVLADPRSNSIVIRSPSPERTQLARDLIGKLDSVQSNPGNLHVVYLRNAQATR

LAQALRGLITGDSGGEGNEGDQQRARLSGGGMLGGGNSGTGSQGLGSSGNTTGSGSSGLGGSNRSG

GAYGAMGSGQGGAGPGAMGEENSAFSAGGVTVQADATTNTLLISAPEPLYRNLREVIDLLDQRRAQVVI

ESLIVEVSEDDSSEFGIQWQAGNLGGNGVFGGVNFGQSALNTAGKNTIDVLPKGLNIGLVDGTVDIPGIG

KILDLKVLARALKSRGGTNVLSTPNLLTLDNESASIMVGQTIPFVSGQYVTDGGGTSNNPFQTIQREDVGL

KLNIRPQISEGGTVKLDVYQEVSSVDERASTAAGVVTNKRAIDTSILLDDGQIMVLGGLLQDNVQDNTDG

VPGLSSLPGVGSLFRYQKRSRTKTNLMVFLRPYIVRDAAAGRSITLNRYDFIRRAQQRVQPRHDWSVGDM

QAPVLPPAQQGIPQAAYDLRPSPRPLRAVPLGEAAPL

SEQ ID NO: 13

MRLKSIKLAGFKSFVDPTTVNFPSNMAAVVGPNGCGKSNIIDAVRWVMGESSAKNLRGESMTDVIFNGS

NTRKPVSQASIELIFDNAETTLVGEYAQYAEISIRRRVSRDGQNTYFLNGTKCRRRDITDIFLGTGLGPRSY

SIIEQGMISKLIEARPEDLRNFIEEAAGISKYKERRRETESRIRRTQENLARLTDLREELGRQLERLHRQAQ

SAEKYQEHKAEERQLKAQLGAVRWRDLNEQVGQRERVIGDQEIAFEALVAEQRGADAGIERLRDGHHEL

SERFNQVQARFYSVGGDIARVEQSIQHGQQRQRQLQDDLREAERTRQETESHLGHDRTLLATLAEEMAM

LAPEQELSAAAAEEAGIALEQAEQGMQAWQQQWDAFNQQSAEPRRQAEVQQSRIQHLEQSLERLQDRE

RRLQEERGQLAADPEDAAILELNEQVAIAELALEELQLQEQGQAERLEQLRQELQQLAAEQHQAQGELQR

LNGRIASLEALQQAALDPGQGALEWLREQGLEQRPRLAEGLRVEPGWELAVETVLGADLQAVLLDGFDGL

ALAGFGKGELRLLSPARGAATAAGSLLDKVRADADLSPWLARVKPVETLEQALAQRGALDDGESLISRDG

YWVGRHFLRVRRSDEAQGGMLARAQELEALQERREALETRVAEGEERLAAARDEQRELEGAREQVRRQV

QEEGRRHGELKAQLSAQQAKVEQLVLRRRRLDEEVAELAEQRALEQEQLSEARLTLQEALDSMALDTERR

ESLLAERDALRERLDRIRQDARTHKDHAHQLAVRVGSLKAQHNSTQQALERLDQQSARLNERCEQLNLN

LEEGAAPLEELRMKLEELLERRMAVEDELKQARLALEDADRELREVEKRRGQAEQQSQLLRGQLEQQRLE

WQGLVVRRKALQEQLAEDGYDLHTVLANLPLDASERDWEERLESLAARIQRLGPINLAAIEEYQQQSERK

RYLDSQNDDLAEALETLENVIRKIDRETRNRFKETFDQINAGLQALFPKVFGGGTAYLELTGEDLLDTGVAI

MARPPGKKNSTIHLLSGGEKALTALALVFAIFQLNPAPFCMLDEVDAPLDDANVGRYARLVKEMSEKVQFI

YITHNKIAMEMADQLMGVTMHEPGCSRLVAVDVEEAVALAEA

SEQ ID NO: 14

MNKSYTLVWNQATGCWNVASEGTRRRSKSGRGKALVVAGASLLGLFCQAPAFALPSGATVVSGDAGFQ

TSTDGRHMVIDQQSHKLITNWNEFSVRADERVSFHQPGQDAVALNRVIGRNGSDIQGRIDANGKVFLV

NPNGVVFGKSAQVNVGGLVASTLDLADRDFLAGNYQFSGDSGATVSNAGSLQASEGGSIALLGARVSN

DGLIQAQLGDVALGAGQGINLNFDGDGLLNLQVDKGSVDALAHNGGLIRADGGQVLMSARSADSLLKT

VVNNQGTLEARTLRSAEGRIVLDGGEQGTVRVAGKQDASAIGGGNGGLVLNQGANVEIQRTAQVDTHA

DQGATGTWRILSHEVSVAAVGQANAAGDGSGQVHVAQGPAGANASDSNGVTIVQQQPAVDLAAGANG

-continued

```
TSAVQSQSGANIGSGANGISVVQSQNSPNIGSGANGISVVQSQNGANIGAGASGISVVQSQNSPNIGS
GVNGVTVVQSQNGANIGSGASGITVVQSQNGANIGSGASGISVVQSQSGPSIGSGVNGVTIVQSQSGA
NIGPGVSGIDVVQTQTLPNLSPGANGSSIVQVQTLPDIAADAGNVHVVQVQTGGNKVFGNSATNVRSRT
VQARSNENVGSGLANPSSAGKGSTLHADTLARNLSTSNVEVVATRGNAHVGAPLSWDSGNGLTLTAER
GDLRINGALTAQGENASLTLNAGQRPLRIDDSLSLTGQGARVEFNSDKGYALAEGTRITLSGKNAGFRAN
GRDYSVIQDLQQLRGIDRDLGGSYVLGNRIAGGNSSFLSIGNASAFGGTFDGLGNTIDNLAVYGTGAYSG
LFSVNRGTLRNLNLERISADGAQATHYNVQVGSLAAVNLGRIDNVNASDIRIAAASKLNSLGGLVALNLG
SIDNASASGTLVGNRHTYALGGLAAENISTARGVASISNSRADFAISGQLKDHASHYGAGGLVGRNRGG
LIRSSGSQGTLSLSGHGMNLGGLVGYSSAGGLADVSASVDVSGNGQRGLYGGLIGLNVNSGIAHATAS
GKVRGTDAEALGGLIGRNLNAAINNASAHGDVSLQAGRYLGGLIGHNQAGNLANVSTSGNLSGGSLLQA
GGLIGLNANASLVNASAKGNVATRGAEAVGGLLGENLYGSVINGSASGEVTDGSGKTLGGLIGSNLGGN
HSNLKASGWVNAGANSDVGGLIGHNRGGNHSTLAASGNVTGGKGSRVGGLVGYNDAASLTNVSASGN
VSASGSRAIGGLIGSDLRGSLMLASSHGIVNDKTSHNLGGLVGRGENTSIRSAKASGAVSGGAGIRAGG
LVGSLEGWQALILGASAGGDVTAGYDSYIGGLVGFSTATISGASASGKVGGSGLLGGLVAWNQGNVMG
SSASGRLEPQIPNQIHGGLIGINFGWQSWNSVYGAAATVPMIGRHYNL

                                                        SEQ ID NO: 43
AEAAAKEAAAKA
```

The corresponding nucleic acid sequences (DNA in SEQ ID NOs. 15-28 and RNA in SEQ ID NOs: 29-42) to SEQ ID NOs: 1-42 are set forth in the electronic sequence listing that forms part of the present application. SEQ ID NOs: 44-60 set forth the sequences of specific constructs tested in the examples, cf. below, and SEQ ID NOs: 61-67 lists the sequences of a number of peptide linkers.

Example 1

Introduction

The purpose of the studies described in the following was to assess the protective effect of 17 recombinant protein constructs in a murine model of *Pseudomonas aeruginosa*-induced peritonitis. The proteins tested were

- PA4877-1-135 (SEQ ID NO: 1, residues 1-135; also shown in SEQ ID NO: 44)
- PA1870-2-141 (SEQ ID NO: 3, residues 2-141; also shown in SEQ ID NO: 45)
- PA0833-142-237 (SEQ ID NO: 5, residues 142-237; also shown in SEQ ID NO: 46)
- PA1011-20-396 (SEQ ID NO: 6, residues 20-396; also shown in SEQ ID NO: 47)
- PA0428-1-639 (SEQ ID NO: 8, residues 1-639; also shown in SEQ ID NO: 48)
- PA4571-24-675 (SEQ ID NO: 9, residues 24-675; also shown in SEQ ID NO: 49)
- RL2_PA4571-400-675_PA4571-24-191 (fusion between SEQ ID NO: 43, SEQ ID NO: 9, residues 400-675, and SEQ ID NO: 9, residues 24-191; also shown in SEQ ID NO: 50)
- PA3340-372-682 (SEQ ID NO: 10, residues 372-682; also shown in SEQ ID NO: 51)
- PA3340-24-351 (SEQ ID NO: 10, residues 24-351; also shown in SEQ ID NO: 52)
- RL2_PA0781-32-225_PA0781-515-687 (fusion between SEQ ID NO: 43, SEQ ID NO: 11, residues 32-225, and SEQ ID NO: 11, residues 515-687; also shown in SEQ ID NO: 53)
- RL2_PA0781-515-687_PA0781-32-495 (fusion between SEQ ID NO: 43, SEQ ID NO: 11, residues 515-687, and SEQ ID NO: 11, residues 32-495; also shown in SEQ ID NO: 54)
- PA0781-32-687 (SEQ ID NO: 11, residues 32-687; also shown in SEQ ID NO: 55)
- RL2_PA0685-609-803_PA0685-1-339 (fusion between SEQ ID NO: 43, SEQ ID NO: 12, residues 609-803, and SEQ ID NO. 12, residues 1-339; also shown in SEQ ID NO: 56)
- PA1527-133-1162 (SEQ ID NO: 13, residues 133-1162; also shown in SEQ ID NO: 57)
- PA4541-55-1417 (SEQ ID NO: 14, residues 55-1417; also shown in SEQ ID NO: 58)
- PA4541-55-353 (SEQ ID NO: 14, residues 55-353; also shown in SEQ ID NO: 59)
- RL2_PA4541-1027-1417_PA4541-55-353 (fusion between SEQ ID NO: 43, SEQ ID NO: 14, residues 1027-1414, and SEQ ID NO: 14, residues 55-353; also shown in SEQ ID NO: 60).

The survival of the immunized mice was compared to the survival of mice receiving immunological adjuvant only.

Materials

- NMRI mice, female (Taconic, Denmark)
- *Pseudomonas aeruginosa*, PAO1 (Iglewski batch #2 and #3.1)
- Aluminum hydroxide (Alhydrogel 2.0%, 21645-51-2, Brenntag)
- Freund's incomplete adjuvant (F5506-10X10ML, Sigma)
- PA4877-1-135 (CBCBM3L07031401-11-75, Creative Biomart)
- PA1870-2-141 (CB_CBM3L07031401-11-135, Creative Biomart)
- PA0833-142-237 (CB_CBM3L07031401-11-145, Creative Biomart)
- PA1011-20-396 (CBCBM3L07031401-11-84, Creative Biomart)

PA0428-1-639 (CB_CBM3L07031401-11-133, Creative Biomart)
PA4571-24-675 (CBCBM3L07031401-11-87, Creative Biomart)
RL2_PA4571-400-675_PA4571-24-191 (CB_CBM3L07031401-11-154, Creative Biomart)
PA3340-372-682 (CBCBM3L07031401-11-76, Creative Biomart)
PA3340-24-351 (CBCBM3L07031401-11-92, Creative Biomart)
RL2_PA0781-32-225_PA0781-515-687 (CB_CBM3L07031401-11-142, Creative Biomart)
RL2_PA0781-515-687_PA0781-32-495 (CB_CBM3L07031401-11-150, Creative Biomart)
PA0781-32-687 (CBCBM3L07031401-11-88, Creative Biomart)
RL2_PA0685-609-803_PA0685-1-339 (CB_CBM3L07031401-11-149, Creative Biomart)
PA1527-133-1162 (CB_CBM3L07031401-11-155, Creative Biomart)
PA4541-55-1417 (CBCBM3L07031401-11-86, Creative Biomart)
PA4541-55-353 (CB_CBM3L07031401-11-141, Creative Biomart)
RL2_PA4541-1027-1417_PA4541-55-353 (CB_CBM3L07031401-11-153, Creative Biomart)

Immunization Protocol

Female NMRI mice were immunized with the recombinant proteins listed above in combination with adjuvant. In every challenge setup, one group of 16 mice were immunized with adjuvant alone, making up the negative control group. The amount of adjuvant used for immunization of the control group was the same as the amount used when immunizing the protein-treated groups. Each mouse was immunized subcutaneously three times at approximately two week intervals. At all three immunizations, the mice in the protein-treated groups received 15 μg protein. For the first immunization, the proteins were mixed with aluminum hydroxide ($Al(OH)_3$) and Freund's incomplete adjuvant (IFA), whereas only $Al(OH)_3$ was used for the subsequent booster immunizations.

Preparation of Bacterial Inoculum

The bacteria used in the animal model of peritonitis were prepared in advance and frozen at −80° C. in aliquots; bacterial matter was streaked out on a Luria broth (LB) agar plate and incubated at 37° C. overnight. A single colony of *P. aeruginosa* was used for the inoculation of 50 mL of LB media. The culture was incubated at 37° C., with continuous shaking, overnight.

The following day 1 l of LB media was inoculated with 10 ml of the overnight culture, and incubated at 37° C. and continuous shaking for 6 hours. The bacterial suspension was centrifuged at 3,000×g for 10 minutes, and the pellet washed twice in 400 ml sterile PBS. After each wash the bacterial suspension was centrifuged at 3,000×g for 10 minutes. The bacterial pellet was resuspended in 10-15 ml PBS, and glycerol was added to a final concentration of 16%. The suspension was thoroughly mixed, aliquoted into 1 ml aliquots and stored at −80° C. The number of colony forming units (CFU) per ml was determined for the frozen stock, as aliquots were thawed on ice and serially diluted in sterile saline. The dilutions were plated on LB agar plates, and incubated at 37° C., overnight. The number of CFU per ml was established the following day. The procedure was carried out in duplicate, i.e. for two aliquots, to verify that the aliquots were homogenous.

Immediately prior to inoculation aliquots were thawed and diluted in sterile saline to the desired inoculum size, i.e. number of CFU per inoculum volume. After each inoculation, the inoculum size was confirmed by plating on LB agar plates.

Challenge Setup

The mice were housed at the Biomedical Laboratory at the University of Southern Denmark. The animals were kept in an environment characterized by a 12 hours light-dark cycle and temperature and humidity control. They had access to food and water ad libitum. The experimental procedures were carried out in accordance with the guidelines of the Danish National Animal Ethics Committee (license number 2015-15-0201-00680).

The experiments were performed in class 2 certified facilities at the Biomedical Laboratory. Two weeks after the third immunization the mice were inoculated intraperitoneally with a dose of *P. aeruginosa*_PAO1 (Iglewski, batch #2 or 3.1) previously found to cause a 90% mortality of naïve mice. Following challenge, the mice were assessed daily to register symptoms and development of disease over the course of the 7 days. To ensure a consistent evaluation of all animals each animal was scored individually following the scale for clinical symptoms given in table 1.

TABLE 1

Scale of clinical symptoms. The mice were individually assessed on their physical appearance and behavior, noting the presence or absence of the given characteristics.

| Score | Symptoms |
|---|---|
| 0 | No symptoms |
| 1 | Decreased spontaneous activity, slightly ruffled fur, weight loss maximum 10% |
| 2 | Decreased provoked activity, ruffled fur, weight loss maximum 15% |
| 3 | Symptoms like 1 or 2 and/or semi-closed eyes, decreased food and water uptake, weight loss maximum 20% |
| 4 | No activity when provoked, cold to the touch, no uptake of food and water, weight loss maximum 20% |

Humane Endpoints

Apart from the registration of clinical symptoms, body weight and temperature of each animal were registered daily following challenge. The weight loss was calculated as a percentage of the body weight registered prior to inoculation. Animals were euthanized if either of the following humane endpoints were reached: a body temperature below 25° C. (when measured with an infrared laser) or a weight loss above 20% of the initial body weight. Additionally, mice scored 3 over three successive days, without signs of improvements such as weight gain, or 4 once were euthanized.

Results

Survival Following Lethal Challenge

The survival of mice immunized with a protein in combination with the adjuvants $Al(OH)_3$ and IFA was compared to the survival of mice in the negative control group. FIGS. 1-18 show the survival curves for the different groups. The survival is also summarized in Table 2 below. The results derive from a total of 7 different studies. Only one protein, RL2_PA4541-1027-1417_PA4541-55-353, was tested in two independent trials.

TABLE 2

Survival of protein-immunized mice after a lethal challenge with *P. aeruginosa* PAO1. The survival of the protein-treated mice was compared to the survival of mice in the negative control group, and log-rank (Mantel-Cox) was used to analyze the data.

| Protein ID | Survival control group | Survival protein-treated group | P-value |
|---|---|---|---|
| PA4877-1-135 | 7 of 16 | 3 of 12 (25%) | 0.1752 |
| PA1870-2-141 | 8 of 16 | 10 of 12 (83.3%) | 0.0788 |
| PA0833-142-237 | 6 of 15 | 10 of 12 (83.3%) | 0.0222 |
| PA1011-20-396 | 5 of 16 | 7 of 11 (63.6%) | 0.1322 |
| PA0428-1-639 | 5 of 16 | 7 of 12 (58.3%) | 0.1102 |
| PA4571-24-675 | 7 of 16 | 4 of 12 (23.3%) | 0.3669 |
| RL2_PA4571-400-675_PA4571-24-191 | 6 of 16 | 7 of 12 (58.3%) | 0.2457 |
| PA3340-372-682 | 6 of 16 | 9 of 11 (81.8%) | 0.0254 |
| PA3340-24-351 | 6 of 16 | 11 of 12 (91.7%) | 0.0037 |
| RL2_PA0781-32-225_PA0781-515-687 | 7 of 16 | 12 of 12 (100%) | 0.0022 |
| RL2_PA0781-515-687_PA0781-32-495 | 6 of 16 | 7 of 11 (63.6%) | 0.1363 |
| PA0781-32-687 | 5 of 16 | 7 of 12 (58.3%) | 0.1454 |
| RL2_PA0685-609-803_PA0685-1-339 | 6 of 16 | 9 of 12 (75.0%) | 0.0489 |
| PA1527-133-1162 | 6 of 16 | 8 of 12 (66.7%) | 0.1336 |
| PA4541-55-1417 | 7 of 16 | 10 of 12 (83.3%) | 0.0308 |
| PA4541-55-353 | 7 of 16 | 11 of 12 (91.7%) | 0.0132 |
| RL2_PA4541-1027_1417_PA4541-55-353 (first trial) | 9 of 16 | 11 of 12 (91.7%) | 0.0394 |
| RL2_PA4541-1027_1417_PA4541-55-353 (second trial) | 6 of 15 | 10 of 12 (83.3%) | 0.0222 |

CONCLUSIONS

Of the 17 proteins tested, 8 induced significant protection against a lethal *P. aeruginosa* infection. The protective candidates were PA0833-142-237, PA3340-372-682, PA3340-24-351, RL2_PA0781-32-225_PA0781-515-687, RL2_PA0685-609-803_PA0685-1-339, PA4541-55-1417, PA4541-55-353 and RL2_PA4541-1027-1417_PA4541-55-353.

The invention claimed is:

1. A pharmaceutical composition comprising a polypeptide, which can be encoded by a DNA sequence and which comprises:

a) an amino acid sequence consisting of at least or exactly 50 contiguous amino acid residues from amino acid residues 142-237 of SEQ ID NO 5, or b) an amino acid sequence having a sequence identity of at least 80% with the amino acid sequence of a) and an immunological adjuvant and a pharmaceutically acceptable carrier, vehicle or diluent, wherein the polypeptide lacks residues SEQ ID NO: 5.

2. The pharmaceutical composition according to claim 1, wherein the adjuvant is an aluminium based adjuvant.

3. The pharmaceutical composition according to claim 1, wherein the at least or exactly 50 contiguous amino acids of the polypeptide are at least or exactly or at most 51, at least or exactly or at most 52, at least or exactly or at most 53, at least or exactly or at most 54, at least or exactly or at most 55, at least or exactly or at most 56 at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most at least or exactly or at most 73, at least or exactly or at most 74, at least, or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 95, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 19, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, least or exactly at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly ar at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at east 165, at least or exactly or at most 166, at least or exactly or at most 167, at least or exactly or at most 168, at least or exactly or at most 169, at least or exactly or at most 17€3, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, exactly or at most 232 contiguous amino acid residues.

4. The pharmaceutical composition according to claim 1, wherein the polypeptide has a sequence identity with the amino acid sequence of a) of at least 85%, such as at least 90%, at least 91%, at least 92%, at least 93%, at least 94%, at least 95%, at least 96%, at least 97%, at least 98%, and at least 99%.

5. The pharmaceutical composition according to claim 1, wherein the polypeptide has an N-terminal amino acid residue corresponding to any one of amino acid residues 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175 176, 177, 178, 179, 180, 181, 182, 183, 184, 185, 186, 187, and 188 in SEQ ID NO; 5, with the proviso that the selected amino acid residue satisfies the formula N≤238-n, where N is the number of the selected residue, and n is the number of consecutive amino acid residues.

6. The pharmaceutical composition according to claim 1, wherein the polypeptide is fused or conjugated to an immunogenic carrier.

7. The pharmaceutical composition according to claim 6, wherein the polypeptide is fused to the immunogenic carrier via a linker.

8. The pharmaceutical composition according to claim 6, wherein the immunogenic a polypeptide that induces T-helper lymphocyte responses in a z majority of humans.

9. The pharmaceutical composition according to claim 8, wherein the immunogenic carrier is selected from the group consisting of keyhole limpet hemocyanin or a fragment thereof, tetanus toxoid or a fragment thereof, and diphtheria toxoid or a fragment thereof.

* * * * *

SEQUENCE LISTING

```
<160> NUMBER OF SEQ ID NOS: 67

<210> SEQ ID NO 1
<211> LENGTH: 135
<212> TYPE: PRT
<213> ORGANISM: Pseudomonas aeruginosa

<400> SEQUENCE: 1

Met Pro Arg Gly Asp Lys Ser Lys Tyr Ser Asp Lys Gln Gln Arg Lys
1               5                   10                  15

Ala Glu His Ile Glu Glu Ser Tyr Lys Ala Lys Gly Val Ser Glu Ser
            20                  25                  30

Glu Ala Glu Ala Arg Ala Trp Ala Thr Val Asn Lys Gln Ser Gly Gly
        35                  40                  45

Gly Glu Arg Lys Gly Gly Ser Gly Arg Ala Lys Ser Glu Thr Ala Lys
    50                  55                  60

Arg Ala Asp Arg Lys Asp Ser Ala His Arg Ala Ala Gln Ala Arg Ser
65                  70                  75                  80

Gly Arg Pro Ala Asn Arg Gly Ser Ala Ser Arg Gly Lys Arg Gln Gly
                85                  90                  95

Ser Thr Ser Val Ser Glu Met Thr Arg Glu Glu Leu Met Gln Leu Ala
            100                 105                 110

Arg Lys Arg Asp Ile Arg Gly Arg Ser Thr Met Arg Lys Ala Glu Leu
        115                 120                 125

Ile Glu Ala Leu Ser Arg Ala
    130                 135


<210> SEQ ID NO 2
<211> LENGTH: 138
<212> TYPE: PRT
```

```
<213> ORGANISM: Pseudomonas aeruginosa

<400> SEQUENCE: 2

Met Asn Ile Leu Arg Ile Pro Met Phe Val Leu Ala Met Ala Val Ser
1               5                   10                  15

Ala His Gly Phe Ala Ala Thr Ala Gln Gln Glu Lys Met Thr Ala Cys
            20                  25                  30

Asn Ala Glu Ala Thr Thr Lys Ala Leu Lys Gly Asp Glu Arg Lys Ala
        35                  40                  45

Phe Met Ser Gly Cys Leu Lys Ala Gly Ala Pro Ala Gly Gly Lys Ala
    50                  55                  60

Thr Ala Gln Gln Glu Lys Met Lys Ser Cys Asn Ala Asp Ala Ser Ala
65                  70                  75                  80

Lys Ser Leu Lys Gly Asp Glu Arg Lys Ala Phe Met Ser Ser Cys Leu
                85                  90                  95

Lys Ala Gly Gly Ser Ala Lys Ala Ala Thr Gln Gln Glu Lys Met Lys
            100                 105                 110

Thr Cys Asn Ala Asp Ala Thr Ala Lys Ala Leu Lys Gly Asp Glu Arg
        115                 120                 125

Lys Ala Phe Met Ser Thr Cys Leu Lys Lys
    130                 135


<210> SEQ ID NO 3
<211> LENGTH: 141
<212> TYPE: PRT
<213> ORGANISM: Pseudomonas aeruginosa

<400> SEQUENCE: 3

Met Ala Thr Arg Arg Lys Thr Thr Pro Gln Glu Ile Asp Asp Ile Gln
1               5                   10                  15

Asp Arg Met Gly Ser Met Arg Glu Leu Asp Phe Asp Glu Arg Arg Gln
            20                  25                  30

Ala Arg Lys Ala Arg Ile Gly Asp Glu Arg Pro Glu Ala Glu Val Glu
        35                  40                  45

Ala Glu Phe Ser Ser Arg Arg Val Arg Glu Ala Gly His Ala Gly Gly
    50                  55                  60

Gln Pro Asp Glu Asp Asp Gly Tyr Gln Asp Asn Val Gly Met Asp Asp
65                  70                  75                  80

Leu Ala Pro Glu Thr Leu Ile Asp Glu Ser Gly Ala Arg Ser Pro Ala
                85                  90                  95

Glu Arg Gly Gly Glu Ser Pro Ala Asp Lys Arg Leu Arg Val Val His
            100                 105                 110

Gly Asn Glu Ile Gly Ala Gly His Gly Leu Asp Glu Ala Glu Leu Ala
        115                 120                 125

Arg Arg Asp Pro Leu Asp Gly Ser Ser Asp Glu Glu Arg
    130                 135                 140


<210> SEQ ID NO 4
<211> LENGTH: 150
<212> TYPE: PRT
<213> ORGANISM: Pseudomonas aeruginosa

<400> SEQUENCE: 4

Met Arg Arg Met Ile Leu Pro Ala Ser Leu Leu Leu Ala Leu Ser Ser
1               5                   10                  15

Phe Ala Met Ala Ala Pro Ile Tyr Lys Trp Val Asp Ala Glu Gly Val
            20                  25                  30
```

```
Thr His Phe Gly Ala Gln Pro Pro Gln Gly Ala Gln Ala Thr Thr Val
        35                  40                  45

Asn Thr Gln Thr Ala Pro Pro Pro Asp Asn Phe Pro Leu Pro Pro Ser
    50                  55                  60

Thr Pro Ala Pro Thr Ile Gln Gln Lys Pro Ala Asp Pro Glu Gln Lys
65                  70                  75                  80

Ala Ile Asp Asp Lys Val Lys Gln Gln Val Ala Lys Glu Glu Ala Glu
                85                  90                  95

Arg Lys Gln Phe Cys Glu Glu Thr Arg Asn Asn Leu Ala Gln Leu Lys
            100                 105                 110

Asn Asn Pro Arg Val Arg Val Asp Glu Gly Lys Gly Glu Leu Arg Arg
        115                 120                 125

Leu Gly Glu Glu Glu Arg Gln Glu Arg Ile Ala Lys Ala Glu Lys Ala
    130                 135                 140

Ile Gln Glu Asn Cys Arg
145                 150


<210> SEQ ID NO 5
<211> LENGTH: 237
<212> TYPE: PRT
<213> ORGANISM: Pseudomonas aeruginosa

<400> SEQUENCE: 5

Met Phe Thr Ser Arg Cys Leu Pro Leu Ala Ala Ala Val Thr Ala Leu
1               5                   10                  15

Ala Leu Leu Ala Gly Cys Ala Asn Asn Asn Pro Tyr Asp Thr Gln Ser
            20                  25                  30

Gln Ser Gln Gly Gly Met Ser Lys Thr Ala Lys Tyr Gly Gly Leu Gly
        35                  40                  45

Ala Leu Ala Gly Ala Val Ala Gly Ala Ala Ile Asp His Asn Asn Arg
    50                  55                  60

Gly Lys Gly Ala Leu Ile Gly Ala Ala Val Ala Gly Ala Ala Ala Ala
65                  70                  75                  80

Gly Tyr Gly Tyr Tyr Ala Asp Lys Gln Glu Ala Glu Leu Arg Arg Gln
                85                  90                  95

Met Glu Gly Thr Gly Val Glu Val Gln Arg Gln Gly Asp Asp Ile Lys
            100                 105                 110

Leu Ile Met Pro Gly Asn Ile Thr Phe Ala Thr Asp Ser Ala Asn Ile
        115                 120                 125

Ala Pro Ser Phe Tyr Ala Pro Leu Asn Asn Leu Ala Asn Ser Phe Lys
    130                 135                 140

Gln Tyr Asn Gln Asn Thr Ile Glu Ile Val Gly Tyr Thr Asp Ser Thr
145                 150                 155                 160

Gly Ser Arg Gln His Asn Met Asp Leu Ser Gln Arg Arg Ala Gln Ser
                165                 170                 175

Val Ala Gly Tyr Leu Thr Ala Gln Gly Val Asp Gly Thr Arg Leu Ser
            180                 185                 190

Thr Arg Gly Met Gly Pro Asp Gln Pro Ile Ala Ser Asn Ser Thr Ala
        195                 200                 205

Asp Gly Arg Ala Gln Asn Arg Arg Val Glu Val Asn Leu Arg Pro Val
    210                 215                 220

Pro Gly Ala Gln Gly Pro Ala Gln Thr Gln Pro Gln Tyr
225                 230                 235
```

<210> SEQ ID NO 6
<211> LENGTH: 396
<212> TYPE: PRT
<213> ORGANISM: Pseudomonas aeruginosa

<400> SEQUENCE: 6

```
Met Lys Arg Leu Ala Gly Leu Thr Ala Leu Ala Leu Val Ile Gly Asn
1               5                   10                  15

Thr Ser Gly Cys Gly Trp Leu Trp Gly Pro Glu Gly Tyr Phe Arg Asp
            20                  25                  30

Arg Gly Asp Asp Tyr Leu Gly Ala Arg Glu Thr Pro Pro Met Gln Leu
        35                  40                  45

Pro Glu Gly Val His Ser Lys Pro Leu Asp Pro Leu Leu Pro Ile Pro
    50                  55                  60

Leu Asn Val Ala Thr Thr His Glu Lys Glu Gly Glu Tyr Glu Val Pro
65                  70                  75                  80

Arg Pro Gln Pro Leu Ala Asn Ala Gly Asp Ile Ser Asp Tyr Ser Leu
                85                  90                  95

Gln Arg Ser Gly Asp Ser Arg Trp Val Val Ala Gln Arg Pro Pro Ala
            100                 105                 110

Glu Val Trp Pro Val Ala Arg Gln Phe Phe Glu Glu Asn Gly Phe Arg
        115                 120                 125

Ile Ala Asp Glu Arg Pro Gln Thr Gly Glu Phe Ser Ser Asp Trp Gln
    130                 135                 140

Ser Leu Ser Gln Leu Ser Ala Pro Leu Ala Arg Arg Leu Ser Ser Arg
145                 150                 155                 160

Val Ser Gly Val Glu Pro Asp Gly Gln Ala Arg Val Arg Val Arg Ile
                165                 170                 175

Glu Pro Gly Val Gln Ser Asn Thr Ser Glu Val Tyr Val Leu Ser Gln
            180                 185                 190

Thr Arg Ala Ala Gly Asp Thr Ser Ser Pro Ser Trp Pro Ser Lys Ser
        195                 200                 205

Val Ala Pro Ser Leu Asp Ala Ala Leu Leu Asp Glu Met Val Ala Ser
    210                 215                 220

Met Ala Arg Ser Ala Glu Gln Gly Gly Ser Val Ser Leu Leu Ala Ala
225                 230                 235                 240

Asn Ser Ile Tyr Asp Thr Pro Gly Thr Phe Glu Leu Ser Lys Asp Gly
                245                 250                 255

Ser Gly Asn Pro Val Leu Thr Leu Gln Ser Asp Phe Asp Arg Ser Trp
            260                 265                 270

Val Ser Val Gly Arg Ala Leu Asp Asn Ala Asp Ile Arg Val Asp Asp
        275                 280                 285

Leu Asn Arg Ser Leu Gly Val Tyr Tyr Val Asn Ile Ala Glu Gly Ala
    290                 295                 300

Lys Lys Pro Asp Glu Asp Lys Pro Gly Phe Phe Ser Arg Leu Phe Gly
305                 310                 315                 320

Gly Gly Glu Lys Thr Lys Glu Glu Glu Asp Ala Lys Ala Gln Arg Tyr
                325                 330                 335

Gln Val Arg Leu Thr Thr Val Ser Asp Ala Val Gln Val Thr Val Asp
            340                 345                 350

Lys Asp Ile Asn Thr Ser Ala Pro Ala Asp Val Ala Gln Asn Val Leu
        355                 360                 365

Glu Lys Leu Gln Glu Ser Met Arg Asn Ala Val Arg Gly Ser Gly Gln
    370                 375                 380
```

```
Arg Lys Pro Gly Gln Phe Gly Leu Gly Glu Gln Phe
385                 390                 395


<210> SEQ ID NO 7
<211> LENGTH: 543
<212> TYPE: PRT
<213> ORGANISM: Pseudomonas aeruginosa

<400> SEQUENCE: 7

Met Ile Arg Leu Phe Cys Ser Leu Leu Leu Ala Leu Leu Cys Val Ser
1               5                   10                  15

Ala His Ala Ser Phe Ser Ala Ser Val Asp Arg Ala Arg Leu Thr Glu
            20                  25                  30

Gly Glu Ser Val Glu Leu Thr Leu Glu Ser Asp Asp Pro Thr Leu Phe
        35                  40                  45

Gly Lys Pro Asp Leu Ser Pro Leu Asp Ala Leu Phe Glu Val Leu Gly
    50                  55                  60

Thr Arg Gln Val Asn Arg Leu Ala Thr Gln Asn Gly Arg Ala Gln Ala
65                  70                  75                  80

Thr Thr Arg Trp Ile Val Thr Leu Leu Pro Lys Gln Ser Gly Tyr Val
                85                  90                  95

Ala Ile Pro Pro Ile Ser Leu Gly Ala Ser Ser Thr Gln Pro Ile Arg
            100                 105                 110

Leu His Val Leu Glu Ala Arg Asp Arg Ala Lys Ser Ser Lys Leu Ala
        115                 120                 125

Pro Val Phe Ile Asp Ala Ser Val Asp Gln Glu Thr Val Tyr Val Gln
    130                 135                 140

Ala Gln Ala Ile Leu Thr Leu Arg Ile Tyr His Ser Val Ser Leu Tyr
145                 150                 155                 160

Asp Asp Ser Ser Leu Thr Pro Leu Ala Met Asn Asp Ala Lys Val Glu
                165                 170                 175

Gln Leu Gly Glu Ala Arg Thr Tyr Glu Lys Glu Ile Asn Gly Ile Arg
            180                 185                 190

His Gly Val Ile Glu Val Arg Tyr Ala Ile Phe Pro Gln Lys Ser Gly
        195                 200                 205

Thr Leu Glu Ile Pro Ala Gln Ala Phe Ser Ala Thr Leu Val Asp Arg
    210                 215                 220

Gly Ser Asp Asp Tyr Asn Pro Phe Gly Pro Arg Pro Gly Arg Gln Met
225                 230                 235                 240

Arg Val Thr Ser Pro Ser Ile Pro Leu Gln Val Arg Pro Lys Pro Ala
                245                 250                 255

Asp Tyr Pro Ala Asp Ala Pro Trp Met Pro Ala Arg Ala Leu Ser Ile
            260                 265                 270

Ser Glu Ser Trp Ser Pro Gln Pro Glu Gln Ala Gln Val Gly Glu Ser
        275                 280                 285

Leu Thr Arg Asn Val Leu Leu Lys Val Glu Gly Leu Ser Gly Thr Gln
    290                 295                 300

Leu Pro Pro Leu Pro Leu Pro Asp Val Gln Gly Leu Arg Arg Tyr Pro
305                 310                 315                 320

Asp Gln Pro Gln Leu Ala Asp Gln Ser Thr Asp Gln Gly Leu Ile Gly
                325                 330                 335

Ser Arg Glu Glu Arg Glu Ala Leu Val Pro Glu Gln Ala Gly Arg Ile
            340                 345                 350

Glu Leu Pro Ala Leu Glu Val Val Trp Trp Asn Thr Arg Glu Asp Arg
        355                 360                 365
```

```
Leu Glu Arg Thr Ser Leu Pro Pro Arg Thr Leu Glu Val Ala Ala Ala
    370                 375                 380

Pro Gln Ala Glu Ala Glu Pro Pro Ala Ala Ala Leu Pro Leu Gly Glu
385                 390                 395                 400

Arg Leu Glu Pro Thr Leu Trp Pro Trp Gln Leu Ala Thr Ala Val Leu
                405                 410                 415

Ala Leu Thr Thr Leu Leu Gly Phe Gly Leu Trp Trp Arg Ala Arg Gln
            420                 425                 430

Leu Pro Ala Val Ile Arg Ala Ala Ala Asn Gly Pro Ser Ser Arg Ser
        435                 440                 445

Leu Leu Asp Glu Leu Arg Arg Ala Cys Leu Ala Asn Asp Pro Gln Ala
    450                 455                 460

Thr Arg Gln Ala Leu Asp Ala Trp Ala Arg Gln Gln Pro Asp Thr Leu
465                 470                 475                 480

Ala Asp Met Ala Ala Arg Phe Val Pro Leu Ser Asp Ala Leu Asp Gly
                485                 490                 495

Leu Asn Gly Ala Leu Tyr Ser Glu Ser Gly His Ser Trp Gln Gly Glu
            500                 505                 510

Asp Leu Trp Arg Ala Ile Arg Ala Leu Pro Thr Thr Glu Gln Ala Pro
        515                 520                 525

Ala Gly Ala Val Asp Asn Gly Gly Leu Pro Pro Leu Tyr Pro Arg
    530                 535                 540


<210> SEQ ID NO 8
<211> LENGTH: 639
<212> TYPE: PRT
<213> ORGANISM: Pseudomonas aeruginosa

<400> SEQUENCE: 8

Met Ser Phe Ser Ser Leu Gly Leu Ser Glu Ala Leu Ala Arg Ala Val
1               5                   10                  15

Glu Ala Ala Gly Tyr Ser Gln Pro Thr Pro Val Gln Gln Arg Ala Ile
            20                  25                  30

Pro Ala Val Leu Gln Gly Arg Asp Leu Met Val Ala Ala Gln Thr Gly
        35                  40                  45

Thr Gly Lys Thr Gly Gly Phe Ala Leu Pro Val Leu Glu Arg Leu Phe
    50                  55                  60

Pro Ala Gly His Pro Asp Arg Glu His Arg His Gly Pro Arg Gln Ala
65                  70                  75                  80

Arg Val Leu Val Leu Thr Pro Thr Arg Glu Leu Ala Ala Gln Val His
                85                  90                  95

Asp Ser Phe Lys Val Tyr Ala Arg Asp Leu Pro Leu Asn Ser Thr Cys
            100                 105                 110

Ile Phe Gly Gly Val Gly Met Asn Pro Gln Ile Gln Ala Leu Ala Lys
        115                 120                 125

Gly Val Asp Val Leu Val Ala Cys Pro Gly Arg Leu Leu Asp Leu Ala
    130                 135                 140

Gly Gln Asn Lys Val Asp Leu Ser His Val Glu Ile Leu Val Leu Asp
145                 150                 155                 160

Glu Ala Asp Arg Met Leu Asp Met Gly Phe Ile His Asp Val Lys Lys
                165                 170                 175

Val Leu Ala Lys Leu Pro Pro Lys Arg Gln Asn Leu Leu Phe Ser Ala
            180                 185                 190

Thr Phe Ser Lys Asp Ile Val Asp Leu Ala Asn Lys Leu Leu His Asn
```

-continued

```
        195                 200                 205

Pro Glu Arg Ile Glu Val Thr Pro Pro Asn Thr Thr Val Glu Arg Ile
    210                 215                 220

Glu Gln Arg Val Phe Arg Leu Pro Ala Pro Gln Lys Arg Ala Leu Leu
225                 230                 235                 240

Ala His Leu Val Thr Val Gly Ala Trp Glu Gln Val Leu Val Phe Thr
                245                 250                 255

Arg Thr Lys His Gly Ala Asn Arg Leu Ala Glu Tyr Leu Thr Lys His
            260                 265                 270

Gly Leu Pro Ala Ala Ala Ile His Gly Asn Lys Ser Gln Asn Ala Arg
        275                 280                 285

Thr Lys Ala Leu Ala Asp Phe Lys Ala Asn Asp Val Arg Ile Leu Val
    290                 295                 300

Ala Thr Asp Ile Ala Ala Arg Gly Leu Asp Ile Asp Gln Leu Pro His
305                 310                 315                 320

Val Val Asn Tyr Glu Leu Pro Asn Val Glu Glu Asp Tyr Val His Arg
                325                 330                 335

Ile Gly Arg Thr Gly Arg Ala Gly Arg Ser Gly Glu Ala Ile Ser Leu
            340                 345                 350

Val Ala Pro Asp Glu Glu Lys Leu Leu Lys Ala Ile Glu Lys Met Thr
        355                 360                 365

Arg Gln Arg Ile Pro Asp Gly Asp Ala Gln Gly Phe Asp Pro Glu Ala
    370                 375                 380

Val Leu Pro Glu Val Ala Gln Pro Glu Pro Arg Glu Ala Pro Gln Lys
385                 390                 395                 400

Gln Pro Arg Arg Asp Lys Glu Arg Arg Ser Ser Arg Glu Arg Lys Pro
                405                 410                 415

Lys Asp Ala Gln Ala Ser Asn Pro Asp Ser Asn Val Ala Ala Ala Gln
            420                 425                 430

Asp Gly Thr Glu Lys Pro Ala Gly Lys Arg Arg Arg Arg Gly Gly Lys
        435                 440                 445

Asn Lys Glu Asn Arg Glu Ala Gly Gln Ala Gln Gln Pro Arg Gln Ser
    450                 455                 460

Arg Glu Ala Arg Pro Ala Lys Pro Asn Arg Pro Pro Glu Val Asp Gly
465                 470                 475                 480

Asn Arg Asp Pro Glu Glu Phe Leu Asp Asp Asp Phe Asp Asn Phe Gly
                485                 490                 495

Asn Arg Ala Asp Tyr Val Ser Pro Tyr Gln Gly Gln Glu Asn Lys Gly
            500                 505                 510

Arg Gly Arg Arg Gly Gly Gln Gln Lys Pro Gln Gly Gly Thr Gly Gln
        515                 520                 525

Gln Gly Arg Gly Gln Gly Gln Gly Gln Ala Arg Gly Lys Ser Gln Gly
    530                 535                 540

Ala Ala Gln Gly Gly Ala Arg Gly Gln Gly Ala Gly Gln Gly Lys Ala
545                 550                 555                 560

Lys Lys Pro Arg Ala Gly Lys Pro Arg Gly Gln Gly Arg Glu Asn Ala
                565                 570                 575

Ser Arg Met Ser Asp Ala Pro Leu Arg Glu Pro Ser Glu Tyr Gly Thr
            580                 585                 590

Gly Lys Gln Pro Ser Arg Gln Pro Val Val Ile Asn Lys Arg Asp Leu
        595                 600                 605

Val Arg Met Asp Arg Phe Pro Thr Ala Glu Gln Leu Asp Glu Leu Glu
    610                 615                 620
```

```
Pro Arg Arg Lys Gly Glu Arg Pro Ala Leu Leu Thr Arg Asn Arg
625                 630                 635


<210> SEQ ID NO 9
<211> LENGTH: 675
<212> TYPE: PRT
<213> ORGANISM: Pseudomonas aeruginosa

<400> SEQUENCE: 9

Met Pro Ala Ser Phe Pro Arg Leu Gly Leu Leu Gly Ala Leu Cys Ser
1               5                   10                  15

Ile Val Pro Leu Leu His Ala Ser Glu Pro Thr Thr Asp Ala Ala Leu
            20                  25                  30

Ile Glu Lys Gly Arg Tyr Val Ala Gln Leu Gly Asp Cys Ile Ala Cys
        35                  40                  45

His Thr Gly Pro Gln Gly Ala Pro Met Ala Gly Gly Leu Glu Leu Lys
    50                  55                  60

Thr Pro Met Gly Thr Ile Tyr Ser Thr Asn Ile Thr Pro Asp Arg Glu
65                  70                  75                  80

Thr Gly Ile Gly Arg Tyr Ser Phe Glu Glu Phe Asp Arg Ala Met Arg
                85                  90                  95

Lys Gly Val Thr Ala Glu Gly Val Asn Leu Tyr Pro Ala Met Pro Tyr
            100                 105                 110

Pro Ser Tyr Ala Lys Ile Ser Glu Glu Asp Met Arg Ala Leu Tyr Ala
        115                 120                 125

Tyr Leu Met His Gly Val Gln Pro Val Thr Gln Ala Asn Thr Pro Ser
    130                 135                 140

Ala Met Ser Trp Pro Phe Asn Gln Arg Trp Gly Leu Ser Leu Trp Asn
145                 150                 155                 160

Trp Ala Phe Leu Asp Asp Ala Pro Phe Thr Pro Ser Ser Asp Ala Asp
                165                 170                 175

Pro Val Ile Asn Arg Gly Ala Tyr Leu Val Gln Gly Leu Gly His Cys
            180                 185                 190

Gly Ala Cys His Thr Pro Arg Gly Ile Ala Phe Gln Glu Lys Ala Met
        195                 200                 205

Ser Glu Ala Gly Arg Ser Gly Gln Phe Tyr Leu Ala Gly Glu Thr Val
    210                 215                 220

Glu Gln Trp Gln Ala Leu Ser Leu Arg Asn Leu Trp Thr Val Glu Asp
225                 230                 235                 240

Thr Val Gln Leu Leu Lys Thr Gly Gln Asn Arg Phe Ala Thr Val Ser
                245                 250                 255

Gly Ser Met Thr Asp Val Ile His His Ser Thr Gln His Phe Ser Asp
            260                 265                 270

Asp Asp Leu Leu Ala Ile Ala Ser Tyr Leu Lys Ser Leu Pro Ala Gly
        275                 280                 285

Lys Asp Asp Leu Pro Met Pro Asp Ser Glu Arg Pro Leu Ala Ala Pro
    290                 295                 300

Val Asp Leu Tyr Ser Ser Arg Gly Gly Leu Gly Tyr Ala Gln Phe Cys
305                 310                 315                 320

Ser Asp Cys His Arg Lys Asp Gly Ser Gly Val Pro Gly Met Phe Pro
                325                 330                 335

Pro Leu Ala Gly Asn Pro Thr Val Ala Ser Ala Asn Pro Ser Thr Leu
            340                 345                 350

Leu His Ile Thr Leu Thr Gly Trp Lys Thr Ala Gln Thr Ala Thr His
```

```
        355                 360                 365

Ser Arg Val Tyr Thr Met Pro Gly Phe Ala Gln Leu Glu Asp Arg Glu
    370                 375                 380

Ile Ala Glu Ile Leu Ser Phe Val Arg Ser Ser Trp Gly Asn Gln Gly
385                 390                 395                 400

Ser Ser Ile Asp Ala Gly Gln Val Lys Lys Leu Arg Gln Arg Ile Glu
                405                 410                 415

Ala Gly Asn Gly Pro Ala Thr Thr Phe Val Ser Pro Arg Leu Ala Asp
            420                 425                 430

Met Leu Ala Ala Pro Asn Ala Glu Gln Val Val Arg Gly Met Arg Leu
        435                 440                 445

His Leu Glu Thr Arg Glu Leu Leu Pro Ala Asn Val Gly Asn Gln Leu
    450                 455                 460

His Cys Thr Ser Cys His Leu Asn Ala Gly Thr Val Ala Asp Gly Ser
465                 470                 475                 480

Pro Phe Val Gly Val Ser Ala Phe Phe Pro Ser Tyr Ala Pro Arg Ala
                485                 490                 495

Gly Lys Val Ile Gly Leu Glu Glu Arg Ile Asn Gly Cys Phe Arg Arg
            500                 505                 510

Ser Met Asn Gly Lys Pro Leu Pro Pro Asp Ser Ala Asp Met Gln Ala
        515                 520                 525

Met Val Ala Tyr Phe Asp Trp Met Lys Asn Asn Thr Arg Pro Gln Asp
    530                 535                 540

Lys Val Ala Gly Arg Gly Val Gly Lys Val Asp Pro Ala Leu Lys Pro
545                 550                 555                 560

Asp Pro Glu Asn Gly Arg Lys Val Tyr Ala Arg Gln Cys Val Val Cys
                565                 570                 575

His Gly Glu Asn Gly Glu Gly Leu Arg Asn Ser Ala Gly Glu Met Leu
            580                 585                 590

Phe Pro Pro Leu Trp Gly Asp Glu Ser Phe Asn Ile Gly Ala Gly Met
        595                 600                 605

Ala Arg Thr Phe Thr Ala Ala Ala Phe Val Lys His Asn Met Pro Ile
    610                 615                 620

Gly Phe Gln Glu Arg Phe Pro Leu Gly Gln Gly Gly Leu Ser Asp Gln
625                 630                 635                 640

Asp Ala Val Asp Val Ala Glu Tyr Phe Ser His Gln Pro Arg Pro Asp
                645                 650                 655

Phe Pro Asp Lys Ile Lys Asp Trp Pro Lys Asp Lys Arg Pro Leu Asp
            660                 665                 670

Ala Arg Tyr
        675


<210> SEQ ID NO 10
<211> LENGTH: 682
<212> TYPE: PRT
<213> ORGANISM: Pseudomonas aeruginosa

<400> SEQUENCE: 10

Met Pro Gly Lys Ala Leu Arg Val Met Leu Cys Ala Trp Ser Cys Leu
1               5                   10                  15

Leu Ala Gly Gln Ala Ser Ala Leu Gly Val Gly Asp Ile Ile Leu His
            20                  25                  30

Ser Ala Leu Asn Gln Pro Leu Asp Ala Asp Ile Glu Leu Leu Asp Val
        35                  40                  45
```

-continued

```
Gly Asp Leu Gly Ala Asp Glu Ile Glu Val Arg Leu Ala Gly Ala Asp
    50                  55                  60

Val Phe Ala Ala Ala Gly Val Glu Arg Leu Gln Phe Leu Asn Glu Leu
65                  70                  75                  80

Arg Phe Ser Pro Val Leu Gln Gly Arg Gly Gly Asn Arg Ile His Val
                85                  90                  95

Ser Ser Ile Arg Pro Val Gln Glu Pro Tyr Leu Asn Phe Leu Val Glu
            100                 105                 110

Val Ala Arg Pro Asn Gly Arg Ile Val Arg Glu Phe Thr Val Leu Leu
        115                 120                 125

Asp Pro Leu Gly Tyr Thr Pro Arg Met Leu Pro Ala Ala Arg Ser Gly
    130                 135                 140

Ile Glu Pro Gln Arg Gln Ser Ser Thr Pro Val Pro Ala Pro Arg Ser
145                 150                 155                 160

Ala Ala Val Val Val Asp Pro Ala Leu Leu Glu Pro Gly Asp Glu Tyr
                165                 170                 175

Leu Ala Arg Pro Ser Asp Asn Leu Trp Ala Ile Ser Gly Arg Leu Arg
            180                 185                 190

Gly Ala Gly Asn Ala Asp Arg Ala Gln Leu Met Glu Ala Leu Tyr Gln
        195                 200                 205

Leu Asn Pro Gln Ala Phe Val Asn Ala Asp Arg His Arg Leu Lys Ala
    210                 215                 220

Gly Ala Arg Leu Arg Leu Pro Ala Gly Tyr Gln Pro Glu Arg Gly Ala
225                 230                 235                 240

Pro Gly Ala Val Lys Glu Ala Ala Val Glu Val Leu Pro Pro Ala Asp
                245                 250                 255

Ala Ala Val Val Glu Asn Ala Pro Ala Ala Leu Val Glu Ala Gln Arg
            260                 265                 270

Gln Ala Asp Ala Glu Ala Glu Ala Leu Ala Arg Gln Arg Glu Glu Leu
        275                 280                 285

Ser Gln Arg Met Asp Asp Leu Gln Arg Gln Leu Gln Ala Leu Gln Glu
    290                 295                 300

Gln Leu Gln Gln Arg Asp His Gln Val Ala Glu Leu Gln Gln Gln Leu
305                 310                 315                 320

Ala Arg Arg Gln Ala Val Arg Pro Ala Ala Pro Pro Pro Ala Ala Ala
                325                 330                 335

Ala Pro Ser Val Ala Gln Pro Val Glu Thr Pro Thr Asp Ser Gln Tyr
            340                 345                 350

Trp Arg Trp Met Ile Val Leu Leu Leu Val Leu Ala Leu Leu Gly Val
        355                 360                 365

Leu Leu Leu Arg Arg Arg Arg Glu Glu Ala Pro Val Pro Ala Val Glu
    370                 375                 380

Pro Lys Arg Arg Val Ala Leu Asn Leu Pro Leu Arg Arg Ala Pro Arg
385                 390                 395                 400

Pro Pro Ala Ala Ala Pro Ala Pro Ala Lys Val Glu Glu Gln Ala Arg
                405                 410                 415

Pro Pro Val Ala Ala Pro Ser Ser Pro Pro Pro Ser Pro Pro Pro Ala
            420                 425                 430

Pro Ala Ala Ala Pro Arg Ala Ala Met Ala Ala Ala Asp Lys Leu Asp
        435                 440                 445

Gly Ala Asp Ile Tyr Ile Ala Tyr Gly Arg Tyr Gly Gln Ala Arg Asp
    450                 455                 460

Leu Leu Arg Gln Val Leu Ala Glu Gln Pro Gln Arg Leu Ser Ala Arg
```

```
465                 470                 475                 480

Met Lys Leu Leu Leu Val Leu Ala Glu Leu Gly Asp Ala Ala Gly Phe
                485                 490                 495

Asp Ala Leu Ala Glu Glu Thr Leu Ala Ser Gly Gly Asn Pro Glu Ala
            500                 505                 510

Ile Asp Glu Leu Arg Gly Arg Tyr Pro Ala Leu Leu Gln Met Pro Ala
        515                 520                 525

Thr Glu Thr Pro Ala Ala Thr Thr Lys Asp Asp Asp Trp Ser Asp Leu
    530                 535                 540

Pro Leu Ala Glu Ser Pro Val Leu Gln Gln Pro Asp Ala Thr Ser Gly
545                 550                 555                 560

Ala Asp Gly Phe Gly Asp Leu Asn Leu Asp Leu Asp Leu Asp Trp Gly
                565                 570                 575

Ala Leu Glu Asn Pro Leu Asp Asn Pro Asp Leu Pro Arg Arg Ala Ala
            580                 585                 590

Ala Gly Lys Ala Glu Pro Ala Glu Glu Pro Leu Ala Phe Glu Ser Asn
        595                 600                 605

Leu His Glu Leu Pro Asp Val Ala Glu Tyr Glu His Leu Glu Leu Asp
    610                 615                 620

Gln Pro Glu Pro Ala Thr Val Pro Pro Glu Glu Ala Ser Ala Ser Leu
625                 630                 635                 640

Asp Arg Ala Arg Ala Cys Ile Asp Ser Gly Asp Leu Asp Gln Ala Ser
                645                 650                 655

Arg Ile Leu Arg Leu Val Val Ala His Gly Asp Pro Trp Gln Lys Ala
            660                 665                 670

Glu Ala Arg Glu Leu Leu Ala Leu Ile Ala
        675                 680


<210> SEQ ID NO 11
<211> LENGTH: 687
<212> TYPE: PRT
<213> ORGANISM: Pseudomonas aeruginosa

<400> SEQUENCE: 11

Met Ser Ser Ser Gly Leu Phe Pro Ser Arg Pro Leu Trp Pro Leu Thr
1               5                   10                  15

Pro Leu Ala Leu Ala Cys Leu Ile Val Ser Gly Glu Thr Leu Gly Ala
            20                  25                  30

Asp Gly Arg Pro Ser Glu Leu Pro Ser Gln Val Ile Thr Ala Asn Pro
        35                  40                  45

Leu Gly Asn Glu Ser Pro Ala Thr Pro Ser Ser Val Leu Glu Gly Asp
    50                  55                  60

Glu Leu Thr Leu Arg Gln Lys Gly Ser Leu Gly Glu Thr Leu Asn Gly
65                  70                  75                  80

Leu Pro Gly Val Ser Ser Thr Tyr Phe Gly Pro Gly Ala Ser Arg Pro
                85                  90                  95

Val Ile Arg Gly Met Asp Gly Asp Arg Ile Arg Leu Leu Arg Asn Gly
            100                 105                 110

Val Gly Ala Leu Asp Ala Ser Ser Leu Ser Tyr Asp His Ala Val Pro
        115                 120                 125

Glu Asp Pro Asn Ser Val Glu Arg Leu Glu Val Val Arg Gly Pro Ala
    130                 135                 140

Ala Leu Leu Tyr Gly Gly Asn Ala Ile Gly Gly Val Val Asn Ser Phe
145                 150                 155                 160
```

-continued

```
Asp Asn Arg Ile Pro Ser Glu Pro Val Asp Gly Ile His Gly Ser Gly
            165                 170                 175

Glu Leu Arg Tyr Gly Gly Ala Asp Thr Thr Arg Ser Arg Ser Gly Ala
            180                 185                 190

Leu Glu Ala Gly Asp Gly Asn Phe Ala Leu His Val Asp Ala Ala Ser
        195                 200                 205

Arg Glu Phe Asn Asp Val Arg Ile Pro Gly Tyr Ala His Ser Ser Arg
    210                 215                 220

Gln Arg Gln Ile Asp Gly Asp Thr Gly Lys His Arg Val Gln Asn Ser
225                 230                 235                 240

Asp Gly Arg Gln Asp Gly Gly Ala Val Gly Gly Ser Tyr His Trp Glu
                245                 250                 255

His Gly Tyr Ala Gly Leu Ser Tyr Ser Gly Tyr Asp Ser Asn Tyr Gly
            260                 265                 270

Ser Pro Ala Glu Asp Asp Val Arg Leu Lys Met Gln Gln Asp Arg Tyr
        275                 280                 285

Ala Phe Ala Ser Glu Ile Arg Asp Leu Glu Gly Pro Phe Thr Ser Leu
    290                 295                 300

Lys Leu Asp Ala Ala Tyr Thr Lys Tyr Glu His Lys Glu Ile Glu Asp
305                 310                 315                 320

Gly Glu Thr Gly Thr Thr Phe Lys Asn Glu Gly Tyr Glu Gly Arg Ile
                325                 330                 335

Glu Ala Arg His Arg Pro Leu Gly Pro Leu Asn Gly Val Val Gly Ala
            340                 345                 350

Gln Phe Ala Asn Ser Arg Phe Ser Ala Leu Gly Glu Glu Ala Phe Val
        355                 360                 365

Pro His Thr Glu Thr Asp Ser Ala Ala Leu Phe Ala Leu Glu Glu Trp
    370                 375                 380

Lys Leu Ser Asp Arg Leu Asp Leu Ser Phe Gly Ala Arg Leu Glu His
385                 390                 395                 400

Thr Arg Val Asp Pro Asp Ala Lys Gly Asn Glu Arg Phe Ala Glu Asn
                405                 410                 415

Asp Gly Ser Gln Ser Phe Thr Thr Gly Ser Leu Ser Thr Gly Ala Val
            420                 425                 430

Tyr Lys Leu Thr Pro Ile Trp Ser Leu Ala Ala Thr Leu Ser Tyr Thr
        435                 440                 445

Glu Arg Ala Pro Thr Phe Tyr Glu Leu Tyr Ala Asn Gly Pro His Ala
    450                 455                 460

Ala Thr Gly Thr Tyr Glu Val Gly Asp Ala Asp Ala Asp Lys Glu Lys
465                 470                 475                 480

Ala Val Ser Thr Asp Leu Ala Leu Arg Phe Asp Asn Gly Val His Lys
                485                 490                 495

Gly Ser Val Gly Val Phe Tyr Ser Arg Phe Ser Asn Tyr Ile Gly Leu
            500                 505                 510

Leu Ala Ser Gly Arg His Arg Asn Glu Glu Gly Glu Val Val Ala Ala
        515                 520                 525

Gly Asp Asp Glu Ala Leu Pro Glu Tyr Leu Tyr Ser Gly Val Arg Ala
    530                 535                 540

Asp Phe Tyr Gly Val Glu Ala Gln Asp Arg Ile His Leu Leu Glu Ser
545                 550                 555                 560

Pro Tyr Gly Asn Phe Asp Leu Glu Leu Ser Gly Asp Tyr Thr Arg Ala
                565                 570                 575

Lys Asn Lys Asp Thr Gly Glu Pro Leu Pro Arg Ile Ala Pro Leu Arg
```

```
            580                 585                 590

Leu Asn Thr Ala Leu Ile Trp Glu Leu Gln Gln Trp Gln Ala Arg Val
        595                 600                 605

Asp Val Glu His Ala Ala Ser Gln His Arg Val Pro Glu Glu Glu Leu
    610                 615                 620

Ser Thr Asp Gly Tyr Thr Thr Leu Gly Ala Ser Leu Gly Tyr Asn Phe
625                 630                 635                 640

Asp Leu Gly Glu Ser Arg Trp Leu Ala Phe Val Lys Gly Thr Asn Leu
                645                 650                 655

Thr Asn Gln Thr Val Arg Tyr Ala Ser Ser Ile Leu Arg Asp Arg Val
            660                 665                 670

Pro Ala Ala Gly Arg Gly Ile Glu Ala Gly Val Lys Val Ala Phe
        675                 680                 685


<210> SEQ ID NO 12
<211> LENGTH: 803
<212> TYPE: PRT
<213> ORGANISM: Pseudomonas aeruginosa

<400> SEQUENCE: 12

Met Arg Gln Ser Ala Phe His His Ala Arg Arg Arg Trp Pro Val Leu
1               5                   10                  15

Gly Val Ala Leu Gly Ala Leu Leu Val Ala Ala Cys Ser Glu Thr Pro
            20                  25                  30

Lys Val Pro Gly Val Pro Pro Ala Asp Glu Glu Val Gly Arg Pro Leu
        35                  40                  45

Ser Ser Val Arg Ser Gly Ala Pro Leu Arg Ser Ala Asp Val Arg Glu
    50                  55                  60

Arg Pro Gln Ala Glu Gln Ala Arg Arg Ala Leu Ser Ala Gly Arg Gly
65                  70                  75                  80

Val Ala Arg Ser Gly Gly Val Ala Pro Val Ser Ala Thr Ala Ala Glu
                85                  90                  95

Leu Gly Glu Gln Pro Val Ser Leu Asn Phe Val Asp Thr Glu Val Glu
            100                 105                 110

Ala Val Val Arg Ala Leu Ser Arg Ala Thr Gly Arg Gln Phe Leu Val
        115                 120                 125

Asp Pro Arg Val Lys Gly Lys Leu Thr Leu Val Ser Glu Gly Gln Val
    130                 135                 140

Pro Ala Arg Thr Ala Tyr Arg Met Leu Thr Ser Ala Leu Arg Met Gln
145                 150                 155                 160

Gly Phe Ser Val Val Asp Val Asp Gly Val Ser Gln Val Val Pro Glu
                165                 170                 175

Ala Asp Ala Lys Leu Leu Gly Gly Pro Val Tyr Gly Ala Asp Arg Pro
            180                 185                 190

Ala Ala Asn Gly Met Val Thr Arg Thr Phe Arg Leu Arg Tyr Glu Asn
        195                 200                 205

Ala Val Asn Leu Ile Pro Val Leu Arg Pro Ile Val Ala Gln Asn Asn
    210                 215                 220

Pro Ile Asn Ala Tyr Pro Gly Asn Asn Thr Val Val Val Thr Asp Tyr
225                 230                 235                 240

Ala Glu Asn Leu Asp Arg Val Ala Gly Ile Ile Ala Ser Ile Asp Ile
                245                 250                 255

Pro Ser Ala Ser Asp Thr Asp Val Val Pro Ile Gln Asn Gly Ile Ala
            260                 265                 270
```

-continued

```
Val Asp Ile Ala Ser Thr Val Ser Glu Leu Leu Asp Ser Gln Gly Ser
        275                 280                 285

Gly Gly Ala Glu Gln Gly Gln Lys Thr Val Val Leu Ala Asp Pro Arg
    290                 295                 300

Ser Asn Ser Ile Val Ile Arg Ser Pro Ser Pro Glu Arg Thr Gln Leu
305                 310                 315                 320

Ala Arg Asp Leu Ile Gly Lys Leu Asp Ser Val Gln Ser Asn Pro Gly
                325                 330                 335

Asn Leu His Val Val Tyr Leu Arg Asn Ala Gln Ala Thr Arg Leu Ala
            340                 345                 350

Gln Ala Leu Arg Gly Leu Ile Thr Gly Asp Ser Gly Gly Glu Gly Asn
        355                 360                 365

Glu Gly Asp Gln Gln Arg Ala Arg Leu Ser Gly Gly Gly Met Leu Gly
    370                 375                 380

Gly Gly Asn Ser Gly Thr Gly Ser Gln Gly Leu Gly Ser Ser Gly Asn
385                 390                 395                 400

Thr Thr Gly Ser Gly Ser Ser Gly Leu Gly Gly Ser Asn Arg Ser Gly
                405                 410                 415

Gly Ala Tyr Gly Ala Met Gly Ser Gly Gln Gly Gly Ala Gly Pro Gly
            420                 425                 430

Ala Met Gly Glu Glu Asn Ser Ala Phe Ser Ala Gly Gly Val Thr Val
        435                 440                 445

Gln Ala Asp Ala Thr Thr Asn Thr Leu Leu Ile Ser Ala Pro Glu Pro
    450                 455                 460

Leu Tyr Arg Asn Leu Arg Glu Val Ile Asp Leu Leu Asp Gln Arg Arg
465                 470                 475                 480

Ala Gln Val Val Ile Glu Ser Leu Ile Val Glu Val Ser Glu Asp Asp
                485                 490                 495

Ser Ser Glu Phe Gly Ile Gln Trp Gln Ala Gly Asn Leu Gly Gly Asn
            500                 505                 510

Gly Val Phe Gly Gly Val Asn Phe Gly Gln Ser Ala Leu Asn Thr Ala
        515                 520                 525

Gly Lys Asn Thr Ile Asp Val Leu Pro Lys Gly Leu Asn Ile Gly Leu
    530                 535                 540

Val Asp Gly Thr Val Asp Ile Pro Gly Ile Gly Lys Ile Leu Asp Leu
545                 550                 555                 560

Lys Val Leu Ala Arg Ala Leu Lys Ser Arg Gly Gly Thr Asn Val Leu
                565                 570                 575

Ser Thr Pro Asn Leu Leu Thr Leu Asp Asn Glu Ser Ala Ser Ile Met
            580                 585                 590

Val Gly Gln Thr Ile Pro Phe Val Ser Gly Gln Tyr Val Thr Asp Gly
        595                 600                 605

Gly Gly Thr Ser Asn Asn Pro Phe Gln Thr Ile Gln Arg Glu Asp Val
    610                 615                 620

Gly Leu Lys Leu Asn Ile Arg Pro Gln Ile Ser Glu Gly Gly Thr Val
625                 630                 635                 640

Lys Leu Asp Val Tyr Gln Glu Val Ser Ser Val Asp Glu Arg Ala Ser
                645                 650                 655

Thr Ala Ala Gly Val Val Thr Asn Lys Arg Ala Ile Asp Thr Ser Ile
            660                 665                 670

Leu Leu Asp Asp Gly Gln Ile Met Val Leu Gly Gly Leu Leu Gln Asp
        675                 680                 685

Asn Val Gln Asp Asn Thr Asp Gly Val Pro Gly Leu Ser Ser Leu Pro
```

```
    690                 695                 700

Gly Val Gly Ser Leu Phe Arg Tyr Gln Lys Arg Ser Arg Thr Lys Thr
705                 710                 715                 720

Asn Leu Met Val Phe Leu Arg Pro Tyr Ile Val Arg Asp Ala Ala Ala
                725                 730                 735

Gly Arg Ser Ile Thr Leu Asn Arg Tyr Asp Phe Ile Arg Arg Ala Gln
            740                 745                 750

Gln Arg Val Gln Pro Arg His Asp Trp Ser Val Gly Asp Met Gln Ala
        755                 760                 765

Pro Val Leu Pro Pro Ala Gln Gln Gly Ile Pro Gln Ala Ala Tyr Asp
    770                 775                 780

Leu Arg Pro Ser Pro Arg Pro Leu Arg Ala Val Pro Leu Gly Glu Ala
785                 790                 795                 800

Ala Pro Leu


<210> SEQ ID NO 13
<211> LENGTH: 1162
<212> TYPE: PRT
<213> ORGANISM: Pseudomonas aeruginosa

<400> SEQUENCE: 13

Met Arg Leu Lys Ser Ile Lys Leu Ala Gly Phe Lys Ser Phe Val Asp
1               5                   10                  15

Pro Thr Thr Val Asn Phe Pro Ser Asn Met Ala Ala Val Val Gly Pro
            20                  25                  30

Asn Gly Cys Gly Lys Ser Asn Ile Ile Asp Ala Val Arg Trp Val Met
        35                  40                  45

Gly Glu Ser Ser Ala Lys Asn Leu Arg Gly Glu Ser Met Thr Asp Val
    50                  55                  60

Ile Phe Asn Gly Ser Asn Thr Arg Lys Pro Val Ser Gln Ala Ser Ile
65                  70                  75                  80

Glu Leu Ile Phe Asp Asn Ala Glu Thr Thr Leu Val Gly Glu Tyr Ala
                85                  90                  95

Gln Tyr Ala Glu Ile Ser Ile Arg Arg Arg Val Ser Arg Asp Gly Gln
            100                 105                 110

Asn Thr Tyr Phe Leu Asn Gly Thr Lys Cys Arg Arg Arg Asp Ile Thr
        115                 120                 125

Asp Ile Phe Leu Gly Thr Gly Leu Gly Pro Arg Ser Tyr Ser Ile Ile
    130                 135                 140

Glu Gln Gly Met Ile Ser Lys Leu Ile Glu Ala Arg Pro Glu Asp Leu
145                 150                 155                 160

Arg Asn Phe Ile Glu Glu Ala Ala Gly Ile Ser Lys Tyr Lys Glu Arg
                165                 170                 175

Arg Arg Glu Thr Glu Ser Arg Ile Arg Arg Thr Gln Glu Asn Leu Ala
            180                 185                 190

Arg Leu Thr Asp Leu Arg Glu Glu Leu Gly Arg Gln Leu Glu Arg Leu
        195                 200                 205

His Arg Gln Ala Gln Ser Ala Glu Lys Tyr Gln Glu His Lys Ala Glu
    210                 215                 220

Glu Arg Gln Leu Lys Ala Gln Leu Gly Ala Val Arg Trp Arg Asp Leu
225                 230                 235                 240

Asn Glu Gln Val Gly Gln Arg Glu Arg Val Ile Gly Asp Gln Glu Ile
                245                 250                 255

Ala Phe Glu Ala Leu Val Ala Glu Gln Arg Gly Ala Asp Ala Gly Ile
```

```
            260                 265                 270

Glu Arg Leu Arg Asp Gly His His Glu Leu Ser Glu Arg Phe Asn Gln
        275                 280                 285

Val Gln Ala Arg Phe Tyr Ser Val Gly Gly Asp Ile Ala Arg Val Glu
    290                 295                 300

Gln Ser Ile Gln His Gly Gln Gln Arg Gln Arg Gln Leu Gln Asp Asp
305                 310                 315                 320

Leu Arg Glu Ala Glu Arg Thr Arg Gln Glu Thr Glu Ser His Leu Gly
                325                 330                 335

His Asp Arg Thr Leu Leu Ala Thr Leu Ala Glu Glu Met Ala Met Leu
            340                 345                 350

Ala Pro Glu Gln Glu Leu Ser Ala Ala Ala Ala Glu Glu Ala Gly Ile
        355                 360                 365

Ala Leu Glu Gln Ala Glu Gln Gly Met Gln Ala Trp Gln Gln Gln Trp
    370                 375                 380

Asp Ala Phe Asn Gln Gln Ser Ala Glu Pro Arg Arg Gln Ala Glu Val
385                 390                 395                 400

Gln Gln Ser Arg Ile Gln His Leu Glu Gln Ser Leu Glu Arg Leu Gln
                405                 410                 415

Asp Arg Glu Arg Arg Leu Gln Glu Glu Arg Gly Gln Leu Ala Ala Asp
            420                 425                 430

Pro Glu Asp Ala Ala Ile Leu Glu Leu Asn Glu Gln Val Ala Ile Ala
        435                 440                 445

Glu Leu Ala Leu Glu Glu Leu Gln Leu Gln Glu Gln Gly Gln Ala Glu
    450                 455                 460

Arg Leu Glu Gln Leu Arg Gln Glu Leu Gln Gln Leu Ala Ala Glu Gln
465                 470                 475                 480

His Gln Ala Gln Gly Glu Leu Gln Arg Leu Asn Gly Arg Ile Ala Ser
                485                 490                 495

Leu Glu Ala Leu Gln Gln Ala Ala Leu Asp Pro Gly Gln Gly Ala Leu
            500                 505                 510

Glu Trp Leu Arg Glu Gln Gly Leu Glu Gln Arg Pro Arg Leu Ala Glu
        515                 520                 525

Gly Leu Arg Val Glu Pro Gly Trp Glu Leu Ala Val Glu Thr Val Leu
    530                 535                 540

Gly Ala Asp Leu Gln Ala Val Leu Leu Asp Gly Phe Asp Gly Leu Ala
545                 550                 555                 560

Leu Ala Gly Phe Gly Lys Gly Glu Leu Arg Leu Leu Ser Pro Ala Arg
                565                 570                 575

Gly Ala Ala Thr Ala Ala Gly Ser Leu Leu Asp Lys Val Arg Ala Asp
            580                 585                 590

Ala Asp Leu Ser Pro Trp Leu Ala Arg Val Lys Pro Val Glu Thr Leu
        595                 600                 605

Glu Gln Ala Leu Ala Gln Arg Gly Ala Leu Asp Asp Gly Glu Ser Leu
    610                 615                 620

Ile Ser Arg Asp Gly Tyr Trp Val Gly Arg His Phe Leu Arg Val Arg
625                 630                 635                 640

Arg Ser Asp Glu Ala Gln Gly Gly Met Leu Ala Arg Ala Gln Glu Leu
                645                 650                 655

Glu Ala Leu Gln Glu Arg Arg Glu Ala Leu Glu Thr Arg Val Ala Glu
            660                 665                 670

Gly Glu Glu Arg Leu Ala Ala Ala Arg Asp Glu Gln Arg Glu Leu Glu
        675                 680                 685
```

```
Gly Ala Arg Glu Gln Val Arg Arg Gln Val Gln Glu Glu Gly Arg Arg
    690                 695                 700

His Gly Glu Leu Lys Ala Gln Leu Ser Ala Gln Gln Ala Lys Val Glu
705                 710                 715                 720

Gln Leu Val Leu Arg Arg Arg Arg Leu Asp Glu Glu Val Ala Glu Leu
                725                 730                 735

Ala Glu Gln Arg Ala Leu Glu Gln Glu Gln Leu Ser Glu Ala Arg Leu
            740                 745                 750

Thr Leu Gln Glu Ala Leu Asp Ser Met Ala Leu Asp Thr Glu Arg Arg
        755                 760                 765

Glu Ser Leu Leu Ala Glu Arg Asp Ala Leu Arg Glu Arg Leu Asp Arg
    770                 775                 780

Ile Arg Gln Asp Ala Arg Thr His Lys Asp His Ala His Gln Leu Ala
785                 790                 795                 800

Val Arg Val Gly Ser Leu Lys Ala Gln His Asn Ser Thr Gln Gln Ala
                805                 810                 815

Leu Glu Arg Leu Asp Gln Gln Ser Ala Arg Leu Asn Glu Arg Cys Glu
            820                 825                 830

Gln Leu Asn Leu Asn Leu Glu Glu Gly Ala Ala Pro Leu Glu Glu Leu
        835                 840                 845

Arg Met Lys Leu Glu Glu Leu Leu Glu Arg Arg Met Ala Val Glu Asp
    850                 855                 860

Glu Leu Lys Gln Ala Arg Leu Ala Leu Glu Asp Ala Asp Arg Glu Leu
865                 870                 875                 880

Arg Glu Val Glu Lys Arg Arg Gly Gln Ala Glu Gln Gln Ser Gln Leu
                885                 890                 895

Leu Arg Gly Gln Leu Glu Gln Gln Arg Leu Glu Trp Gln Gly Leu Val
            900                 905                 910

Val Arg Arg Lys Ala Leu Gln Glu Gln Leu Ala Glu Asp Gly Tyr Asp
        915                 920                 925

Leu His Thr Val Leu Ala Asn Leu Pro Leu Asp Ala Ser Glu Arg Asp
    930                 935                 940

Trp Glu Glu Arg Leu Glu Ser Leu Ala Ala Arg Ile Gln Arg Leu Gly
945                 950                 955                 960

Pro Ile Asn Leu Ala Ala Ile Glu Glu Tyr Gln Gln Gln Ser Glu Arg
                965                 970                 975

Lys Arg Tyr Leu Asp Ser Gln Asn Asp Asp Leu Ala Glu Ala Leu Glu
            980                 985                 990

Thr Leu Glu Asn Val Ile Arg Lys  Ile Asp Arg Glu Thr  Arg Asn Arg
        995                 1000                1005

Phe Lys  Glu Thr Phe Asp Gln  Ile Asn Ala Gly Leu  Gln Ala Leu
    1010                1015                1020

Phe Pro  Lys Val Phe Gly Gly  Gly Thr Ala Tyr Leu  Glu Leu Thr
    1025                1030                1035

Gly Glu  Asp Leu Leu Asp Thr  Gly Val Ala Ile Met  Ala Arg Pro
    1040                1045                1050

Pro Gly  Lys Lys Asn Ser Thr  Ile His Leu Leu Ser  Gly Gly Glu
    1055                1060                1065

Lys Ala  Leu Thr Ala Leu Ala  Leu Val Phe Ala Ile  Phe Gln Leu
    1070                1075                1080

Asn Pro  Ala Pro Phe Cys Met  Leu Asp Glu Val Asp  Ala Pro Leu
    1085                1090                1095
```

```
Asp Asp  Ala Asn Val Gly Arg  Tyr Ala Arg Leu Val  Lys Glu Met
    1100                 1105                 1110

Ser Glu  Lys Val Gln Phe Ile  Tyr Ile Thr His Asn  Lys Ile Ala
    1115                 1120                 1125

Met Glu  Met Ala Asp Gln Leu  Met Gly Val Thr Met  His Glu Pro
    1130                 1135                 1140

Gly Cys  Ser Arg Leu Val Ala  Val Asp Val Glu Glu  Ala Val Ala
    1145                 1150                 1155

Leu Ala  Glu Ala
    1160


<210> SEQ ID NO 14
<211> LENGTH: 1417
<212> TYPE: PRT
<213> ORGANISM: Pseudomonas aeruginosa

<400> SEQUENCE: 14

Met Asn Lys Ser Tyr Thr Leu Val Trp Asn Gln Ala Thr Gly Cys Trp
1               5                   10                  15

Asn Val Ala Ser Glu Gly Thr Arg Arg Arg Ser Lys Ser Gly Arg Gly
            20                  25                  30

Lys Ala Leu Val Val Ala Gly Ala Ser Leu Leu Gly Leu Phe Cys Gln
        35                  40                  45

Ala Pro Ala Phe Ala Leu Pro Ser Gly Ala Thr Val Val Ser Gly Asp
    50                  55                  60

Ala Gly Phe Gln Thr Ser Thr Asp Gly Arg His Met Val Ile Asp Gln
65                  70                  75                  80

Gln Ser His Lys Leu Ile Thr Asn Trp Asn Glu Phe Ser Val Arg Ala
                85                  90                  95

Asp Glu Arg Val Ser Phe His Gln Pro Gly Gln Asp Ala Val Ala Leu
            100                 105                 110

Asn Arg Val Ile Gly Arg Asn Gly Ser Asp Ile Gln Gly Arg Ile Asp
        115                 120                 125

Ala Asn Gly Lys Val Phe Leu Val Asn Pro Asn Gly Val Val Phe Gly
    130                 135                 140

Lys Ser Ala Gln Val Asn Val Gly Gly Leu Val Ala Ser Thr Leu Asp
145                 150                 155                 160

Leu Ala Asp Arg Asp Phe Leu Ala Gly Asn Tyr Gln Phe Ser Gly Asp
                165                 170                 175

Ser Gly Ala Thr Val Ser Asn Ala Gly Ser Leu Gln Ala Ser Glu Gly
            180                 185                 190

Gly Ser Ile Ala Leu Leu Gly Ala Arg Val Ser Asn Asp Gly Leu Ile
        195                 200                 205

Gln Ala Gln Leu Gly Asp Val Ala Leu Gly Ala Gly Gln Gly Ile Asn
    210                 215                 220

Leu Asn Phe Asp Gly Asp Gly Leu Leu Asn Leu Gln Val Asp Lys Gly
225                 230                 235                 240

Ser Val Asp Ala Leu Ala His Asn Gly Gly Leu Ile Arg Ala Asp Gly
                245                 250                 255

Gly Gln Val Leu Met Ser Ala Arg Ser Ala Asp Ser Leu Leu Lys Thr
            260                 265                 270

Val Val Asn Asn Gln Gly Thr Leu Glu Ala Arg Thr Leu Arg Ser Ala
        275                 280                 285

Glu Gly Arg Ile Val Leu Asp Gly Gly Glu Gln Gly Thr Val Arg Val
    290                 295                 300
```

```
Ala Gly Lys Gln Asp Ala Ser Ala Ile Gly Gly Gly Asn Gly Gly Leu
305                 310                 315                 320

Val Leu Asn Gln Gly Ala Asn Val Glu Ile Gln Arg Thr Ala Gln Val
                325                 330                 335

Asp Thr His Ala Asp Gln Gly Ala Thr Gly Thr Trp Arg Ile Leu Ser
            340                 345                 350

His Glu Val Ser Val Ala Ala Val Gly Gln Ala Asn Ala Ala Gly Asp
        355                 360                 365

Gly Ser Gly Gln Val His Val Ala Gln Gly Pro Ala Gly Ala Asn Ala
    370                 375                 380

Ser Asp Ser Asn Gly Val Thr Ile Val Gln Gln Gln Pro Ala Val Asp
385                 390                 395                 400

Leu Ala Ala Gly Ala Asn Gly Thr Ser Ala Val Gln Ser Gln Ser Gly
                405                 410                 415

Ala Asn Ile Gly Ser Gly Ala Asn Gly Ile Ser Val Val Gln Ser Gln
            420                 425                 430

Asn Ser Pro Asn Ile Gly Ser Gly Ala Asn Gly Ile Ser Val Val Gln
        435                 440                 445

Ser Gln Asn Gly Ala Asn Ile Gly Ala Gly Ala Ser Gly Ile Ser Val
    450                 455                 460

Val Gln Ser Gln Asn Ser Pro Asn Ile Gly Ser Gly Val Asn Gly Val
465                 470                 475                 480

Thr Val Val Gln Ser Gln Asn Gly Ala Asn Ile Gly Ser Gly Ala Ser
                485                 490                 495

Gly Ile Thr Val Val Gln Ser Gln Asn Gly Ala Asn Ile Gly Ser Gly
            500                 505                 510

Ala Ser Gly Ile Ser Val Val Gln Ser Gln Ser Gly Pro Ser Ile Gly
        515                 520                 525

Ser Gly Val Asn Gly Val Thr Ile Val Gln Ser Gln Ser Gly Ala Asn
    530                 535                 540

Ile Gly Pro Gly Val Ser Gly Ile Asp Val Val Gln Thr Gln Thr Leu
545                 550                 555                 560

Pro Asn Leu Ser Pro Gly Ala Asn Gly Ser Ser Ile Val Gln Val Gln
                565                 570                 575

Thr Leu Pro Asp Ile Ala Ala Asp Ala Gly Asn Val His Val Val Gln
            580                 585                 590

Val Gln Thr Gly Gly Asn Lys Val Phe Gly Asn Ser Ala Thr Asn Val
        595                 600                 605

Arg Ser Arg Thr Val Gln Ala Arg Ser Asn Glu Asn Val Gly Ser Gly
    610                 615                 620

Leu Ala Asn Pro Ser Ser Ala Gly Lys Gly Ser Thr Leu His Ala Asp
625                 630                 635                 640

Thr Leu Ala Arg Asn Leu Ser Thr Ser Asn Val Glu Val Val Ala Thr
                645                 650                 655

Arg Gly Asn Ala His Val Gly Ala Pro Leu Ser Trp Asp Ser Gly Asn
            660                 665                 670

Gly Leu Thr Leu Thr Ala Glu Arg Gly Asp Leu Arg Ile Asn Gly Ala
        675                 680                 685

Leu Thr Ala Gln Gly Glu Asn Ala Ser Leu Thr Leu Asn Ala Gly Gln
    690                 695                 700

Arg Pro Leu Arg Ile Asp Asp Ser Leu Ser Leu Thr Gly Gln Gly Ala
705                 710                 715                 720
```

```
Arg Val Glu Phe Asn Ser Asp Lys Gly Tyr Ala Leu Ala Glu Gly Thr
            725                 730                 735

Arg Ile Thr Leu Ser Gly Lys Asn Ala Gly Phe Arg Ala Asn Gly Arg
        740                 745                 750

Asp Tyr Ser Val Ile Gln Asp Leu Gln Gln Leu Arg Gly Ile Asp Arg
    755                 760                 765

Asp Leu Gly Gly Ser Tyr Val Leu Gly Asn Arg Ile Ala Gly Gly Asn
    770                 775                 780

Ser Ser Phe Leu Ser Ile Gly Asn Ala Ser Ala Phe Gly Gly Thr Phe
785                 790                 795                 800

Asp Gly Leu Gly Asn Thr Ile Asp Asn Leu Ala Val Tyr Gly Thr Gly
            805                 810                 815

Ala Tyr Ser Gly Leu Phe Ser Val Asn Arg Gly Thr Leu Arg Asn Leu
        820                 825                 830

Asn Leu Glu Arg Ile Ser Ala Asp Gly Ala Gln Ala Thr His Tyr Asn
    835                 840                 845

Val Gln Val Gly Ser Leu Ala Ala Val Asn Leu Gly Arg Ile Asp Asn
    850                 855                 860

Val Asn Ala Ser Asp Ile Arg Ile Ala Ala Ala Ser Lys Leu Asn Ser
865                 870                 875                 880

Leu Gly Gly Leu Val Ala Leu Asn Leu Gly Ser Ile Asp Asn Ala Ser
            885                 890                 895

Ala Ser Gly Thr Leu Val Gly Asn Arg His Thr Tyr Ala Leu Gly Gly
        900                 905                 910

Leu Ala Ala Glu Asn Ile Ser Thr Ala Arg Gly Val Ala Ser Ile Ser
    915                 920                 925

Asn Ser Arg Ala Asp Phe Ala Ile Ser Gly Gln Leu Lys Asp His Ala
    930                 935                 940

Ser His Tyr Gly Ala Gly Gly Leu Val Gly Arg Asn Arg Gly Gly Leu
945                 950                 955                 960

Ile Arg Ser Ser Gly Ser Gln Gly Thr Leu Ser Leu Ser Gly His Gly
            965                 970                 975

Met Asn Leu Gly Gly Leu Val Gly Tyr Ser Ser Ala Gly Gly Leu Ala
        980                 985                 990

Asp Val Ser Ala Ser Val Asp Val  Ser Gly Asn Gly Gln  Arg Gly Leu
    995                 1000                 1005

Tyr Gly  Gly Leu Ile Gly Leu  Asn Val Asn Ser Gly  Ile Ala His
    1010                 1015                 1020

Ala Thr  Ala Ser Gly Lys Val  Arg Gly Thr Asp Ala  Glu Ala Leu
    1025                 1030                 1035

Gly Gly  Leu Ile Gly Arg Asn  Leu Asn Ala Ala Ile  Asn Asn Ala
    1040                 1045                 1050

Ser Ala  His Gly Asp Val Ser  Leu Gln Ala Gly Arg  Tyr Leu Gly
    1055                 1060                 1065

Gly Leu  Ile Gly His Asn Gln  Ala Gly Asn Leu Ala  Asn Val Ser
    1070                 1075                 1080

Thr Ser  Gly Asn Leu Ser Gly  Gly Ser Leu Leu Gln  Ala Gly Gly
    1085                 1090                 1095

Leu Ile  Gly Leu Asn Ala Asn  Ala Ser Leu Val Asn  Ala Ser Ala
    1100                 1105                 1110

Lys Gly  Asn Val Ala Thr Arg  Gly Ala Glu Ala Val  Gly Gly Leu
    1115                 1120                 1125

Leu Gly  Glu Asn Leu Tyr Gly  Ser Val Ile Asn Gly  Ser Ala Ser
```

```
    1130                1135                1140

Gly Glu Val Thr Asp Gly Ser Gly Lys Thr Leu Gly Gly Leu Ile
    1145                1150                1155

Gly Ser Asn Leu Gly Gly Asn His Ser Asn Leu Lys Ala Ser Gly
    1160                1165                1170

Trp Val Asn Ala Gly Ala Asn Ser Asp Val Gly Gly Leu Ile Gly
    1175                1180                1185

His Asn Arg Gly Gly Asn His Ser Thr Leu Ala Ala Ser Gly Asn
    1190                1195                1200

Val Thr Gly Gly Lys Gly Ser Arg Val Gly Gly Leu Val Gly Tyr
    1205                1210                1215

Asn Asp Ala Ala Ser Leu Thr Asn Val Ser Ala Ser Gly Asn Val
    1220                1225                1230

Ser Ala Ser Gly Ser Arg Ala Ile Gly Gly Leu Ile Gly Ser Asp
    1235                1240                1245

Leu Arg Gly Ser Leu Met Leu Ala Ser Ser His Gly Ile Val Asn
    1250                1255                1260

Asp Lys Thr Ser His Asn Leu Gly Gly Leu Val Gly Arg Gly Glu
    1265                1270                1275

Asn Thr Ser Ile Arg Ser Ala Lys Ala Ser Gly Ala Val Ser Gly
    1280                1285                1290

Gly Ala Gly Ile Arg Ala Gly Gly Leu Val Gly Ser Leu Glu Gly
    1295                1300                1305

Trp Gln Ala Leu Ile Leu Gly Ala Ser Ala Gly Gly Asp Val Thr
    1310                1315                1320

Ala Gly Tyr Asp Ser Tyr Ile Gly Gly Leu Val Gly Phe Ser Thr
    1325                1330                1335

Ala Thr Ile Ser Gly Ala Ser Ala Ser Gly Lys Val Gly Gly Ser
    1340                1345                1350

Gly Leu Leu Gly Gly Leu Val Ala Trp Asn Gln Gly Asn Val Met
    1355                1360                1365

Gly Ser Ser Ala Ser Gly Arg Leu Glu Pro Gln Ile Pro Asn Gln
    1370                1375                1380

Ile His Gly Gly Leu Ile Gly Ile Asn Phe Gly Trp Gln Ser Trp
    1385                1390                1395

Asn Ser Val Tyr Gly Ala Ala Ala Thr Val Pro Met Ile Gly Arg
    1400                1405                1410

His Tyr Asn Leu
    1415
```

<210> SEQ ID NO 15
<211> LENGTH: 408
<212> TYPE: DNA
<213> ORGANISM: Pseudomonas aeruginosa

<400> SEQUENCE: 15

```
atgccccgtg gcgacaagag caagtacagc gacaagcagc agcgcaaggc cgagcacatc     60

gaggagagct acaaggccaa gggtgtgagc gagtcggaag ccgaggcgcg cgcctgggcg    120

acggtgaaca agcagtccgg cggcggcgag cgcaagggcg gttccggccg cgccaagagc    180

gagacggcca agcgcgccga ccgcaaggac tcggcccatc gcgccgccca ggcccgctca    240

gggagaccgg ccaaccgcgg ctcggcgagc cgtggcaaac gtcaaggcag cacctcggtg    300

agcgagatga cccgcgagga attgatgcag ctggcgcgca agcgcgacat ccgcggtcgt    360
```

tcgacgatgc gcaaggccga actgatcgag gccctgtccc gggcctga 408

<210> SEQ ID NO 16
<211> LENGTH: 417
<212> TYPE: DNA
<213> ORGANISM: Pseudomonas aeruginosa

<400> SEQUENCE: 16
atgaatatcc tgcgtatccc gatgttcgta ttggccatgg ccgtctcggc ccatggtttc 60
gctgccaccg cgcagcagga gaagatgacc gcctgcaacg ccgaggccac caccaaggcg 120
ctcaagggcg acgaacgcaa ggcgttcatg agcggctgcc tgaaggccgg cgcgcctgcc 180
ggcggcaagg ccaccgccca gcaggagaag atgaagagct gcaacgccga cgccagtgcc 240
aagtcgctca agggcgacga acgcaaggcg ttcatgagca gttgcctgaa ggccggcggc 300
agcgccaagg cggcgaccca gcaggagaag atgaagacct gcaacgccga cgccaccgcc 360
aaggcgctca agggcgacga acgcaaggcg ttcatgagca cctgcctgaa gaagtga 417

<210> SEQ ID NO 17
<211> LENGTH: 426
<212> TYPE: DNA
<213> ORGANISM: Pseudomonas aeruginosa

<400> SEQUENCE: 17
atggctacac gacggaaaac aacaccccag gaaatcgatg atatccagga ccgcatgggt 60
tcgatgcgcg agctcgattt cgacgagcgc cgccaggcgc gtaaggcgcg gatcggcgac 120
gagcggcccg aggccgaggt ggaggccgaa ttttcctcgc ggcgggtacg cgaggcgggc 180
cacgctggcg ggcagccgga cgaggacgat ggttaccagg ataacgtcgg catggacgat 240
ctggcgccgg aaaccctgat cgacgaaagc ggcgcccgct cgccggccga gcgcggcggc 300
gaatcgcccg cggacaagcg cctgagggtc gtgcatggca acgagatcgg agccggccac 360
ggcctcgacg aggccgagct ggcgcgtcgt gatccgctcg acggttcctc cgacgaggaa 420
cgctga 426

<210> SEQ ID NO 18
<211> LENGTH: 453
<212> TYPE: DNA
<213> ORGANISM: Pseudomonas aeruginosa

<400> SEQUENCE: 18
atgcgacgca tgatcctccc ggccagcttg ttgctcgccc tctcctcttt cgccatggcc 60
gccccgatct acaaatgggt cgacgccgag ggcgtcaccc acttcggcgc acaaccgccg 120
caaggtgcgc aagcgaccac ggtgaatacc cagaccgccc cgccgccgga caacttcccc 180
ctgcccccct cgaccccggc accgaccatc cagcagaaac cggccgatcc cgagcagaag 240
gcgatcgacg acaaggtgaa gcagcaagtg gcgaaggaag aggccgagcg caagcagttc 300
tgcgaagaga cccgcaacaa cctcgcgcaa ctgaagaaca acccgcgcgt aagggtcgac 360
gaaggcaagg gcgaactccg tcgcctcggc gaggaagaac gccaggagcg aatcgccaag 420
gccgaaaagg cgatccagga gaattgccgc tga 453

<210> SEQ ID NO 19
<211> LENGTH: 714
<212> TYPE: DNA
<213> ORGANISM: Pseudomonas aeruginosa

<400> SEQUENCE: 19

```
atgttcacct cccgttgcct gcctctggcc gcagccgtca ccgcactggc gctgctcgcc      60

ggttgtgcca acaacaaccc ctacgacacg caaagccaaa gccagggtgg catgagcaag     120

acggccaagt acggcggact gggtgcgctg gccggcgccg tcgccggcgc tgcgatcgac     180

cacaacaacc gtggcaaggg cgcgctgatc ggcgctgccg ttgccggcgc ggccgccgcg     240

ggttatggct actacgccga caagcaggaa gccgagctgc gtcggcagat ggaaggcacc     300

ggcgtggaag tgcagcgcca aggtgacgac atcaagctga tcatgccggg caacatcacc     360

ttcgccaccg attcggcgaa catcgccccg agcttctacg cgccgctgaa caacctggcg     420

aactcgttca agcagtacaa ccagaacacc atcgagattg tcggttacac cgacagcacc     480

ggcagccgcc agcacaacat ggacctgtcc cagcgtcgtg cgcagagcgt ggccggctac     540

ctgaccgccc agggcgtcga cggcacccgc ctgagcaccc gcggcatggg cccggaccag     600

ccgatcgcga gcaactccac tgccgacggt cgcgcgcaga accggcgcgt cgaggtcaac     660

ctgcgaccgg ttccgggcgc ccagggcccg gcgcagaccc agccgcagta ctga           714
```

<210> SEQ ID NO 20
<211> LENGTH: 1191
<212> TYPE: DNA
<213> ORGANISM: Pseudomonas aeruginosa

<400> SEQUENCE: 20

```
atgaagcgac tggctggact gaccgccctc gccctggtta tcggcaacac ttccggctgc      60

ggctggctgt gggggccgga gggctatttc cgcgaccgcg gtgacgacta cctcggcgcc     120

cgcgaaacgc ctcccatgca attgcccgaa ggggtgcaca gcaagccgct cgatccgctg     180

ctgccgattc cgctgaacgt cgccaccacc cacgaaaaag agggtgagta cgaggttccg     240

cgtccgcagc cgctggccaa cgccggcgac atcagcgact acagcctgca gcgcagcggt     300

gatagccgct gggtcgtggc ccagcgtccg ccggcggaag tctggccggt ggcccggcag     360

ttcttcgagg agaacggttt ccgcatcgcc gacgagcgcc cgcagaccgg cgagttcagt     420

tccgactggc aatcgctgtc gcagctttcc gcgccgctgg cacgccgcct tagcagccgc     480

gtgagcggtg tcgagccgga cggccaggca cgggttcggg tgcgtatcga gcccggcgtg     540

caaagcaata ccagcgaggt ctacgtgctc agccagaccc gcgccgccgg tgacaccagc     600

agcccgagct ggccgagcaa gtcggtggcg ccgagcctcg acgcggcgct gctcgacgag     660

atggtcgcga gcatggcgcg cagcgccgag cagggcggct cggtctccct gctggcagcc     720

aactcgatct acgacacgcc cggcaccttc gagttgagca aggacggcag cggcaacccg     780

gtgctgacct tgcagtccga cttcgaccgc tcctgggtca gcgtcgggcg tgccctggat     840

aacgccgata tccgcgtcga cgacctcaac cgcagccttg gcgtgtacta cgtgaacatc     900

gccgaagggg cgaagaagcc cgacgaagac aagcccgggt tcttcagtcg cctgttcggc     960

ggcggcgaga agaccaagga agaggaagac gccaaggcgc agcgctacca ggtccgcctg    1020

accaccgtca gcgacgccgt gcaggtcacc gtcgacaagg acatcaacac ctctgcgccg    1080

gccgatgtcg cgcaaaacgt actggaaaaa ctccaggaga gcatgcgcaa tgcggttcgc    1140

ggttctgggc agcggaagcc ggggcaattc ggccttggtg agcagttctg a             1191
```

<210> SEQ ID NO 21
<211> LENGTH: 1632
<212> TYPE: DNA
<213> ORGANISM: Pseudomonas aeruginosa

<400> SEQUENCE: 21
atgatccgcc tgttctgcag cctgcttctc gcgctcctct gcgtctccgc ccacgccagc 60
ttcagcgcca gcgtcgaccg cgcccgcctg accgaagggg aaagcgtcga actgacgctg 120
gaatcggacg acccgaccct cttcggcaag cccgacctga gcccgctgga cgccctcttc 180
gaggtcctcg gcacgcgcca ggtcaaccgt ctcgccacac agaacggccg ggcccaggcc 240
accacccgct ggatcgtcac cctcctgccg aagcagagcg gctacgtggc gatcccgccg 300
atcagcctcg gcgccagcag cacccagccg atcaggctgc acgtactgga ggcgcgcgac 360
cgcgccaaga gcagcaagct ggcgccggtc ttcatcgatg ccagcgtcga ccaggagacg 420
gtctacgtgc aggcccaggc gatcctcacc ctgcgcatct accactcggt gtcgctatac 480
gacgacagca gcctgacccc gctggcgatg aacgacgcga aggtcgaaca gctcggcgag 540
gcgcgcacct acgagaagga gatcaacggc atccgccacg gcgtgatcga ggtgcgctac 600
gcgatcttcc cgcagaagag cggcaccctg gagattcctg cgcaagcctt cagcgcgacc 660
ctggtcgacc gtggcagtga cgactacaac cccttcggcc cgcgccccgg ccggcagatg 720
cgggtgactt cgccgagcat cccgctgcag gtccggccca agcctgccga ctatccggcc 780
gacgcgccct ggatgccggc ccgcgcgctg agcatcagcg aaagctggag cccgcagccg 840
gagcaggcgc aggtcggcga atcgctgacg cgcaatgtgc tgctgaaggt cgaggggctt 900
tccggcaccc agcttccgcc gttgccgctg cccgacgtgc aaggcctgcg gcgctacccg 960
gaccaaccgc agttggccga ccagagcacc gaccagggcc tcatcggcag tcgcgaggaa 1020
cgcgaggcgc tggtgcccga gcaggccggg cgcatcgagt tgccggcgct cgaagtggtc 1080
tggtggaaca cccgcgaaga ccgcctggag cgcaccagcc tgccaccgcg caccctggaa 1140
gtggccgccg cgccgcaggc cgaggcggag ccgccggcgg cggcgctgcc gctcggcgaa 1200
cgcctggagc cgacgctctg gccctggcaa ctggctaccg ccgtgctggc cctgaccacc 1260
ctgctcggct tcggcctctg gtggcgcgcc cgccagctgc cggcggtgat ccgcgccgcg 1320
gccaacggcc cgagcagccg cagcctgctc gacgagctgc gccgcgcctg cctggccaac 1380
gatccccagg cgacccgcca ggccctggac gcctgggccc gtcagcaacc cgataccctg 1440
gccgacatgg cggcccgctt cgtaccgctg tccgacgccc tggatggcct caacggcgcg 1500
ctgtacagcg agagcggcca ttcctggcag ggcgaggacc tgtggcgggc gatccgcgcc 1560
ctgcccacca cggaacaagc gccggcggga gcggtcgaca atggcggcct gccaccgctc 1620
tatccgcgct ga 1632

<210> SEQ ID NO 22
<211> LENGTH: 1920
<212> TYPE: DNA
<213> ORGANISM: Pseudomonas aeruginosa

<400> SEQUENCE: 22
atgtcctttt cttccctcgg actctccgag gcgcttgccc gcgctgtgga ggctgcgggc 60
tacagccagc ccactcccgt gcaacagcgg gcgattcccg ccgtgttgca aggtcgcgac 120
ctgatggttg cggcacagac cggcaccggc aagaccggtg gtttcgccct gccggtactg 180
gagcgcctgt tccccgccgg tcatcccgac cgcgaacacc gccacggccc gcgccaggcg 240
cgcgtgctgg tactgacccc gacccgtgag ctggccgccc aggtgcatga cagcttcaag 300
gtctacgccc gcgacctgcc gctgaacagc acctgcatct tcggtggggt tggcatgaac 360
ccgcagatcc aggccctggc caagggcgtc gacgtactcg tcgcctgccc cggccgcctg 420

```
ctcgacctgg ccgggcagaa caaggtcgac ctgtcccacg tggaaatcct cgtcctcgac    480

gaagccgacc gcatgctcga catgggcttc atccacgatg tgaagaaggt tctcgccaag    540

ctgccgccca agcgccagaa cctgctgttc tcggcaacct tctcgaaaga catcgtcgac    600

ctcgccaaca agctcctgca caacccggaa cgcatcgagg taacgccgcc gaacaccacg    660

gtcgagcgca tcgagcaacg cgtgttccgc ctgccggctc cgcagaagcg cgccctgctg    720

gcgcacctgg taaccgtcgg cgcctgggaa caggtgctgg tcttcacccg taccaagcac    780

ggcgccaacc gtctcgccga gtacctgacc aagcacggcc tgccggccgc cgcgatccat    840

ggcaacaaga gccagaacgc gcggaccaag gcgctggccg acttcaaggc caacgacgtg    900

cgcatcctgg tggcgaccga catcgccgcc cgcggcctgg atatcgacca gttgccccat    960

gtggtcaact acgagctgcc caacgtcgag gaagactatg tccaccgcat cggccgtacc   1020

ggccgagccg gacgcagcgg cgaggcgatc tcgctggtgg cgccggacga agagaagctg   1080

ctcaaggcca tcgagaagat gaccagacag cgtattcccg atggcgatgc ccagggtttc   1140

gaccccgagg ccgtgctgcc cgaggtggcc cagccggagc cccgcgaagc gccgcagaag   1200

cagccgcgcc gcgacaagga acggcgcagc agccgcgagc gcaagccgaa agacgcccag   1260

gcgagcaacc ccgacagcaa tgtcgctgcg gcccaggacg gtaccgagaa gccggctgga   1320

aagcgccgcc gtcgcggtgg caagaacaag gaaaaccgcg aggccggcca agcgcagcag   1380

ccgcggcaga gccgcgaagc gcgtccggcc aagcccaatc ggccgccgga agtcgacggt   1440

aatcgcgatc cggaagagtt cctcgacgac gacttcgaca atttcggcaa ccgcgccgac   1500

tacgtcagcc cctaccaggg ccaggaaaac aagggacgcg gacgccgcgg tggccagcag   1560

aaaccccagg gcggcaccgg ccagcagggt cgtggccaag gccagggcca agctcgcggc   1620

aagagccagg gcgccgctca aggcggcgct cgcggtcagg gtgccggcca gggcaaggcg   1680

aagaaaccgc gcgccggcaa gccgcgcggc cagggtcgcg agaatgcctc gcggatgagc   1740

gacgcgccgc tgcgcgagcc gtccgagtat ggcaccggca agcagccgag ccgccagccg   1800

gtggtgatca acaagcgcga cctggtgcgc atggatcgct tccccaccgc cgagcagctc   1860

gacgagctgg aaccgcggcg caagggcgag cgccccgcac tgctgacccg caaccgctaa   1920
```

<210> SEQ ID NO 23
<211> LENGTH: 2028
<212> TYPE: DNA
<213> ORGANISM: Pseudomonas aeruginosa

<400> SEQUENCE: 23

```
atgcctgctt ctttcccgcg cctcggcttg ctcggcgcac tgtgctccat cgttcccctg     60

ctccatgcca gcgaaccgac cacggacgct gcgctcatcg aaaaaggccg ctacgtggcc    120

cagctcggcg actgcatcgc ctgccatacc ggcccgcagg gcgcgccgat ggccggcggc    180

ctggagctga agacgccaat gggtaccatc tactcgacca acatcactcc cgaccgggag    240

accggcatcg gccgctacag cttcgaagag ttcgaccgcg ccatgcgcaa gggggtgacc    300

gccgagggag tgaatctcta tccggcgatg ccctacccgt cctacgccaa gatcagcgaa    360

gaagacatgc gtgcactgta cgcctacctg atgcacggcg tgcaacccgt cacccaggcg    420

aatacgccga gcgcgatgag ctggccgttc aaccagcgct ggggcctgtc gctgtggaac    480

tgggcgttcc tcgacgacgc gccgttcacc ccctccagcg acgcggaccc ggtgatcaac    540

cgcggcgcct acctggtaca ggggctcggc cactgcggcg cctgccatac tccgcgcggc    600
```

```
atcgccttcc aggaaaaagc catgagcgaa gccggtcgtt ccgggcagtt ctacctcgcc    660

ggagaaaccg tcgaacaatg gcaagccctg agcctgcgca acctgtggac ggtggaggac    720

accgtgcagt tgctgaagac cgggcagaac cgcttcgcca cggtgtccgg cagcatgacc    780

gatgtcatcc accacagcac ccagcacttc agcgacgacg atctgctggc catcgccagc    840

tacctgaagt ccctgccggc cggcaaggac gacctgccca tgcccgacag cgaacgccca    900

ctggcagcac cggtcgacct gtacagctcg cggggcggtc tcggctacgc gcagttctgc    960

tccgactgcc accgcaagga cggcagcggc gtcccaggca tgttcccgcc gctggccggc   1020

aaccccacgg tcgcttcggc caacccgagc acgctactgc atatcaccct taccggctgg   1080

aaaaccgcgc agaccgcaac ccactcgcgg gtctacacca tgcccggctt cgcccagctg   1140

gaagaccgcg aaatcgccga gatcctcagc ttcgtccgca gcagttgggg caaccagggg   1200

tcgtcgatcg atgccggcca ggtgaagaaa ctgcgccagc ggatcgaggc cggcaacggc   1260

ccggccacga ccttcgtctc tccacgcctg gcggacatgc tcgcggcgcc gaacgccgaa   1320

caggtggtac gcggcatgcg cctgcacctg gagacccgcg agctgctgcc ggcgaacgtc   1380

ggcaaccagt tgcactgcac cagttgccac ctgaacgccg gaaccgtagc cgacggctcg   1440

cccttcgtcg gcgtctcggc gttcttcccc agctacgcgc cccgggcggg caaggtcatc   1500

ggcctggagg aacgcatcaa cggctgcttc cggcgctcga tgaacggtaa gcctctgccg   1560

ccggactctg ccgacatgca ggcgatggtg gcctacttcg actggatgaa gaacaacacc   1620

cggccgcagg acaaggtcgc cggccgcggc gtcggcaagg tcgacccggc gctgaagccc   1680

gacccggaga acggccgcaa ggtctacgcc cgacaatgcg tggtgtgtca tggcgagaat   1740

ggcgaggggc tgaggaacag tgccggcgag atgctcttcc caccgctgtg ggcgacgag    1800

tcgttcaata tcggcgccgg catggcgcgg accttcaccg ctgccgcctt cgtcaagcac   1860

aacatgccga tcggcttcca ggaacgcttc ccgctcggcc agggcggcct cagcgaccag   1920

gacgcagtgg acgtcgcgga gtatttttcg caccagccgc gcccggactt cccggacaag   1980

atcaaggact ggccgaagga caagcgtccg ctggatgccc gctactga                2028
```

<210> SEQ ID NO 24
<211> LENGTH: 2049
<212> TYPE: DNA
<213> ORGANISM: Pseudomonas aeruginosa

<400> SEQUENCE: 24

```
atgcccggta aagccttgcg tgtcatgttg tgtgcctggt cgtgcctgtt ggccgggcag     60

gcgagcgccc tgggagtggg agacatcatc ctgcattcgg cgctcaacca gccgctggat    120

gcggatatcg aactgctcga cgtcggcgat ctcggcgcgg acgagatcga ggtccgcctg    180

gcgggcgccg acgtcttcgc cgcggccggg gtggaacgct tgcagttcct caacgagctg    240

cgtttcagtc cggtgctcca ggggcgcggt ggcaatcgca tccatgtgtc ctcgatccga    300

ccggtgcagg agccctacct gaatttcctg gtggaggtgg cccgccccaa cggccgcatc    360

gtccgcgaat tcaccgtact gctcgatccg ctcggttata cgccgcgcat gcttccggcc    420

gcgcgcagcg ggatcgagcc gcagcggcaa tcctcgacgc cggtgcctgc gccgcgtagt    480

gccgcggtcg tcgtagaccc ggcactgctg gagccgggcg acgaatacct ggctcgcccc    540

agcgacaacc tctgggccat cagcggacgc ctgcgtggtg ccggcaacgc cgatcgcgcg    600

caactcatgg aggctctgta ccagctcaat ccgcaggcct tcgtcaatgc cgaccggcac    660

cggctcaagg ccggcgcgcg cctgcgcctg ccggccggct accagccgga gcgaggcgcg    720
```

```
cccggcgccg tgaaggaggc ggccgtggaa gtcctgccgc cagccgatgc cgccgtggtg    780

gaaaacgctc cggcggctct cgtcgaggcg cagcgccagg cggatgccga ggccgaggcg    840

ttggcccggc aacgggagga actgagccag cggatggacg atctgcaacg ccagttgcag    900

gccttgcagg aacaactgca gcagcgcgat caccaggtcg ccgaactgca acagcaactg    960

gcccggcgcc aggcggtgcg gcccgcggcg ccgccgcctg ccgcggccgc gccttcggtt   1020

gcgcaaccgg ttgaaacgcc gacggactcg cagtactggc gctggatgat cgtcctgctg   1080

ctggtcctcg ctctgctcgg cgtgttgctg ttgcgtcgcc gccgcgaaga ggctcctgtc   1140

ccggcggtcg aaccgaagcg ccgggtcgcc ctgaacctgc cgctgcggcg tgcgccgcgc   1200

cccccggcgg ccgcaccggc gccggcaaag gtcgaagaac aggccaggcc gccggtcgcc   1260

gctccctcca gcccgccgcc gtctcctccg cctgctccgg ccgccgctcc gcgcgccgcc   1320

atggctgcgg cggacaagct ggacggcgcc gacatctata tcgcctacgg tcgctacgga   1380

caggcccgcg acctgctgcg tcaggtactc gccgagcagc cgcagcgcct gagcgcgcgg   1440

atgaagctgt tgctggtgct ggctgagctg ggcgatgcgg ccggcttcga cgcgctggcc   1500

gaggaaaccc tggccagtgg cggcaacccg gaggccatcg acgagttgcg cggacgctac   1560

ccggcgctgc tacagatgcc ggcgaccgag acgccggcgg caacaaccaa ggacgacgac   1620

tggagcgacc tgccgctggc cgagtcgccc gttttgcagc aaccggatgc gacctcgggc   1680

gccgacggct tcggcgacct caacctcgat ctcgatctcg actggggcgc cctggagaat   1740

cccctggaca accccgacct gccgcgccgc gccgctgccg gcaaggcgga accggcggag   1800

gagcccctgg cgttcgagag caatctccat gaactgccgg atgtcgccga gtacgaacac   1860

ctcgaactcg accagccaga gccggccacg gtgccgccgg aggaggcctc ggccagcctg   1920

gaccgggccc gcgcctgcat cgacagcggc gatctcgacc aggccagccg catcctgcgc   1980

ctggtggtgg cgcacggcga cccgtggcag aaggccgagg cgcgcgagtt gctggcactg   2040

atcgcctga                                                           2049
```

<210> SEQ ID NO 25
<211> LENGTH: 2064
<212> TYPE: DNA
<213> ORGANISM: Pseudomonas aeruginosa

<400> SEQUENCE: 25

```
atgtcctctt ccggcctttt cccttcccgt ccgctctggc ctctcacgcc actggcgctg     60

gcctgcctga tcgtttcggg ggaaacgctc ggcgccgacg gccgccccag cgaattgccc    120

tcccaggtga tcaccgccaa cccgctgggc aacgaatctc ccgccacgcc cagcagcgtg    180

ctcgaaggcg acgagctgac cctgcgacag aaaggcagcc tcggcgaaac cctcaacggc    240

ctgcccgggg tgtcctccac ctacttcgga ccgggcgcca gccgaccggt gatccgcggc    300

atggacggtg atcgcatccg cctgctgcgc aacggcgtcg gtgcgctcga cgcctcgtcg    360

ctgtcctacg accacgcggt gccggaagac cccaacagcg tcgagcgcct ggaagtggta    420

cgcggcccgg ccgccctgct ctacggcggc aatgccatcg gcggggtggt gaacagcttc    480

gacaaccgca tccccagcga acccgtcgac ggcatccacg gcagcggcga actgcgctac    540

ggcggcgccg acaccacccg tagccgctcc ggcgcactgg aggccggcga cggcaacttc    600

gccctgcacg tggacgccgc cagccgcgag ttcaacgacg tcaggattcc cggctacgcc    660

cattccagcc gccagcggca gatcgacggc gacaccggca agcatcgggt gcagaacagc    720
```

```
gacggccgcc aggacggcgg cgccgtcggt ggctcctatc actgggagca cggttacgcc    780
ggcctctcct acagcggcta cgacagcaac tatggctcgc cggccgagga cgacgtgcgc    840
ctgaagatgc agcaggaccg ctacgccttc gcctccgaga tccgcgacct cgaaggcccg    900
ttcacctcgc tgaagctgga cgccgcctat accaagtacg agcacaagga aatcgaggac    960
ggcgagaccg gcaccacctt caagaacgaa ggctacgaag gccgcatcga ggcccgccac   1020
cgcccgctcg gcccgctgaa cggggtggtc ggcgcgcagt tcgccaacag ccgcttctcc   1080
gccctcggcg aggaagcctt cgtgccgcac acggaaaccg acagcgccgc gctgttcgcc   1140
ctggaggaat ggaagctcag cgaccgcctc gacctcagct tcggcgcccg cctggagcac   1200
acccgcgtgg accccgacgc caagggcaac gagcgcttcg ccgagaacga cggttcgcag   1260
agcttcacca ccggcagcct gtccaccggc gcggtgtaca agctgacgcc gatctggtcg   1320
ctggccgcca ccctcagcta caccgagcgc gccccgacct tctacgagct gtacgccaac   1380
ggtccgcacg ccgccaccgg tacctacgag gtaggcgatg ccgacgcgga caaggaaaag   1440
gcggtctcca ccgacctcgc cctgcgcttc gacaacggcg tgcacaaggg cagcgtcggg   1500
gtgttctaca gccgcttctc caactacatc ggcctgctcg ccagcggtcg ccatcgcaac   1560
gaggaaggcg aagtggtcgc cgccggcgat gacgaggcgc tgccggaata cctctacagc   1620
ggcgttcgcg cggacttcta cggcgtcgag gcgcaggacc gcatccacct gctggaaagc   1680
ccgtacggca acttcgacct ggaactctcc ggggactaca cccgcgccaa gaacaaggac   1740
accggcgaac cgctgccacg catcgccccg ctgcgcctga acaccgcgct gatctgggag   1800
ttgcagcagt ggcaggcgcg ggtcgacgtc gaacacgccg cctcgcagca ccgcgtgccg   1860
gaggaagaac tctccaccga cggctacacc accctcggcg ccagcctcgg ctacaacttc   1920
gacctcggcg agagccgctg gctggccttc gtcaagggca ccaacctgac caaccagacc   1980
gtgcgctacg ccagttcgat cctgcgcgac cgggtgccgg cggcgggacg cggcatcgag   2040
gcgggggtga aggtggcgtt ctga                                          2064
```

<210> SEQ ID NO 26
<211> LENGTH: 2412
<212> TYPE: DNA
<213> ORGANISM: Pseudomonas aeruginosa

<400> SEQUENCE: 26

```
atgaggcaat cagctttcca ccatgcccgg cgtcgttggc ctgtactggg cgtggcgctg     60
ggcgcgctac tggtcgcggc gtgtagcgag acgccgaagg tccccggcgt gcccccggcc    120
gacgaggaag tcggtcggcc gctgagcagt gtccgctccg gtgcgccgtt gcgcagcgcc    180
gacgtccgcg agcggcccca ggccgagcag gcccgccgcg cgctgagtgc cggacgcggc    240
gtggcgcgct ccggtggcgt ggctccggtc tcagcgacag cggccgaact cggcgagcag    300
ccggtcagcc tgaatttcgt cgataccgag gtggaagcgg tggtgcgcgc gctgtcgcgc    360
gccaccggcc ggcagttcct ggtcgacccg cgggtgaagg gcaagctgac cctggtttcc    420
gaaggccagg tgccggcgcg caccgcctac cgcatgctca ccagcgccct gcgcatgcag    480
ggcttcagcg tggtcgacgt cgacggggtc agccaggtgg tgccggaggc cgacgccaag    540
ctgctcggcg ggccggtcta cggcgccgac cggccggcgg ccaacggcat ggtcacgcgg    600
accttccgcc tgcgctacga gaacgcggtg aacctgatcc cggtactgcg cccgatcgtc    660
gcgcagaaca acccgatcaa tgcctatccg gggaacaaca ccgtggtggt caccgactac    720
gcggaaaacc tcgatcgggt cgccgggatc atcgccagca tcgacatccc cagcgccagc    780
```

```
gacaccgacg tggtgccgat ccagaacggt atcgcggtgg acatcgccag caccgtctcc    840

gaactgctcg acagccaggg cagcggcggc gccgagcagg gccagaagac cgtggtgctc    900

gccgacccac gctccaacag catcgtgatc cgctcgccga gccccgagcg cacgcaattg    960

gcgcgcgacc tgatcggcaa gctggacagc gtgcaaagca atcccggcaa cctccatgtg   1020

gtctacttgc gcaacgccca ggcgacccgc ctggcccagg ccctgcgcgg gctgatcacc   1080

ggcgacagcg gcggcgaggg caacgagggc gaccagcagc gcgcgcgcct gagcggcggc   1140

ggcatgctcg gtggcggcaa cagcggtact ggtagccagg gcctggggag cagcggcaat   1200

accacgggca gcggttccag cgggttgggc ggcagcaacc gcagcggcgg cgcctatggt   1260

gcgatgggca gcggccaggg cggcgccgga cccggtgcga tgggcgagga gaactcggcg   1320

ttctccgccg gcggggtaac cgtacaggcc gacgccacca ccaacaccct gctgatttcc   1380

gcacccgagc cgttgtaccg caacctccgc gaagtcatcg acctgctcga ccagcgccgc   1440

gcccaggtgg tgatcgaaag cctgatcgtc gaggtcagcg aagacgactc cagcgagttc   1500

ggcatccagt ggcaggccgg caacctcggc ggcaacggcg tgttcggcgg ggtcaacttc   1560

ggccagtcgg cgctgaacac ggccggcaag aacaccatcg acgtgttgcc caaggggctc   1620

aacatcggcc tggtggatgg caccgtggac atccccggga tcggcaagat cctcgacctc   1680

aaggtgctcg cccgggcgct gaagagccgc ggcggcacca acgtcctgtc gaccccgaac   1740

ctgctgaccc tggacaacga gtcggcgagc atcatggtcg gccagaccat acccttcgtc   1800

agcggccagt acgtcaccga cggcggcggt accagcaaca acccgttcca gaccatccag   1860

cgcgaggacg tcggcctgaa gctgaacatc cgtccgcaga tctccgaggg aggaacggtc   1920

aagctcgacg tctaccagga ggtcagcagc gtcgacgagc gcgccagcac cgccgccggg   1980

gtggtcacca acaagcgcgc gatcgatacc agcatcctcc tcgacgacgg ccagatcatg   2040

gtcctcggcg gcctgttgca ggacaacgtg caggacaaca ccgacggcgt tcccggactc   2100

tccagcctcc ccggcgtcgg ctcgctgttc cgctaccaga agcgctcgcg gaccaagacc   2160

aacctgatgg tcttcctgcg tccctacatc gtccgcgacg ccgccgccgg ccgcagcatc   2220

accctcaacc gctacgactt catccgccgc gcccagcagc gcgtgcagcc gcgccacgac   2280

tggagcgtcg gcgacatgca ggctccggtg ctgccgccgg cgcagcaggg catcccgcag   2340

gccgcctacg acttgcgccc gagcccgcgg ccgctgcgcg cggtaccgtt gggcgaggcg   2400

gcgccgctat ga                                                        2412
```

<210> SEQ ID NO 27
<211> LENGTH: 3489
<212> TYPE: DNA
<213> ORGANISM: Pseudomonas aeruginosa

<400> SEQUENCE: 27

```
atgcgcctga agagcatcaa gctggcgggg ttcaagtcct tcgtcgatcc gaccacggtg     60

aacttcccca gcaacatggc ggcagtggta gggccgaacg gctgcggcaa gtcgaacatc    120

atcgacgcgg tgcgctgggt gatgggcgaa agctcggcga agaacctgcg cggcgagtcg    180

atgaccgatg tcatcttcaa cggctcgaat acccgcaagc cggtgagcca ggcgagcatc    240

gagctgatct tcgacaacgc cgagaccacc ctggtgggcg aatacgccca gtacgccgag    300

atatccattc gccggcgggt ctcgcgggat gggcagaaca cctatttcct caacggcacc    360

aagtgccggc ggcgcgacat caccgacatc ttcctcggca ccggcctggg gccgcgcagc    420
```

```
tactcgatca tcgaacaggg catgatctcc aagctgatcg aggcgcgtcc ggaagacctg    480
cgcaacttca tcgaggaagc cgcgggcatt tccaagtaca aggagcgccg ccgcgaaacc    540
gaaagccgca tccgtcggac ccaggaaaac ctggcacgcc tcaccgacct gcgcgaagag    600
ctggggcggc aactggaacg cctgcaccgg caggcccagt cggcggaaaa ataccaggaa    660
cacaaggccg aggagcgcca gctcaaggcc cagctgggtg ccgtgcgctg gcgcgacctg    720
aacgagcagg tcggtcagcg cgagcgggtc atcggcgacc aggagatcgc cttcgaggcc    780
ctggtggccg agcagcgtgg tgccgatgcc ggcatcgaac ggctgcgcga cggccatcac    840
gagttgtccg aacgcttcaa ccaggtgcag gcacgcttct attcggtcgg cggcgacatc    900
gcccgggtcg agcagagcat ccagcatggc cagcagcgcc agcgccagtt gcaggacgac    960
ttgcgcgaag ccgaacggac ccgccaggaa accgaatcgc acctcgggca tgaccgtacc   1020
ttgctcgcga ccctggccga ggaaatggcc atgctcgcac cggaacagga actcagcgcg   1080
gccgccgcgg aagaagcggg catcgccctg gaacaggccg agcagggcat gcaggcctgg   1140
cagcagcagt gggatgcctt caaccagcag agcgccgaac cccgccgcca ggccgaggtg   1200
cagcagtcgc gcatccagca cctggagcag agcctggagc gcctgcagga tcgcgagcgg   1260
cgcctgcagg aggagcgtgg ccagttggcg gccgaccccg aggacgcggc gatcctcgaa   1320
ctcaacgaac aggtggcgat cgccgaactg gccctggaag aactgcaatt gcaggagcag   1380
ggccaagccg agcgactcga acaattgcgc caggaattgc agcagctggc cgccgaacag   1440
caccaggcgc agggcgagtt gcagcgcctg aacgggcgca tcgcttcgct ggaggccctg   1500
cagcaggccg ctctcgatcc cggacagggc gccttggagt ggttgcgcga gcagggcctg   1560
gaacaacgtc cgcgcctcgc cgaaggcttg cgtgtcgagc cgggttggga gctggcggtg   1620
gagaccgtgc tcggcgcgga tctgcaggcg gtcttgctgg acggcttcga cgggctcgcc   1680
ctggccggct tcggcaaggg cgagctgcgc ctgctcagcc ccgctcgcgg agccgcgacg   1740
gcggccggtt cgctgctgga caaggtccgc gccgacgccg acctgagtcc ctggttggcc   1800
cgggtgaaac cggtggagac cctggaacag gcgctcgccc agcgcggcgc cctggacgac   1860
ggcgagagcc tgatcagtcg cgatggctac tgggtcggcc ggcacttcct gcgggtccgg   1920
cgcagcgacg aggcccaggg cggcatgctc gcccgcgccc aggaactgga ggcgttgcag   1980
gagcggcggg aggccctgga aacccgtgtc gccgaaggcg aggagcgtct ggctgcggcc   2040
cgcgacgagc agcgcgagct ggaaggcgcg cgggagcagg tgcggcgcca ggtccaggag   2100
gaggggcgcc ggcacggcga gctgaaggcg cagttgtccg cgcagcaggc caaggtcgag   2160
caactggtac tgcgtcgccg ccgtctcgac gaagaagtgg cggaactggc cgagcagcgc   2220
gcgctggaac aggagcaact gagcgaggcg cgcctgaccc tgcaggaagc gctggatagc   2280
atggcgctgg acaccgagcg ccgggaatcc ctgctggcgg agcgtgacgc cctgcgcgaa   2340
cggctcgacc ggattcgcca ggatgcccgc acccacaagg accatgcgca ccagttggcg   2400
gtgcgggtcg gctcgctgaa ggcgcagcac aattccaccc agcaggccct ggagcgcctc   2460
gaccagcagt cggcgcgcct caacgagcgt tgcgaacagc tcaacctcaa tctggaggag   2520
ggggcggcac cgctggaaga gctgcgcatg aagctcgagg agttgctgga gcggcggatg   2580
gccgtcgagg acgaactcaa gcaggcgcgg ctggccctgg aagacgccga tcgcgaactg   2640
cgcgaggtgg agaagcgccg cggccaggcc gagcagcaat cgcaactgct gcgtggccag   2700
ctggagcagc agcgcctgga gtggcagggg ctggtggtgc ggcgcaaagc cttgcaggag   2760
cagctcgccg aagacggcta cgacctgcat acggtactgg ccaacctgcc cctggatgcc   2820
```

```
agcgaacgcg attgggagga gcgtctcgag agtctcgcgg cgcgcatcca gcgtctgggg   2880
ccgatcaacc tggcggcgat cgaggagtac cagcagcagt ccgagcgcaa gcgctacctg   2940
gactcgcaga acgacgacct ggccgaagcg ctggagacgc tggaaaacgt catccgcaag   3000
atcgaccggg aaacccgcaa tcgtttcaag gaaaccttcg accagatcaa tgctggcctt   3060
caggcattgt tcccgaaggt attcggcggc ggtacggcat atctggaact taccggcgaa   3120
gatctactcg ataccggtgt ggcgatcatg gcgcgcccgc cgggcaagaa gaacagcacc   3180
atccacttgt tgtccggcgg ggaaaaggcg ctgaccgcgc tggcgctggt attcgccatc   3240
ttccagttga acccggcgcc gttctgcatg ctcgacgaag tcgatgcgcc attggacgat   3300
gccaacgtcg gacgttatgc gcgattggtg aaggagatgt cggaaaaggt gcagttcatc   3360
tatatcaccc acaacaagat cgccatggaa atggccgatc agttgatggg cgtgaccatg   3420
catgagccgg gctgttcacg gcttgttgca gttgacgtgg aagaggcggt cgcattggct   3480
gaagcctga                                                           3489
```

<210> SEQ ID NO 28
<211> LENGTH: 4254
<212> TYPE: DNA
<213> ORGANISM: Pseudomonas aeruginosa

<400> SEQUENCE: 28

```
atgaacaaga gctatacgct ggtctggaac caggccacag gctgttggaa cgtcgcaagc     60
gaaggtaccc gtcggcgcag caagagcgga cgcggcaagg cgctcgtagt cgccggagcg    120
tcactgctcg gcctgttctg ccaggccccc gccttcgccc tgcccagcgg cgccacggtc    180
gtttcaggcg atgccggatt ccagacatcc accgatggcc ggcatatggt catcgaccag    240
cagagccaca agctgatcac caattggaac gagttcagcg tccgtgccga tgagcgggtc    300
agcttccacc agccgggcca ggacgccgtc gccctgaacc gggtgatcgg ccgcaacggc    360
agcgatatcc aggggcggat agatgccaac ggcaaggtct tcctggtcaa tcccaacggc    420
gtggtcttcg gcaagtccgc ccaggtcaac gtaggcggcc tggtggcttc caccctggac    480
ctggccgaca gggacttcct cgccggcaac taccagttct ccggcgactc cggcgcaacc    540
gtaagcaatg ccggcagcct gcaagccagc gaaggcggca gcatcgccct gctgggcgcc    600
cgggtcagca acgacggctt gatccaggcg caactcggcg acgtggccct gggcgcaggc    660
cagggcatca acctcaattt cgacggcgac ggcctgctca acctgcaggt ggacaagggc    720
tcggtcgacg ctctcgcaca caacggcggc ctcatccgcg ccgatggcgg ccaggtgctg    780
atgagcgccc gcagcgccga cagcctgctc aagaccgtcg tcaacaacca gggcactctc    840
gaggccagga cgctacgcag cgcggaagga cgcatcgtcc tcgacggcgg cgaacagggt    900
accgtgcggg tggccggcaa gcaggacgcc agcgccatcg gcggaggcaa tggcggcctg    960
gtgctgaacc agggcgcgaa cgtcgagata cagcgaaccg cgcaggtgga cacccatgcc   1020
gaccagggcg caaccggcac ctggaggatt ctctcgcacg aggtcagcgt agccgctgtc   1080
ggccaggcaa acgctgccgg tgatggttcc ggccaggtcc atgtagcgca gggcccagcc   1140
ggggccaatg cgtccgatag caacggcgtg accatcgttc agcagcagcc ggccgtcgac   1200
ctcgccgccg gcgccaacgg tacctccgca gtgcagagcc agagcggcgc caacatcggc   1260
tcgggcgcca atggcatcag cgtcgtgcaa agccagaaca gccccaatat cggctcgggc   1320
gccaatggca tcagcgtcgt gcaaagccag aatggcgcca atatcggcgc cggcgcgagt   1380
```

-continued

```
ggcatcagcg tcgtgcagag ccagaacagc cccaacatcg gctcgggcgt caatggcgtg   1440
actgtcgtgc agagccagaa cggtgccaat atcggttcgg gcgcaagtgg catcaccgtt   1500
gtgcaaagcc agaatggcgc aaatatcggt tcaggcgcga gtggcatcag cgtcgtgcag   1560
agccagagcg gccccagcat cggctcgggc gtcaatggcg tcacaatcgt gcagagccag   1620
agcggtgcca acatcggccc cggcgtcagc ggaatcgatg tcgtccagac ccagactctc   1680
cccaacctga gcccaggcgc caatggctcc agcatcgtcc aggtccagac gctacccgat   1740
atcgccgccg acgccggcaa tgtgcatgtc gtgcaggtcc agaccggcgg taacaaggtc   1800
ttcggcaact ccgccaccaa cgtcaggtca cgtaccgttc aggcccggag caacgagaat   1860
gtcggttccg gcctggcgaa tccaagcagc gcgggaaaag gctcgacgtt gcatgccgat   1920
accctggccc gcaacctttc cacaagcaac gtcgaagtgg tcgccacccg gggcaacgcg   1980
catgtcggcg cgccgctgtc ctgggacagc ggcaacggcc tgacgctaac cgccgagcgc   2040
ggggacctca ggatcaatgg cgcgctgacg gcccaggggg aaaacgccag ccttactctc   2100
aatgccgggc agcgccctct ccgtatcgac gacagcctct ctctcactgg ccagggagcc   2160
cgggtcgaat tcaattcgga caagggttat gccctggccg aaggcacccg gatcaccctg   2220
tccggcaaga acgcaggatt ccgcgccaat gggcgggact acagcgtgat ccaggacctg   2280
cagcagttgc gcggcatcga tagggacctg ggcggcagct atgtcctcgg caatcgaatc   2340
gcaggcggca actccagctt cctgtcgata ggcaacgcga gcgccttcgg cggtaccttc   2400
gacggcctgg gcaacaccat cgataatctc gccgtctacg gcaccggcgc ctactccggc   2460
ctgttcagcg tcaaccgggg caccctccgc aacctgaacc tggaacgcat ttccgccgat   2520
ggagcacagg ccacccacta caatgtccag gtcggtagcc tggccgccgt caacctcggt   2580
cgcatcgaca atgtgaacgc cagcgacatc cgtatcgccg cggcctcgaa gctgaacagc   2640
ctcggcgggc tggtcgcact gaacctgggt agtatcgaca acgccagcgc cagcggcacg   2700
ctggtcggca accgccacac ctatgctctg ggcggactcg cagccgaaaa catcagcaca   2760
gccaggggcg tggccagcat ctccaacagc cgggccgatt ttgccatctc cggccagttg   2820
aaggaccatg ccagccacta cggcgcgggg ggcctggtag gcaggaaccg cggcggcctc   2880
atccgcagca gcggcagtca gggaacgctg tcgctgagcg gtcacggaat gaacctggga   2940
ggactggtcg gatacagttc cgccggcgga ctggcggacg tttccgcctc cgtcgacgtc   3000
tcaggcaacg gacagcgcgg cctgtacggt gggctcatcg gcctcaacgt aaacagtggt   3060
attgcccacg ccacggccag cggcaaggtc cggggcacag acgcggaagc actgggcggg   3120
ctgatcggcc ggaacctgaa cgcggccatc aacaacgcca gcgcccatgg cgatgtcagc   3180
ctgcaagccg gtcgctacct gggaggcctg atcggccaca accaggcagg caacctggcc   3240
aacgtcagta ccagcggcaa cctgagtggt gggtcgctgc tccaggccgg cggcctgatc   3300
ggtctcaacg ccaatgcctc gctggtcaat gcctccgcca agggcaatgt cgctacccgc   3360
ggagcagaag cggttggcgg tctgctcgga gaaaacctgt acggctccgt catcaacggt   3420
tccgccagtg gcgaagtcac cgacggcagc ggcaaaaccc tgggtggcct gatagggtcc   3480
aacctcggcg gcaatcattc caacctgaag gcctccgggt gggtaaacgc aggggcgaac   3540
agtgacgtgg gagggctgat cggccacaac cggggcggca accacagcac cctggcggca   3600
tccggcaatg tcaccggggg caagggcagt cgcgtcggcg gactcgtcgg ctataacgat   3660
gccgcctcgc tgacgaacgt ctcggcttcg ggcaacgtca gcgccagtgg ttccagggcc   3720
atcggcgggt tgatcggcag tgacctgcga ggttcgctga tgctcgccag cagtcatgga   3780
```

```
atcgtgaacg acaagaccag ccacaacctg ggagggttgg tcggccgcgg tgaaaacacc   3840

tcgatccgct ccgccaaggc cagcggtgcg gtgagcggag gcgccgggat cagggccggc   3900

ggactggtcg gctccctgga gggctggcag gctctcatcc tgggggcctc ggccggcggc   3960

gatgtgacgg cgggctacga tagctatatt ggcgggctgg tgggcttcag caccgccacc   4020

atcagcggcg cttccgcttc cggcaaggtc ggaggctcgg gtctgctggg cggcctggtc   4080

gcctggaacc aggggaatgt catgggttct tcggccagcg gcaggctgga gccacaaatc   4140

cccaaccaga tccatggcgg actgatcggc atcaattttg gctggcagtc ctggaactcg   4200

gtatacgggg ctgcggcgac cgttccaatg ataggtcgcc actacaacct gtga         4254
```

<210> SEQ ID NO 29
<211> LENGTH: 408
<212> TYPE: RNA
<213> ORGANISM: Pseudomonas aeruginosa

<400> SEQUENCE: 29

```
augccccgug gcgacaagag caaguacagc gacaagcagc agcgcaaggc cgagcacauc     60

gaggagagcu acaaggccaa gggugugagc gagucggaag ccgaggcgcg cgccugggcg    120

acggugaaca agcaguccgg cggcggcgag cgcaagggcg guuccggccg cgccaagagc    180

gagacggcca agcgcgccga ccgcaaggac ucggcccauc gcgccgccca ggcccgcuca    240

gggagaccgg ccaaccgcgg cucggcgagc cguggcaaac gucaaggcag caccucggug    300

agcgagauga cccgcgagga auugaugcag cuggcgcgca agcgcgacau ccgcggucgu    360

ucgacgaugc gcaaggccga acugaucgag gcccuguccc gggccuga                 408
```

<210> SEQ ID NO 30
<211> LENGTH: 417
<212> TYPE: RNA
<213> ORGANISM: Pseudomonas aeruginosa

<400> SEQUENCE: 30

```
augaauaucc ugcguauccc gauguucgua uuggccaugg ccgucucggc ccaugguuuc     60

gcugccaccg cgcagcagga gaagaugacc gccugcaacg ccgaggccac caccaaggcg    120

cucaagggcg acgaacgcaa ggcguucaug agcggcugcc ugaaggccgg cgcgccugcc    180

ggcggcaagg ccaccgccca gcaggagaag augaagagcu gcaacgccga cgccagugcc    240

aagucgcuca agggcgacga acgcaaggcg uucaugagca guugccugaa ggccggcggc    300

agcgccaagg cggcgaccca gcaggagaag augaagaccu gcaacgccga cgccaccgcc    360

aaggcgcuca agggcgacga acgcaaggcg uucaugagca ccugccugaa gaaguga       417
```

<210> SEQ ID NO 31
<211> LENGTH: 426
<212> TYPE: RNA
<213> ORGANISM: Pseudomonas aeruginosa

<400> SEQUENCE: 31

```
auggcuacac gacggaaaac aacaccccag gaaaucgaug auauccagga ccgcaugggu     60

ucgaugcgcg agcucgauuu cgacgagcgc cgccaggcgc guaaggcgcg gaucggcgac    120

gagcggcccg aggccgaggu ggaggccgaa uuuuccucgc ggcggguacg cgaggcgggc    180

cacgcuggcg ggcagccgga cgaggacgau gguuaccagg auaacgucgg cauggacgau    240

cuggcgccgg aaacccugau cgacgaaagc ggcgcccgcu cgccggccga gcgcggcggc    300
```

```
gaaucgcccg cggacaagcg ccugaggguc gugcauggca acgagaucgg agccggccac    360

ggccucgacg aggccgagcu ggcgcgucgu gauccgcucg acgguuccuc cgacgaggaa    420

cgcuga                                                               426
```

<210> SEQ ID NO 32
<211> LENGTH: 453
<212> TYPE: RNA
<213> ORGANISM: Pseudomonas aeruginosa

<400> SEQUENCE: 32

```
augcgacgca ugauccuccc ggccagcuug uugcucgccc ucuccucuuu cgccauggcc     60

gccccgaucu acaaaugggu cgacgccgag ggcgucaccc acuucggcgc acaaccgccg    120

caaggugcgc aagcgaccac ggugaauacc cagaccgccc cgccgccgga caacuucccc    180

cugccccccu cgaccccggc accgaccauc cagcagaaac cggccgaucc cgagcagaag    240

gcgaucgacg acaaggugaa gcagcaagug gcgaaggaag aggccgagcg caagcaguuc    300

ugcgaagaga cccgcaacaa ccucgcgcaa cugaagaaca acccgcgcgu aagggucgac    360

gaaggcaagg gcgaacuccg ucgccucggc gaggaagaac gccaggagcg aaucgccaag    420

gccgaaaagg cgauccagga gaauugccgc uga                                 453
```

<210> SEQ ID NO 33
<211> LENGTH: 714
<212> TYPE: RNA
<213> ORGANISM: Pseudomonas aeruginosa

<400> SEQUENCE: 33

```
auguucaccu cccguugccu gccucuggcc gcagccguca ccgcacuggc gcugcucgcc     60

gguugugcca acaacaaccc cuacgacacg caaagccaaa gccagggugg caugagcaag    120

acggccaagu acggcggacu gggugcgcug gccggcgccg ucgccggcgc ugcgaucgac    180

cacaacaacc guggcaaggg cgcgcugauc ggcgcugccg uugccggcgc ggccgccgcg    240

gguuauggcu acuacgccga caagcaggaa gccgagcugc gucggcagau ggaaggcacc    300

ggcguggaag ugcagcgcca aggugacgac aucaagcuga ucaugccggg caacaucacc    360

uucgccaccg auucggcgaa caucgccccg agcuucuacg cgccgcugaa caaccuggcg    420

aacucguuca agcaguacaa ccagaacacc aucgagauug ucgguuacac cgacagcacc    480

ggcagccgcc agcacaacau ggaccugucc cagcgucgug cgcagagcgu ggccggcuac    540

cugaccgccc agggcgucga cggcacccgc cugagcaccc gcggcauggg cccggaccag    600

ccgaucgcga gcaacuccac ugccgacggu cgcgcgcaga accggcgcgu cgaggucaac    660

cugcgaccgg uuccgggcgc ccagggcccg gcgcagaccc agccgcagua cuga          714
```

<210> SEQ ID NO 34
<211> LENGTH: 1191
<212> TYPE: RNA
<213> ORGANISM: Pseudomonas aeruginosa

<400> SEQUENCE: 34

```
augaagcgac uggcuggacu gaccgcccuc gcccugguua ucggcaacac uuccggcugc     60

ggcuggcugu gggggccgga gggcuauuuc cgcgaccgcg gugacgacua ccucggcgcc    120

cgcgaaacgc cucccaugca auugcccgaa ggggugcaca gcaagccgcu cgauccgcug    180

cugccgauuc cgcugaacgu cgccaccacc cacgaaaaag agggugagua cgagguuccg    240

cguccgcagc cgcuggccaa cgccggcgac aucagcgacu acagccugca gcgcagcggu    300
```

```
gauagccgcu gggucguggc ccagcguccg ccggcggaag ucuggccggu ggcccggcag    360

uucuucgagg agaacgguuu ccgcaucgcc gacgagcgcc cgcagaccgg cgaguucagu    420

uccgacuggc aaucgcuguc gcagcuuucc gcgccgcugg cacgccgccu uagcagccgc    480

gugagcggug ucgagccgga cggccaggca cggguucggg ugcguaucga gcccggcgug    540

caaagcaaua ccagcgaggu cuacgugcuc agccagaccc gcgccgccgg ugacaccagc    600

agcccgagcu ggccgagcaa gucgguggcg ccgagccucg acgcggcgcu gcucgacgag    660

auggucgcga gcauggcgcg cagcgccgag cagggcggcu cggucucccu gcuggcagcc    720

aacucgaucu acgacacgcc cggcaccuuc gaguugagca aggacggcag cggcaacccg    780

gugcugaccu ugcaguccga cuucgaccgc uccuggguca gcgucgggcg ugcccuggau    840

aacgccgaua uccgcgucga cgaccucaac cgcagccuug gcguguacua cgugaacauc    900

gccgaagggg cgaagaagcc cgacgaagac aagcccgggu ucuucagucg ccuguucggc    960

ggcggcgaga agaccaagga agaggaagac gccaaggcgc agcgcuacca gguccgccug   1020

accaccguca gcgacgccgu gcaggucacc gucgacaagg acaucaacac cucugcgccg   1080

gccgaugucg cgcaaaacgu acuggaaaaa cuccaggaga gcaugcgcaa ugcgguucgc   1140

gguucugggc agcggaagcc ggggcaauuc ggccuuggug agcaguucug a            1191
```

<210> SEQ ID NO 35
<211> LENGTH: 1632
<212> TYPE: RNA
<213> ORGANISM: Pseudomonas aeruginosa

<400> SEQUENCE: 35

```
augauccgcc uguucugcag ccugcuucuc gcgcuccucu gcgucuccgc ccacgccagc     60

uucagcgcca gcgucgaccg cgcccgccug accgaagggg aaagcgucga acugacgcug    120

gaaucggacg acccgacccu cuucggcaag cccgaccuga gcccgcugga cgcccucuuc    180

gagguccucg gcacgcgcca ggucaaccgu cucgccacac agaacggccg ggcccaggcc    240

accacccgcu ggaucgucac ccuccugccg aagcagagcg gcuacguggc gaucccgccg    300

aucagccucg gcgccagcag cacccagccg aucaggcugc acguacugga ggcgcgcgac    360

cgcgccaaga gcagcaagcu ggcgccgguc uucaucgaug ccagcgucga ccaggagacg    420

gucuacgugc aggcccaggc gauccucacc cugcgcaucu accacucggu gucgcuauac    480

gacgacagca gccugacccc gcuggcgaug aacgacgcga aggucgaaca gcucggcgag    540

gcgcgcaccu acgagaagga gaucaacggc auccgccacg gcgugaucga ggugcgcuac    600

gcgaucuucc cgcagaagag cggcacccug gagauuccug cgcaagccuu cagcgcgacc    660

cuggucgacc guggcaguga cgacuacaac cccuucggcc cgcgccccgg ccggcagaug    720

cgggugacuu cgccgagcau cccgcugcag guccggccca agccugccga cuauccggcc    780

gacgcgcccu ggaugccggc ccgcgcgcug agcaucagcg aaagcuggag cccgcagccg    840

gagcaggcgc aggucggcga aucgcugacg cgcaaugugc ugcugaaggu cgaggggcuu    900

uccggcaccc agcuuccgcc guugccgcug cccgacgugc aaggccugcg gcgcuacccg    960

gaccaaccgc aguuggccga ccagagcacc gaccagggcc ucaucggcag ucgcgaggaa   1020

cgcgaggcgc uggugcccga gcaggccggg cgcaucgagu ugccggcgcu cgaagugguc   1080

ugguggaaca cccgcgaaga ccgccuggag cgcaccagcc ugccaccgcg cacccuggaa   1140

guggccgccg cgccgcaggc cgaggcggag ccgccggcgg cggcgcugcc gcucggcgaa   1200
```

cgccuggagc cgacgcucug gcccuggcaa cuggcuaccg ccgugcuggc ccugaccacc 1260
cugcucggcu ucggccucug guggcgcgcc cgccagcugc cggcggugau ccgcgccgcg 1320
gccaacggcc cgagcagccg cagccugcuc gacgagcugc gccgcgccug ccuggccaac 1380
gauccccagg cgacccgcca ggcccuggac gccugggccc gucagcaacc cgauacccug 1440
gccgacaugg cggcccgcuu cguaccgcug uccgacgccc uggauggccu caacggcgcg 1500
cuguacagcg agagcggcca uuccuggcag ggcgaggacc uguggcgggc gauccgcgcc 1560
cugcccacca cggaacaagc gccggcggga gcggucgaca auggcggccu gccaccgcuc 1620
uauccgcgcu ga 1632

<210> SEQ ID NO 36
<211> LENGTH: 1920
<212> TYPE: RNA
<213> ORGANISM: Pseudomonas aeruginosa

<400> SEQUENCE: 36
auguccuuuu cuucccucgg acucuccgag gcgcuugccc gcgcugugga ggcugcgggc 60
uacagccagc ccacucccgu gcaacagcgg gcgauucccg ccguguugca aggucgcgac 120
cugaugguug cggcacagac cggcaccggc aagaccggug guuucgcccu gccgguacug 180
gagcgccugu uccccgccgg ucaucccgac cgcgaacacc gccacggccc gcgccaggcg 240
cgcgugcugg uacugacccc gacccgugag cuggccgccc aggugcauga cagcuucaag 300
gucuacgccc gcgaccugcc gcugaacagc accugcaucu ucggugggu uggcaugaac 360 ccgcagaucc aggcccuggc caagggcguc gacguacucg ucgccugccc cggccgccug 420
cucgaccugg ccgggcagaa caaggucgac cugucccacg uggaaauccu cguccucgac 480
gaagccgacc gcaugcucga caugggcuuc auccacgaug ugaagaaggu ucucgccaag 540
cugccgccca agcgccagaa ccugcuguuc ucggcaaccu ucucgaaaga caucgucgac 600
cucgccaaca agcuccugca caacccggaa cgcaucgagg uaacgccgcc gaacaccacg 660
gucgagcgca ucgagcaacg cguguuccgc cugccggcuc cgcagaagcg cgcccugcug 720
gcgcaccugg uaaccgucgg cgccugggaa caggugcugg ucuucacccg uaccaagcac 780
ggcgccaacc gucucgccga guaccugacc aagcacggcc ugccggccgc cgcgauccau 840
ggcaacaaga gccagaacgc gcggaccaag gcgcuggccg acuucaaggc caacgacgug 900
cgcauccugg uggcgaccga caucgccgcc cgcggccugg auaucgacca guugccccau 960
guggucaacu acgagcugcc caacgucgag gaagacuaug uccaccgcau cggccguacc 1020
ggccgagccg gacgcagcgg cgaggcgauc ucgcuggugg cgccggacga agagaagcug 1080
cucaaggcca ucgagaagau gaccagacag cguauucccg auggcgaugc ccaggguuuc 1140
gaccccgagg ccgugcugcc cgagguggcc cagccggagc cccgcgaagc gccgcagaag 1200
cagccgcgcc gcgacaagga acggcgcagc agccgcgagc gcaagccgaa agacgcccag 1260
gcgagcaacc ccgacagcaa ugucgcugcg gcccaggacg guaccgagaa gccggcugga 1320
aagcgccgcc gucgcggugg caagaacaag gaaaaccgcg aggccggcca agcgcagcag 1380
ccgcggcaga gccgcgaagc gcguccggcc aagcccaauc ggccgccgga agucgacggu 1440
aaucgcgauc cggaagaguu ccucgacgac gacuucgaca auuucggcaa ccgcgccgac 1500
uacgucagcc ccuaccaggg ccaggaaaac aagggacgcg gacgccgcgg uggccagcag 1560
aaaccccagg gcggcaccgg ccagcagggu cguggccaag gccagggcca agcucgcggc 1620
aagagccagg gcgccgcuca aggcggcgcu cgcggucagg gugccggcca gggcaaggcg 1680

```
aagaaaccgc gcgccggcaa gccgcgcggc cagggucgcg agaaugccuc gcggaugagc   1740

gacgcgccgc ugcgcgagcc guccgaguau ggcaccggca agcagccgag ccgccagccg   1800

guggugauca acaagcgcga ccuggugcgc auggaucgcu uccccaccgc cgagcagcuc   1860

gacgagcugg aaccgcggcg caagggcgag cgccccgcac ugcugacccg caaccgcuaa   1920
```

<210> SEQ ID NO 37
<211> LENGTH: 2028
<212> TYPE: RNA
<213> ORGANISM: Pseudomonas aeruginosa

<400> SEQUENCE: 37

```
augccugcuu cuuucccgcg ccucggcuug cucggcgcac ugugcuccau cguuccccug     60

cuccaugcca gcgaaccgac cacggacgcu gcgcucaucg aaaaaggccg cuacguggcc    120

cagcucggcg acugcaucgc cugccauacc ggcccgcagg gcgcgccgau ggccggcggc    180

cuggagcuga agacgccaau ggguaccauc uacucgacca acaucacucc cgaccgggag    240

accggcaucg gccgcuacag cuucgaagag uucgaccgcg ccaugcgcaa gggggugacc    300

gccgagggag ugaaucucua uccggcgaug cccuacccgu ccuacgccaa gaucagcgaa    360

gaagacaugc gugcacugua cgccuaccug augcacggcg ugcaacccgu cacccaggcg    420

aauacgccga gcgcgaugag cuggccguuc aaccagcgcu ggggccuguc gcuguggaac    480

ugggcguucc ucgacgacgc gccguucacc cccuccagcg acgcggaccc ggugaucaac    540

cgcggcgccu accugguaca ggggcucggc cacugcggcg ccugccauac uccgcgcggc    600

aucgccuucc aggaaaaagc caugagcgaa gccggucguu ccgggcaguu cuaccucgcc    660

ggagaaaccg ucgaacaaug gcaagcccug agccugcgca accuguggac gguggaggac    720

accgugcagu ugcugaagac cggcagaac cgcuucgcca cggugucgg cagcaugacc    780

gaugucaucc accacagcac ccagcacuuc agcgacgacg aucugcuggc caucgccagc    840

uaccugaagu cccugccggc cggcaaggac gaccugccca ugcccgacag cgaacgccca    900

cuggcagcac cggucgaccu guacagcucg cggggcgguc ucggcuacgc gcaguucugc    960

uccgacugcc accgcaagga cggcagcggc gucccaggca uguucccgcc gcuggccggc   1020

aaccccacgg ucgcuucggc caacccgagc acgcuacugc auaucacccu uaccggcugg   1080

aaaaccgcgc agaccgcaac ccacucgcgg gucuacacca ugcccggcuu cgcccagcug   1140

gaagaccgcg aaaucgccga gauccucagc uucguccgca gcaguugggg caaccagggg   1200

ucgucgaucg augccggcca ggugaagaaa cugcgccagc ggaucgaggc cggcaacggc   1260

ccggccacga ccuucgucuc uccacgccug gcggacaugc ucgcggcgcc gaacgccgaa   1320

cagguggu ac gcggcaugcg ccugcaccug gagacccgcg agcugcugcc ggcgaacguc   1380

ggcaaccagu ugcacugcac caguugccac cugaacgccg gaaccguagc cgacggcucg   1440

cccuucgucg gcgucucggc guucuucccc agcuacgcgc cccgggcggg caaggucauc   1500

ggccuggagg aacgcaucaa cggcugcuuc cggcgcucga ugaacgguaa gccucugccg   1560

ccggacucug ccgacaugca ggcgauggug gccuacuucg acuggaugaa gaacaacacc   1620

cggccgcagg acaaggucgc cggccgcggc gucggcaagg ucgacccggc gcugaagccc   1680

gacccggaga acggccgcaa ggucuacgcc cgacaaugcg uggugugucau uggcgagaau   1740

ggcgaggggc ugaggaacag ugccggcgag augcucuucc caccgcugug gggcgacgag   1800

ucguucaaua ucggcgccgg cauggcgcgg accuucaccg cugccgccuu cgucaagcac   1860
```

```
aacaugccga ucggcuucca ggaacgcuuc ccgcucggcc agggcggccu cagcgaccag   1920

gacgcagugg acgucgcgga guauuuuucg caccagccgc gcccggacuu cccggacaag   1980

aucaaggacu ggccgaagga caagcguccg cuggaugccc gcuacuga                2028
```

<210> SEQ ID NO 38
<211> LENGTH: 2049
<212> TYPE: RNA
<213> ORGANISM: Pseudomonas aeruginosa

<400> SEQUENCE: 38

```
augcccggua aagccuugcg ugucauguug ugugccuggu cgugccuguu ggccgggcag     60

gcgagcgccc ugggaguggg agacaucauc cugcauucgg cgcucaacca gccgcuggau    120

gcggauaucg aacugcucga cgucggcgau cucggcgcgg acgagaucga gguccgccug    180

gcgggcgccg acgucuucgc cgcggccggg guggaacgcu ugcaguuccu caacgagcug    240

cguuucaguc cggugcucca ggggcgcggu ggcaaucgca uccauguguc cucgauccga    300

ccggugcagg agcccuaccu gaauuuccug guggaggugg cccgccccaa cggccgcauc    360

guccgcgaau ucaccguacu gcucgauccg cucgguuaua cgccgcgcau gcuuccggcc    420

gcgcgcagcg ggaucgagcc gcagcggcaa uccucgacgc cggugccugc gccgcguagu    480

gccgcggucg ucguagaccc ggcacugcug gagccgggcg acgaauaccu ggcucgcccc    540

agcgacaacc ucugggccau cagcggacgc cugcguggug ccggcaacgc cgaucgcgcg    600

caacucaugg aggcucugua ccagcucaau ccgcaggccu ucgucaaugc cgaccggcac    660

cggcucaagg ccggcgcgcg ccugcgccug ccggccggcu accagccgga gcgaggcgcg    720

cccggcgccg ugaaggaggc ggccguggaa guccugccgc cagccgaugc cgccguggug    780

gaaaacgcuc cggcggcucu cgucgaggcg cagcgccagg cggaugccga ggccgaggcg    840

uuggcccggc aacgggagga acugagccag cggauggacg aucugcaacg ccaguugcag    900

gccuugcagg aacaacugca gcagcgcgau caccaggucg ccgaacugca acagcaacug    960

gcccggcgcc aggcggugcg gcccgcggcg ccgccgccug ccgcggccgc gccuucgguu   1020

gcgcaaccgg uugaaacgcc gacggacucg caguacuggc gcuggaugau cguccugcug   1080

cugguccucg cucugcucgg cguguugcug uugcgucgcc gccgcgaaga ggcuccuguc   1140

ccggcggucg aaccgaagcg ccgggucgcc cugaaccugc cgcugcggcg ugcgccgcgc   1200

cccccggcgg ccgcaccggc gccggcaaag gucgaagaac aggccaggcc gccggucgcc   1260

gcucccucca gcccgccgcc gucuccuccg ccugcuccgg ccgccgcucc gcgcgccgcc   1320

auggcugcgg cggacaagcu ggacggcgcc gacaucuaua ucgccuacgg ucgcuacgga   1380

caggcccgcg accugcugcg ucagguacuc gccgagcagc cgcagcgccu gagcgcgcgg   1440

augaagcugu ugcuggugcu ggcugagcug ggcgaugcgg ccggcuucga cgcgcuggcc   1500

gaggaaaccc uggccagugg cggcaacccg gaggccaucg acgaguugcg cggacgcuac   1560

ccggcgcugc uacagaugcc ggcgaccgag acgccggcgg caacaaccaa ggacgacgac   1620

uggagcgacc ugccgcuggc cgagucgccc guuuugcagc aaccggaugc gaccucgggc   1680

gccgacggcu ucggcgaccu caaccucgau cucgaucucg acuggggcgc ccuggagaau   1740

ccccuggaca accccgaccu gccgcgccgc gccgcugccg gcaaggcgga accggcggag   1800

gagccccugg cguucgagag caaucuccau gaacugccgg augucgccga guacgaacac   1860

cucgaacucg accagccaga gccggccacg gugccgccgg aggaggccuc ggccagccug   1920

gaccgggccc gcgccugcau cgacagcggc gaucucgacc aggccagccg cauccugcgc   1980
```

cugguggugg cgcacggcga cccguggcag aaggccgagg cgcgcgaguu gcuggcacug 2040
aucgccuga 2049

<210> SEQ ID NO 39
<211> LENGTH: 2064
<212> TYPE: RNA
<213> ORGANISM: Pseudomonas aeruginosa

<400> SEQUENCE: 39
auguccucuu ccggccuuuu cccuucccgu ccgcucuggc cucucacgcc acuggcgcug 60
gccugccuga ucguuucggg ggaaacgcuc ggcgccgacg gccgccccag cgaauugccc 120
ucccagguga ucaccgccaa cccgcugggc aacgaaucuc ccgccacgcc cagcagcgug 180
cucgaaggcg acgagcugac ccugcgacag aaaggcagcc ucggcgaaac ccucaacggc 240
cugcccgggg uguccuccac cuacuucgga ccgggcgcca gccgaccggu gauccgcggc 300
auggacggug aucgcauccg ccugcugcgc aacggcgucg gugcgcucga cgccucgucg 360
cuguccuacg accacgcggu gccggaagac cccaacagcg ucgagcgccu ggaaguggua 420
cgcggcccgg ccgcccugcu cuacggcggc aaugccaucg gcggggugguu gaacagcuuc 480 gacaaccgca uccccagcga acccgucgac ggcauccacg gcagcggcga acugcgcuac 540
ggcggcgccg acaccacccg uagccgcucc ggcgcacugg aggccggcga cggcaacuuc 600
gcccugcacg uggacgccgc cagccgcgag uucaacgacg ucaggauucc cggcuacgcc 660
cauuccagcc gccagcggca gaucgacggc gacaccggca agcaucgggu gcagaacagc 720
gacggccgcc aggacggcgg cgccgucggu ggcuccuauc acugggagca cgguuacgcc 780
ggccucuccu acagcggcua cgacagcaac uauggcucgc cggccgagga cgacgugcgc 840
cugaagaugc agcaggaccg cuacgccuuc gccuccgaga uccgcgaccu cgaaggcccg 900
uucaccucgc ugaagcugga cgccgccuau accaaguacg agcacaagga aaucgaggac 960
ggcgagaccg gcaccaccuu caagaacgaa ggcuacgaag gccgcaucga ggcccgccac 1020
cgcccgcucg gcccgcugaa cggggugguc ggcgcgcagu ucgccaacag ccgcuucucc 1080
gcccucggcg aggaagccuu cgugccgcac acggaaaccg acagcgccgc gcuguucgcc 1140
cuggaggaau ggaagcucag cgaccgccuc gaccucagcu ucggcgcccg ccuggagcac 1200
acccgcgugg accccgacgc caagggcaac gagcgcuucg ccgagaacga cgguucgcag 1260
agcuucacca ccggcagccu guccaccggc gcgguguaca agcugacgcc gaucuggucg 1320
cuggccgcca cccucagcua caccgagcgc gccccgaccu ucuacgagcu guacgccaac 1380
gguccgcacg ccgccaccgg uaccuacgag guaggcgaug ccgacgcgga caaggaaaag 1440
gcggucucca ccgaccucgc ccugcgcuuc gacaacggcg ugcacaaggg cagcgucggg 1500
guguucuaca gccgcuucuc caacuacauc ggccugcucg ccagcggucg ccaucgcaac 1560
gaggaaggcg aaguggucgc cgccggcgau gacgaggcgc ugccggaaua ccucuacagc 1620
ggcguucgcg cggacuucua cggcgucgag gcgcaggacc gcauccaccu gcuggaaagc 1680
ccguacggca acuucgaccu ggaacucucc ggggacuaca cccgcgccaa gaacaaggac 1740
accggcgaac cgcugccacg caucgccccg cugcgccuga acaccgcgcu gaucugggag 1800
uugcagcagu ggcaggcgcg ggucgacguc gaacacgccg ccucgcagca ccgcgugccg 1860
gaggaagaac ucuccaccga cggcuacacc acccucggcg ccagccucgg cuacaacuuc 1920
gaccucggcg agagccgcug gcuggccuuc gucaagggca ccaaccugac caaccagacc 1980
gugcgcuacg ccaguucgau ccugcgcgac cgggugccgg cggcgggacg cggcaucgag 2040
gcggggguga agguggcguu cuga 2064

<210> SEQ ID NO 40
<211> LENGTH: 2412
<212> TYPE: RNA
<213> ORGANISM: Pseudomonas aeruginosa

<400> SEQUENCE: 40
augaggcaau cagcuuucca ccaugcccgg cgucguuggc cuguacuggg cguggcgcug 60
ggcgcgcuac uggucgcggc guguagcgag acgccgaagg uccccggcgu gccccccggcc 120 gacgaggaag ucggucggcc gcugagcagu guccgcuccg gugcgccguu gcgcagcgcc 180
gacguccgcg agcggcccca ggccgagcag gcccgccgcg cgcugagugc cggacgcggc 240
guggcgcgcu ccggugggcgu ggcuccgguc ucagcgacag cggccgaacu cggcgagcag 300
ccggucagcc ugaauuucgu cgauaccgag guggaagcgg uggugcgcgc gcugucgcgc 360
gccaccggcc ggcaguuccu ggucgacccg cgggugaagg gcaagcugac ccugguuucc 420
gaaggccagg ugccggcgcg caccgccuac cgcaugcuca ccagcgcccu gcgcaugcag 480
ggcuucagcg uggucgacgu cgacggggguc agccaggugg ugccggaggc cgacgccaag 540
cugcucggcg ggccggucua cggcgccgac cggccggcgg ccaacggcau ggucacgcgg 600
accuuccgcc ugcgcuacga gaacgcggug aaccugaucc cgguacugcg cccgaucguc 660
gcgcagaaca acccgaucaa ugccuauccg gggaacaaca ccguggugggu caccgacuac 720 gcggaaaacc ucgaucgggu cgccgggauc aucgccagca ucgacauccc cagcgccagc 780
gacaccgacg uggugccgau ccagaacggu aucgcggugg acaucgccag caccgucucc 840
gaacugcucg acagccaggg cagcggcggc gccgagcagg gccagaagac cguggugcuc 900
gccgacccac gcuccaacag caucgugauc cgcucgccga gccccgagcg cacgcaauug 960
gcgcgcgacc ugaucggcaa gcuggacagc gugcaaagca aucccggcaa ccuccaugug 1020
gucuacuugc gcaacgccca ggcgacccgc cuggcccagg cccugcgcgg gcugaucacc 1080
ggcgacagcg gcggcgaggg caacgagggc gaccagcagc gcgcgcgccu gagcggcggc 1140
ggcaugcucg guggcggcaa cagcgguacu gguagccagg gccuggggag cagcggcaau 1200
accacgggca gcgguuccag cggguugggc ggcagcaacc gcagcggcgg cgccuauggu 1260
gcgaugggca gcggccaggg cggcgccgga cccggugcga ugggcgagga gaacucggcg 1320
uucuccgccg gcggggguaac cguacaggcc gacgccacca ccaacacccu gcugauuucc 1380
gcacccgagc cguuguaccg caaccuccgc gaagucaucg accugcucga ccagcgccgc 1440
gcccaggugg ugaucgaaag ccugaucguc gaggucagcg aagacgacuc cagcgaguuc 1500
ggcauccagu ggcaggccgg caaccucggc ggcaacggcg uguucggcgg ggucaacuuc 1560
ggccagucgg cgcugaacac ggccggcaag aacaccaucg acguguugcc caaggggcuc 1620
aacaucggcc ugguggaugg caccguggac auccccggga ucggcaagau ccucgaccuc 1680
aaggugcucg cccgggcgcu gaagagccgc ggcggcacca acguccuguc gaccccgaac 1740
cugcugaccc uggacaacga gucggcgagc aucauggucg gccagaccau acccuucguc 1800
agcggccagu acgucaccga cggcggcggu accagcaaca acccguucca gaccauccag 1860
cgcgaggacg ucggccugaa gcugaacauc cguccgcaga ucuccgaggg aggaacgguc 1920
aagcucgacg ucuaccagga ggucagcagc gucgacgagc gcgccagcac cgccgccggg 1980
guggucacca acaagcgcgc gaucgauacc agcauccucc ucgacgacgg ccagaucaug 2040

-continued gucc ucggcg gccuguugca ggacaacgug caggacaaca ccgacggcgu ucccggacuc 2100
uccagccucc ccggcgucgg cucgcuguuc cgcuaccaga agcgcucgcg gaccaagacc 2160
aaccugaugg ucuuccugcg ucccuacauc guccgcgacg ccgccgccgg ccgcagcauc 2220
acccucaacc gcuacgacuu cauccgccgc gcccagcagc gcgugcagcc gcgccacgac 2280
uggagcgucg gcgacaugca ggcuccggug cugccgccgg cgcagcaggg caucccgcag 2340
gccgccuacg acuugcgccc gagcccgcgg ccgcugcgcg cgguaccguu gggcgaggcg 2400
gcgccgcuau ga 2412

<210> SEQ ID NO 41
<211> LENGTH: 3489
<212> TYPE: RNA
<213> ORGANISM: Pseudomonas aeruginosa

<400> SEQUENCE: 41
augcgccuga agagcaucaa gcuggcgggg uucaaguccu ucgucgaucc gaccacggug 60
aacuucccca gcaacauggc ggcaguggua gggccgaacg gcugcggcaa gucgaacauc 120
aucgacgcgg ugcgcugggu gaugggcgaa agcucggcga agaaccugcg cggcgagucg 180
augaccgaug ucaucuucaa cggcucgaau acccgcaagc cggugagcca ggcgagcauc 240
gagcugaucu ucgacaacgc cgagaccacc cuggugggcg aauacgccca guacgccgag 300
auauccauuc gccggcgggu cucgcgggau gggcagaaca ccuauuuccu caacggcacc 360
aagugccggc ggcgcgacau caccgacauc uuccucggca ccggccuggg gccgcgcagc 420
uacucgauca ucgaacaggg caugaucucc aagcugaucg aggcgcgucc ggaagaccug 480
cgcaacuuca ucgaggaagc cgcgggcauu uccaaguaca aggagcgccg ccgcgaaacc 540
gaaagccgca uccgucggac ccaggaaaac cuggcacgcc ucaccgaccu gcgcgaagag 600
cuggggcggc aacuggaacg ccugcaccgg caggcccagu cggcggaaaa auaccaggaa 660
cacaaggccg aggagcgcca gcucaaggcc cagcugggug ccgugcgcug gcgcgaccug 720
aacgagcagg ucggucagcg cgagcggguc aucggcgacc aggagaucgc cuucgaggcc 780
cugguggccg agcagcgugg ugccgaugcc ggcaucgaac ggcugcgcga cggccaucac 840
gaguuguccg aacgcuucaa ccaggugcag gcacgcuucu auucggucgg cggcgacauc 900
gcccgggucg agcagagcau ccagcauggc cagcagcgcc agcgccaguu gcaggacgac 960
uugcgcgaag ccgaacggac ccgccaggaa accgaaucgc accucgggca ugaccguacc 1020
uugcucgcga cccuggccga ggaaauggcc augcucgcac cggaacagga acucagcgcg 1080
gccgccgcgg aagaagcggg caucgcccug gaacaggccg agcagggcau gcaggccugg 1140
cagcagcagu gggaugccuu caaccagcag agcgccgaac cccgccgcca ggccgaggug 1200
cagcagucgc gcauccagca ccuggagcag agccuggagc gccugcagga ucgcgagcgg 1260
cgccugcagg aggagcgugg ccaguuggcg gccgaccccg aggacgcggc gauccucgaa 1320
cucaacgaac agguggcgau cgccgaacug gcccuggaag aacugcaauu gcaggagcag 1380
ggccaagccg agcgacucga acaauugcgc caggaauugc agcagcuggc cgccgaacag 1440
caccaggcgc agggcgaguu gcagcgccug aacgggcgca ucgcuucgcu ggaggcccug 1500
cagcaggccg cucucgaucc cggacagggc gccuuggagu gguugcgcga gcagggccug 1560
gaacaacguc cgcgccucgc cgaaggcuug cgugucgagc cggguuggga gcuggcggug 1620
gagaccgugc ucggcgcgga ucugcaggcg gucuugcugg acggcuucga cgggcucgcc 1680

```
cuggccggcu ucggcaaggg cgagcugcgc cugcucagcc ccgcucgcgg agccgcgacg   1740

gcggccgguu cgcugcugga caagguccgc gccgacgccg accugagucc cugguuggcc   1800

cgggugaaac cgguggagac ccuggaacag gcgcucgccc agcgcggcgc ccuggacgac   1860

ggcgagagcc ugaucagucg cgauggcuac ugggucggcc ggcacuuccu gcggguccgg   1920

cgcagcgacg aggcccaggg cggcaugcuc gcccgcgccc aggaacugga ggcguugcag   1980

gagcggcggg aggcccugga aacccguguc gccgaaggcg aggagcgucu ggcugcggcc   2040

cgcgacgagc agcgcgagcu ggaaggcgcg cgggagcagg ugcggcgcca gguccaggag   2100

gaggggcgcc ggcacggcga gcugaaggcg caguuguccg cgcagcaggc caaggucgag   2160

caacugguac ugcgucgccg ccgucucgac gaagaagugg cggaacuggc cgagcagcgc   2220

gcgcuggaac aggagcaacu gagcgaggcg cgccugaccc ugcaggaagc gcuggauagc   2280

auggcgcugg acaccgagcg ccgggaaucc cugcuggcgg agcgugacgc ccugcgcgaa   2340

cggcucgacc ggauucgcca ggaugcccgc acccacaagg accaugcgca ccaguuggcg   2400

gugcgggucg gcucgcugaa ggcgcagcac aauuccaccc agcaggcccu ggagcgccuc   2460

gaccagcagu cggcgcgccu caacgagcgu ugcgaacagc ucaaccucaa ucuggaggag   2520

ggggcggcac cgcuggaaga gcugcgcaug aagcucgagg aguugcugga gcggcggaug   2580

gccgucgagg acgaacucaa gcaggcgcgg cuggcccugg aagacgccga ucgcgaacug   2640

cgcgaggugg agaagcgccg cggccaggcc gagcagcaau cgcaacugcu gcguggccag   2700

cuggagcagc agcgccugga guggcagggg cugguggugc ggcgcaaagc cuugcaggag   2760

cagcucgccg aagacggcua cgaccugcau acgguacugg ccaaccugcc ccuggaugcc   2820

agcgaacgcg auugggagga gcgucucgag agucucgcgg cgcgcaucca gcgucugggg   2880

ccgaucaacc uggcggcgau cgaggaguac cagcagcagu ccgagcgcaa gcgcuaccug   2940

gacucgcaga acgacgaccu ggccgaagcg cuggagacgc uggaaaacgu cauccgcaag   3000

aucgaccggg aaacccgcaa ucguuucaag gaaaccuucg accagaucaa ugcuggccuu   3060

caggcauugu ucccgaaggu auucggcggc gguacggcau aucuggaacu uaccggcgaa   3120

gaucuacucg auaccggugu ggcgaucaug gcgcgcccgc cgggcaagaa gaacagcacc   3180

auccacuugu uguccggcgg ggaaaaggcg cugaccgcgc uggcgcuggu auucgccauc   3240

uuccaguuga acccggcgcc guucugcaug cucgacgaag ucgaugcgcc auuggacgau   3300

gccaacgucg gacguuaugc gcgauuggug aaggagaugu cggaaaaggu gcaguucauc   3360

uauaucaccc acaacaagau cgccauggaa auggccgauc aguugauggg cgugaccaug   3420

caugagccgg gcuguucacg gcuuguugca guugacgugg aagaggcggu cgcauuggcu   3480

gaagccuga                                                           3489
```

<210> SEQ ID NO 42
<211> LENGTH: 4254
<212> TYPE: RNA
<213> ORGANISM: Pseudomonas aeruginosa

<400> SEQUENCE: 42

```
augaacaaga gcuauacgcu ggucuggaac caggccacag gcuguuggaa cgucgcaagc     60

gaagguaccc gucggcgcag caagagcgga cgcggcaagg cgcucguagu cgccggagcg    120

ucacugcucg gccuguucug ccaggccccc gccuucgccc ugcccagcgg cgccacgguc    180

guuucaggcg augccggauu ccagacaucc accgauggcc ggcauauggu caucgaccag    240

cagagccaca agcugaucac caauuggaac gaguucagcg uccgugccga ugagcggguc    300
```

-continued agcuuccacc agccgggcca ggacgccguc gcccugaacc gggugaucgg ccgcaacggc 360
agcgauaucc aggggcggau agaugccaac ggcaaggucu uccuggucaa ucccaacggc 420
guggucuucg gcaaguccgc ccaggucaac guaggcggcc ugguggcuuc cacccuggac 480
cuggccgaca gggacuuccu cgccggcaac uaccaguucu ccggcgacuc cggcgcaacc 540
guaagcaaug ccggcagccu gcaagccagc gaaggcggca gcaucgcccu gcugggcgcc 600
cgggucagca acgacggcuu gauccaggcg caacucggcg acguggcccu gggcgcaggc 660
cagggcauca accucaauuu cgacggcgac ggccugcuca accugcaggu ggacaagggc 720
ucggucgacg cucucgcaca caacggcggc cucauccgcg ccgauggcgg ccaggugcug 780
augagcgccc gcagcgccga cagccugcuc aagaccgucg ucaacaacca gggcacucuc 840
gaggccagga cgcuacgcag cgcggaagga cgcaucgucc ucgacggcgg cgaacagggu 900
accgugcggg uggccggcaa gcaggacgcc agcgccaucg gcggaggcaa uggcggccug 960
gugcugaacc agggcgcgaa cgucgagaua cagcgaaccg cgcaggugga cacccaugcc 1020
gaccagggcg caaccggcac cuggaggauu cucucgcacg aggucagcgu agccgcuguc 1080
ggccaggcaa acgcugccgg ugaugguucc ggccaggucc auguagcgca gggcccagcc 1140
ggggccaaug cguccgauag caacggcgug accaucguuc agcagcagcc ggccgucgac 1200
cucgccgccg gcgccaacgg uaccuccgca gugcagagcc agagcggcgc caacaucggc 1260
ucgggcgcca auggcaucag cgucgugcaa agccagaaca gccccaauau cggcucgggc 1320
gccaauggca ucagcgucgu gcaaagccag aauggcgcca auaucggcgc cggcgcgagu 1380
ggcaucagcg ucgugcagag ccagaacagc cccaacaucg gcucgggcgu caauggcgug 1440
acugucgugc agagccagaa cggugccaau aucgguucgg gcgcaagugg caucaccguu 1500
gugcaaagcc agaauggcgc aaauaucggu ucaggcgcga guggcaucag cgucgugcag 1560
agccagagcg gccccagcau cggcucgggc gucaauggcg ucacaaucgu gcagagccag 1620
agcggugcca acaucggccc cggcgucagc ggaaucgaug ucguccagac ccagacucuc 1680
cccaaccuga gcccaggcgc caauggcucc agcaucgucc agguccagac gcuacccgau 1740
aucgccgccg acgccggcaa ugugcauguc gugcaggucc agaccggcgg uaacaagguc 1800
uucggcaacu ccgccaccaa cgucagguca cguaccguuc aggcccggag caacgagaau 1860
gucgguuccg gccuggcgaa uccaagcagc gcgggaaaag gcucgacguu gcaugccgau 1920
acccuggccc gcaaccuuuc cacaagcaac gucgaagugg ucgccacccg gggcaacgcg 1980
caugucggcg cgccgcuguc cugggacagc ggcaacggcc ugacgcuaac cgccgagcgc 2040
ggggaccuca ggaucaaugg cgcgcugacg gcccaggggg aaaacgccag ccuuacucuc 2100
aaugccgggc agcgcccucu ccguaucgac gacagccucu cucucacugg ccagggagcc 2160
cgggucgaau ucaauucgga caaggguuau gcccuggccg aaggcacccg gaucacccug 2220
uccggcaaga acgcaggauu ccgcgccaau gggcgggacu acagcgugau ccaggaccug 2280
cagcaguugc gcggcaucga uagggaccug ggcggcagcu auguccucgg caaucgaauc 2340
gcaggcggca acuccagcuu ccugucgaua ggcaacgcga gcgccuucgg cgguaccuuc 2400
gacggccugg gcaacaccau cgauaaucuc gccgucuacg gcaccggcgc cuacuccggc 2460
cuguucagcg ucaaccgggg cacccuccgc aaccugaacc uggaacgcau uuccgccgau 2520
ggagcacagg ccacccacua caauguccag gucgguagcc uggccgccgu caaccucggu 2580
cgcaucgaca augugaacgc cagcgacauc cguaucgccg cggccucgaa gcugaacagc 2640

```
cucggcgggc uggucgcacu gaaccugggu aguaucgaca acgccagcgc cagcggcacg   2700

cuggucggca accgccacac cuaugcucug ggcggacucg cagccgaaaa caucagcaca   2760

gccaggggcg uggccagcau cuccaacagc cgggccgauu uugccaucuc cggccaguug   2820

aaggaccaug ccagccacua cggcgcgggg ggccugguag gcaggaaccg cggcggccuc   2880

auccgcagca gcggcaguca gggaacgcug ucgcugagcg gucacggaau gaaccuggga   2940

ggacuggucg gauacaguuc cgccggcgga cuggcggacg uuuccgccuc cgucgacguc   3000

ucaggcaacg gacagcgcgg ccuguacggu gggcucaucg gccucaacgu aaacaguggu   3060

auugcccacg ccacggccag cggcaagguc cggggcacag acgcggaagc acugggcggg   3120

cugaucggcc ggaaccugaa cgcggccauc aacaacgcca gcgcccaugg cgaugucagc   3180

cugcaagccg gucgcuaccu gggaggccug aucggccaca accaggcagg caaccuggcc   3240

aacgucagua ccagcggcaa ccugaguggu gggucgcugc uccaggccgg cggccugauc   3300

ggucucaacg ccaaugccuc gcuggucaau gccuccgcca agggcaaugu cgcuacccgc   3360

ggagcagaag cgguuggcgg ucugcucgga gaaaaccugu acggcuccgu caucaacggu   3420

uccgccagug gcgaagucac cgacggcagc ggcaaaaccc ugggugguccu gauagggucc   3480

aaccucggcg gcaaucauuc caaccugaag gccuccgggu ggguaaacgc aggggcgaac   3540

agugacgugg gagggcugau cggccacaac cggggcggca accacagcac ccuggcggca   3600

uccggcaaug ucaccggggg caagggcagu cgcgucggcg gacucgucgg cuauaacgau   3660

gccgccucgc ugacgaacgu cucggcuucg ggcaacguca gcgccagugg uuccagggcc   3720

aucggcgggu ugaucggcag ugaccugcga gguucgcuga ugcucgccag cagucaugga   3780

aucgugaacg acaagaccag ccacaaccug ggagggguugg ucggccgcgg ugaaaacacc   3840

ucgauccgcu ccgccaaggc cagcggugcg gugagcggag gcgccgggau cagggccggc   3900

ggacuggucg gcucccugga gggcuggcag gcucucaucc ugggggccuc ggccggcggc   3960

gaugugacgg cgggcuacga uagcuauauu ggcgggcugg ugggcuucag caccgccacc   4020

aucagcggcg cuuccgcuuc cggcaagguc ggaggcucgg gucugcuggg cggccugguc   4080

gccuggaacc aggggaaugu cauggguucu ucggccagcg gcaggcugga gccacaaauc   4140

cccaaccaga uccauggcgg acugaucggc aucaauuuug gcuggcaguc cuggaacucg   4200

guauacgggg cugcggcgac cguuccaaug auaggucgcc acuacaaccu guga         4254
```

```
<210> SEQ ID NO 43
<211> LENGTH: 12
<212> TYPE: PRT
<213> ORGANISM: Artificial sequence
<220> FEATURE:
<223> OTHER INFORMATION: Rigid linker sequence

<400> SEQUENCE: 43

Ala Glu Ala Ala Ala Lys Glu Ala Ala Ala Lys Ala
1               5                   10


<210> SEQ ID NO 44
<211> LENGTH: 135
<212> TYPE: PRT
<213> ORGANISM: Pseudomonas aeruginosa

<400> SEQUENCE: 44

Met Pro Arg Gly Asp Lys Ser Lys Tyr Ser Asp Lys Gln Gln Arg Lys
1               5                   10                  15

Ala Glu His Ile Glu Glu Ser Tyr Lys Ala Lys Gly Val Ser Glu Ser
```

```
            20                  25                  30

Glu Ala Glu Ala Arg Ala Trp Ala Thr Val Asn Lys Gln Ser Gly Gly
        35                  40                  45

Gly Glu Arg Lys Gly Gly Ser Gly Arg Ala Lys Ser Glu Thr Ala Lys
    50                  55                  60

Arg Ala Asp Arg Lys Asp Ser Ala His Arg Ala Ala Gln Ala Arg Ser
65                  70                  75                  80

Gly Arg Pro Ala Asn Arg Gly Ser Ala Ser Arg Gly Lys Arg Gln Gly
                85                  90                  95

Ser Thr Ser Val Ser Glu Met Thr Arg Glu Glu Leu Met Gln Leu Ala
            100                 105                 110

Arg Lys Arg Asp Ile Arg Gly Arg Ser Thr Met Arg Lys Ala Glu Leu
        115                 120                 125

Ile Glu Ala Leu Ser Arg Ala
    130                 135


<210> SEQ ID NO 45
<211> LENGTH: 140
<212> TYPE: PRT
<213> ORGANISM: Pseudomonas aeruginosa

<400> SEQUENCE: 45

Ala Thr Arg Arg Lys Thr Thr Pro Gln Glu Ile Asp Asp Ile Gln Asp
1               5                   10                  15

Arg Met Gly Ser Met Arg Glu Leu Asp Phe Asp Glu Arg Arg Gln Ala
            20                  25                  30

Arg Lys Ala Arg Ile Gly Asp Glu Arg Pro Glu Ala Glu Val Glu Ala
        35                  40                  45

Glu Phe Ser Ser Arg Arg Val Arg Glu Ala Gly His Ala Gly Gly Gln
    50                  55                  60

Pro Asp Glu Asp Asp Gly Tyr Gln Asp Asn Val Gly Met Asp Asp Leu
65                  70                  75                  80

Ala Pro Glu Thr Leu Ile Asp Glu Ser Gly Ala Arg Ser Pro Ala Glu
                85                  90                  95

Arg Gly Gly Glu Ser Pro Ala Asp Lys Arg Leu Arg Val Val His Gly
            100                 105                 110

Asn Glu Ile Gly Ala Gly His Gly Leu Asp Glu Ala Glu Leu Ala Arg
        115                 120                 125

Arg Asp Pro Leu Asp Gly Ser Ser Asp Glu Glu Arg
    130                 135                 140


<210> SEQ ID NO 46
<211> LENGTH: 96
<212> TYPE: PRT
<213> ORGANISM: Pseudomonas aeruginosa

<400> SEQUENCE: 46

Ser Phe Lys Gln Tyr Asn Gln Asn Thr Ile Glu Ile Val Gly Tyr Thr
1               5                   10                  15

Asp Ser Thr Gly Ser Arg Gln His Asn Met Asp Leu Ser Gln Arg Arg
            20                  25                  30

Ala Gln Ser Val Ala Gly Tyr Leu Thr Ala Gln Gly Val Asp Gly Thr
        35                  40                  45

Arg Leu Ser Thr Arg Gly Met Gly Pro Asp Gln Pro Ile Ala Ser Asn
    50                  55                  60

Ser Thr Ala Asp Gly Arg Ala Gln Asn Arg Arg Val Glu Val Asn Leu
```

```
65                  70                  75                  80

Arg Pro Val Pro Gly Ala Gln Gly Pro Ala Gln Thr Gln Pro Gln Tyr
                85                  90                  95


<210> SEQ ID NO 47
<211> LENGTH: 377
<212> TYPE: PRT
<213> ORGANISM: Pseudomonas aeruginosa

<400> SEQUENCE: 47

Cys Gly Trp Leu Trp Gly Pro Glu Gly Tyr Phe Arg Asp Arg Gly Asp
1               5                   10                  15

Asp Tyr Leu Gly Ala Arg Glu Thr Pro Pro Met Gln Leu Pro Glu Gly
            20                  25                  30

Val His Ser Lys Pro Leu Asp Pro Leu Leu Pro Ile Pro Leu Asn Val
        35                  40                  45

Ala Thr Thr His Glu Lys Glu Gly Glu Tyr Glu Val Pro Arg Pro Gln
    50                  55                  60

Pro Leu Ala Asn Ala Gly Asp Ile Ser Asp Tyr Ser Leu Gln Arg Ser
65                  70                  75                  80

Gly Asp Ser Arg Trp Val Val Ala Gln Arg Pro Pro Ala Glu Val Trp
                85                  90                  95

Pro Val Ala Arg Gln Phe Phe Glu Glu Asn Gly Phe Arg Ile Ala Asp
            100                 105                 110

Glu Arg Pro Gln Thr Gly Glu Phe Ser Ser Asp Trp Gln Ser Leu Ser
        115                 120                 125

Gln Leu Ser Ala Pro Leu Ala Arg Arg Leu Ser Ser Arg Val Ser Gly
    130                 135                 140

Val Glu Pro Asp Gly Gln Ala Arg Val Arg Val Arg Ile Glu Pro Gly
145                 150                 155                 160

Val Gln Ser Asn Thr Ser Glu Val Tyr Val Leu Ser Gln Thr Arg Ala
                165                 170                 175

Ala Gly Asp Thr Ser Ser Pro Ser Trp Pro Ser Lys Ser Val Ala Pro
            180                 185                 190

Ser Leu Asp Ala Ala Leu Leu Asp Glu Met Val Ala Ser Met Ala Arg
        195                 200                 205

Ser Ala Glu Gln Gly Gly Ser Val Ser Leu Leu Ala Ala Asn Ser Ile
    210                 215                 220

Tyr Asp Thr Pro Gly Thr Phe Glu Leu Ser Lys Asp Gly Ser Gly Asn
225                 230                 235                 240

Pro Val Leu Thr Leu Gln Ser Asp Phe Asp Arg Ser Trp Val Ser Val
                245                 250                 255

Gly Arg Ala Leu Asp Asn Ala Asp Ile Arg Val Asp Asp Leu Asn Arg
            260                 265                 270

Ser Leu Gly Val Tyr Tyr Val Asn Ile Ala Glu Gly Ala Lys Lys Pro
        275                 280                 285

Asp Glu Asp Lys Pro Gly Phe Phe Ser Arg Leu Phe Gly Gly Gly Glu
    290                 295                 300

Lys Thr Lys Glu Glu Glu Asp Ala Lys Ala Gln Arg Tyr Gln Val Arg
305                 310                 315                 320

Leu Thr Thr Val Ser Asp Ala Val Gln Val Thr Val Asp Lys Asp Ile
                325                 330                 335

Asn Thr Ser Ala Pro Ala Asp Val Ala Gln Asn Val Leu Glu Lys Leu
            340                 345                 350
```

```
Gln Glu Ser Met Arg Asn Ala Val Arg Gly Ser Gly Gln Arg Lys Pro
        355                 360                 365

Gly Gln Phe Gly Leu Gly Glu Gln Phe
    370                 375


<210> SEQ ID NO 48
<211> LENGTH: 639
<212> TYPE: PRT
<213> ORGANISM: Pseudomonas aeruginosa

<400> SEQUENCE: 48

Met Ser Phe Ser Ser Leu Gly Leu Ser Glu Ala Leu Ala Arg Ala Val
1               5                   10                  15

Glu Ala Ala Gly Tyr Ser Gln Pro Thr Pro Val Gln Gln Arg Ala Ile
            20                  25                  30

Pro Ala Val Leu Gln Gly Arg Asp Leu Met Val Ala Ala Gln Thr Gly
        35                  40                  45

Thr Gly Lys Thr Gly Gly Phe Ala Leu Pro Val Leu Glu Arg Leu Phe
    50                  55                  60

Pro Ala Gly His Pro Asp Arg Glu His Arg His Gly Pro Arg Gln Ala
65                  70                  75                  80

Arg Val Leu Val Leu Thr Pro Thr Arg Glu Leu Ala Ala Gln Val His
                85                  90                  95

Asp Ser Phe Lys Val Tyr Ala Arg Asp Leu Pro Leu Asn Ser Thr Cys
            100                 105                 110

Ile Phe Gly Gly Val Gly Met Asn Pro Gln Ile Gln Ala Leu Ala Lys
        115                 120                 125

Gly Val Asp Val Leu Val Ala Cys Pro Gly Arg Leu Leu Asp Leu Ala
    130                 135                 140

Gly Gln Asn Lys Val Asp Leu Ser His Val Glu Ile Leu Val Leu Asp
145                 150                 155                 160

Glu Ala Asp Arg Met Leu Asp Met Gly Phe Ile His Asp Val Lys Lys
                165                 170                 175

Val Leu Ala Lys Leu Pro Pro Lys Arg Gln Asn Leu Leu Phe Ser Ala
            180                 185                 190

Thr Phe Ser Lys Asp Ile Val Asp Leu Ala Asn Lys Leu Leu His Asn
        195                 200                 205

Pro Glu Arg Ile Glu Val Thr Pro Pro Asn Thr Thr Val Glu Arg Ile
    210                 215                 220

Glu Gln Arg Val Phe Arg Leu Pro Ala Pro Gln Lys Arg Ala Leu Leu
225                 230                 235                 240

Ala His Leu Val Thr Val Gly Ala Trp Glu Gln Val Leu Val Phe Thr
                245                 250                 255

Arg Thr Lys His Gly Ala Asn Arg Leu Ala Glu Tyr Leu Thr Lys His
            260                 265                 270

Gly Leu Pro Ala Ala Ala Ile His Gly Asn Lys Ser Gln Asn Ala Arg
        275                 280                 285

Thr Lys Ala Leu Ala Asp Phe Lys Ala Asn Asp Val Arg Ile Leu Val
    290                 295                 300

Ala Thr Asp Ile Ala Ala Arg Gly Leu Asp Ile Asp Gln Leu Pro His
305                 310                 315                 320

Val Val Asn Tyr Glu Leu Pro Asn Val Glu Glu Asp Tyr Val His Arg
                325                 330                 335

Ile Gly Arg Thr Gly Arg Ala Gly Arg Ser Gly Glu Ala Ile Ser Leu
            340                 345                 350
```

```
Val Ala Pro Asp Glu Glu Lys Leu Leu Lys Ala Ile Glu Lys Met Thr
        355                 360                 365

Arg Gln Arg Ile Pro Asp Gly Asp Ala Gln Gly Phe Asp Pro Glu Ala
    370                 375                 380

Val Leu Pro Glu Val Ala Gln Pro Glu Pro Arg Glu Ala Pro Gln Lys
385                 390                 395                 400

Gln Pro Arg Arg Asp Lys Glu Arg Arg Ser Ser Arg Glu Arg Lys Pro
                405                 410                 415

Lys Asp Ala Gln Ala Ser Asn Pro Asp Ser Asn Val Ala Ala Ala Gln
            420                 425                 430

Asp Gly Thr Glu Lys Pro Ala Gly Lys Arg Arg Arg Arg Gly Gly Lys
        435                 440                 445

Asn Lys Glu Asn Arg Glu Ala Gly Gln Ala Gln Gln Pro Arg Gln Ser
    450                 455                 460

Arg Glu Ala Arg Pro Ala Lys Pro Asn Arg Pro Pro Glu Val Asp Gly
465                 470                 475                 480

Asn Arg Asp Pro Glu Glu Phe Leu Asp Asp Asp Phe Asp Asn Phe Gly
                485                 490                 495

Asn Arg Ala Asp Tyr Val Ser Pro Tyr Gln Gly Gln Glu Asn Lys Gly
            500                 505                 510

Arg Gly Arg Arg Gly Gly Gln Gln Lys Pro Gln Gly Gly Thr Gly Gln
        515                 520                 525

Gln Gly Arg Gly Gln Gly Gln Gly Gln Ala Arg Gly Lys Ser Gln Gly
    530                 535                 540

Ala Ala Gln Gly Gly Ala Arg Gly Gln Gly Ala Gly Gln Gly Lys Ala
545                 550                 555                 560

Lys Lys Pro Arg Ala Gly Lys Pro Arg Gly Gln Gly Arg Glu Asn Ala
                565                 570                 575

Ser Arg Met Ser Asp Ala Pro Leu Arg Glu Pro Ser Glu Tyr Gly Thr
            580                 585                 590

Gly Lys Gln Pro Ser Arg Gln Pro Val Val Ile Asn Lys Arg Asp Leu
        595                 600                 605

Val Arg Met Asp Arg Phe Pro Thr Ala Glu Gln Leu Asp Glu Leu Glu
    610                 615                 620

Pro Arg Arg Lys Gly Glu Arg Pro Ala Leu Leu Thr Arg Asn Arg
625                 630                 635
```

<210> SEQ ID NO 49
<211> LENGTH: 652
<212> TYPE: PRT
<213> ORGANISM: Pseudomonas aeruginosa

<400> SEQUENCE: 49

```
Ser Glu Pro Thr Thr Asp Ala Ala Leu Ile Glu Lys Gly Arg Tyr Val
1               5                   10                  15

Ala Gln Leu Gly Asp Cys Ile Ala Cys His Thr Gly Pro Gln Gly Ala
            20                  25                  30

Pro Met Ala Gly Gly Leu Glu Leu Lys Thr Pro Met Gly Thr Ile Tyr
        35                  40                  45

Ser Thr Asn Ile Thr Pro Asp Arg Glu Thr Gly Ile Gly Arg Tyr Ser
    50                  55                  60

Phe Glu Glu Phe Asp Arg Ala Met Arg Lys Gly Val Thr Ala Glu Gly
65                  70                  75                  80

Val Asn Leu Tyr Pro Ala Met Pro Tyr Pro Ser Tyr Ala Lys Ile Ser
```

```
                85                  90                  95

Glu Glu Asp Met Arg Ala Leu Tyr Ala Tyr Leu Met His Gly Val Gln
            100                 105                 110

Pro Val Thr Gln Ala Asn Thr Pro Ser Ala Met Ser Trp Pro Phe Asn
        115                 120                 125

Gln Arg Trp Gly Leu Ser Leu Trp Asn Trp Ala Phe Leu Asp Asp Ala
    130                 135                 140

Pro Phe Thr Pro Ser Ser Asp Ala Asp Pro Val Ile Asn Arg Gly Ala
145                 150                 155                 160

Tyr Leu Val Gln Gly Leu Gly His Cys Gly Ala Cys His Thr Pro Arg
                165                 170                 175

Gly Ile Ala Phe Gln Glu Lys Ala Met Ser Glu Ala Gly Arg Ser Gly
            180                 185                 190

Gln Phe Tyr Leu Ala Gly Glu Thr Val Glu Gln Trp Gln Ala Leu Ser
        195                 200                 205

Leu Arg Asn Leu Trp Thr Val Glu Asp Thr Val Gln Leu Leu Lys Thr
    210                 215                 220

Gly Gln Asn Arg Phe Ala Thr Val Ser Gly Ser Met Thr Asp Val Ile
225                 230                 235                 240

His His Ser Thr Gln His Phe Ser Asp Asp Asp Leu Leu Ala Ile Ala
                245                 250                 255

Ser Tyr Leu Lys Ser Leu Pro Ala Gly Lys Asp Asp Leu Pro Met Pro
            260                 265                 270

Asp Ser Glu Arg Pro Leu Ala Ala Pro Val Asp Leu Tyr Ser Ser Arg
        275                 280                 285

Gly Gly Leu Gly Tyr Ala Gln Phe Cys Ser Asp Cys His Arg Lys Asp
    290                 295                 300

Gly Ser Gly Val Pro Gly Met Phe Pro Pro Leu Ala Gly Asn Pro Thr
305                 310                 315                 320

Val Ala Ser Ala Asn Pro Ser Thr Leu Leu His Ile Thr Leu Thr Gly
                325                 330                 335

Trp Lys Thr Ala Gln Thr Ala Thr His Ser Arg Val Tyr Thr Met Pro
            340                 345                 350

Gly Phe Ala Gln Leu Glu Asp Arg Glu Ile Ala Glu Ile Leu Ser Phe
        355                 360                 365

Val Arg Ser Ser Trp Gly Asn Gln Gly Ser Ser Ile Asp Ala Gly Gln
    370                 375                 380

Val Lys Lys Leu Arg Gln Arg Ile Glu Ala Gly Asn Gly Pro Ala Thr
385                 390                 395                 400

Thr Phe Val Ser Pro Arg Leu Ala Asp Met Leu Ala Ala Pro Asn Ala
                405                 410                 415

Glu Gln Val Val Arg Gly Met Arg Leu His Leu Glu Thr Arg Glu Leu
            420                 425                 430

Leu Pro Ala Asn Val Gly Asn Gln Leu His Cys Thr Ser Cys His Leu
        435                 440                 445

Asn Ala Gly Thr Val Ala Asp Gly Ser Pro Phe Val Gly Val Ser Ala
    450                 455                 460

Phe Phe Pro Ser Tyr Ala Pro Arg Ala Gly Lys Val Ile Gly Leu Glu
465                 470                 475                 480

Glu Arg Ile Asn Gly Cys Phe Arg Arg Ser Met Asn Gly Lys Pro Leu
                485                 490                 495

Pro Pro Asp Ser Ala Asp Met Gln Ala Met Val Ala Tyr Phe Asp Trp
            500                 505                 510
```

Met Lys Asn Asn Thr Arg Pro Gln Asp Lys Val Ala Gly Arg Gly Val
515 520 525

Gly Lys Val Asp Pro Ala Leu Lys Pro Asp Pro Glu Asn Gly Arg Lys
530 535 540

Val Tyr Ala Arg Gln Cys Val Val Cys His Gly Glu Asn Gly Glu Gly
545 550 555 560

Leu Arg Asn Ser Ala Gly Glu Met Leu Phe Pro Pro Leu Trp Gly Asp
565 570 575

Glu Ser Phe Asn Ile Gly Ala Gly Met Ala Arg Thr Phe Thr Ala Ala
580 585 590

Ala Phe Val Lys His Asn Met Pro Ile Gly Phe Gln Glu Arg Phe Pro
595 600 605

Leu Gly Gln Gly Gly Leu Ser Asp Gln Asp Ala Val Asp Val Ala Glu
610 615 620

Tyr Phe Ser His Gln Pro Arg Pro Asp Phe Pro Asp Lys Ile Lys Asp
625 630 635 640

Trp Pro Lys Asp Lys Arg Pro Leu Asp Ala Arg Tyr
645 650

<210> SEQ ID NO 50
<211> LENGTH: 456
<212> TYPE: PRT
<213> ORGANISM: Artificial sequence
<220> FEATURE:
<223> OTHER INFORMATION: Fusion protein

<400> SEQUENCE: 50

Gly Ser Ser Ile Asp Ala Gly Gln Val Lys Lys Leu Arg Gln Arg Ile
1 5 10 15

Glu Ala Gly Asn Gly Pro Ala Thr Thr Phe Val Ser Pro Arg Leu Ala
20 25 30

Asp Met Leu Ala Ala Pro Asn Ala Glu Gln Val Val Arg Gly Met Arg
35 40 45

Leu His Leu Glu Thr Arg Glu Leu Leu Pro Ala Asn Val Gly Asn Gln
50 55 60

Leu His Cys Thr Ser Cys His Leu Asn Ala Gly Thr Val Ala Asp Gly
65 70 75 80

Ser Pro Phe Val Gly Val Ser Ala Phe Phe Pro Ser Tyr Ala Pro Arg
85 90 95

Ala Gly Lys Val Ile Gly Leu Glu Glu Arg Ile Asn Gly Cys Phe Arg
100 105 110

Arg Ser Met Asn Gly Lys Pro Leu Pro Pro Asp Ser Ala Asp Met Gln
115 120 125

Ala Met Val Ala Tyr Phe Asp Trp Met Lys Asn Asn Thr Arg Pro Gln
130 135 140

Asp Lys Val Ala Gly Arg Gly Val Gly Lys Val Asp Pro Ala Leu Lys
145 150 155 160

Pro Asp Pro Glu Asn Gly Arg Lys Val Tyr Ala Arg Gln Cys Val Val
165 170 175

Cys His Gly Glu Asn Gly Glu Gly Leu Arg Asn Ser Ala Gly Glu Met
180 185 190

Leu Phe Pro Pro Leu Trp Gly Asp Glu Ser Phe Asn Ile Gly Ala Gly
195 200 205

Met Ala Arg Thr Phe Thr Ala Ala Ala Phe Val Lys His Asn Met Pro
210 215 220

```
Ile Gly Phe Gln Glu Arg Phe Pro Leu Gly Gln Gly Gly Leu Ser Asp
225                 230                 235                 240

Gln Asp Ala Val Asp Val Ala Glu Tyr Phe Ser His Gln Pro Arg Pro
                245                 250                 255

Asp Phe Pro Asp Lys Ile Lys Asp Trp Pro Lys Asp Lys Arg Pro Leu
            260                 265                 270

Asp Ala Arg Tyr Ala Glu Ala Ala Ala Lys Glu Ala Ala Ala Lys Ala
        275                 280                 285

Ser Glu Pro Thr Thr Asp Ala Ala Leu Ile Glu Lys Gly Arg Tyr Val
    290                 295                 300

Ala Gln Leu Gly Asp Cys Ile Ala Cys His Thr Gly Pro Gln Gly Ala
305                 310                 315                 320

Pro Met Ala Gly Gly Leu Glu Leu Lys Thr Pro Met Gly Thr Ile Tyr
                325                 330                 335

Ser Thr Asn Ile Thr Pro Asp Arg Glu Thr Gly Ile Gly Arg Tyr Ser
            340                 345                 350

Phe Glu Glu Phe Asp Arg Ala Met Arg Lys Gly Val Thr Ala Glu Gly
        355                 360                 365

Val Asn Leu Tyr Pro Ala Met Pro Tyr Pro Ser Tyr Ala Lys Ile Ser
    370                 375                 380

Glu Glu Asp Met Arg Ala Leu Tyr Ala Tyr Leu Met His Gly Val Gln
385                 390                 395                 400

Pro Val Thr Gln Ala Asn Thr Pro Ser Ala Met Ser Trp Pro Phe Asn
                405                 410                 415

Gln Arg Trp Gly Leu Ser Leu Trp Asn Trp Ala Phe Leu Asp Asp Ala
            420                 425                 430

Pro Phe Thr Pro Ser Ser Asp Ala Asp Pro Val Ile Asn Arg Gly Ala
        435                 440                 445

Tyr Leu Val Gln Gly Leu Gly His
    450                 455


<210> SEQ ID NO 51
<211> LENGTH: 311
<212> TYPE: PRT
<213> ORGANISM: Pseudomonas aeruginosa

<400> SEQUENCE: 51

Arg Arg Arg Arg Glu Glu Ala Pro Val Pro Ala Val Glu Pro Lys Arg
1               5                   10                  15

Arg Val Ala Leu Asn Leu Pro Leu Arg Arg Ala Pro Arg Pro Pro Ala
            20                  25                  30

Ala Ala Pro Ala Pro Ala Lys Val Glu Glu Gln Ala Arg Pro Pro Val
        35                  40                  45

Ala Ala Pro Ser Ser Pro Pro Pro Ser Pro Pro Pro Ala Pro Ala Ala
    50                  55                  60

Ala Pro Arg Ala Ala Met Ala Ala Ala Asp Lys Leu Asp Gly Ala Asp
65                  70                  75                  80

Ile Tyr Ile Ala Tyr Gly Arg Tyr Gly Gln Ala Arg Asp Leu Leu Arg
                85                  90                  95

Gln Val Leu Ala Glu Gln Pro Gln Arg Leu Ser Ala Arg Met Lys Leu
            100                 105                 110

Leu Leu Val Leu Ala Glu Leu Gly Asp Ala Ala Gly Phe Asp Ala Leu
        115                 120                 125

Ala Glu Glu Thr Leu Ala Ser Gly Gly Asn Pro Glu Ala Ile Asp Glu
```

```
    130                 135                 140

Leu Arg Gly Arg Tyr Pro Ala Leu Leu Gln Met Pro Ala Thr Glu Thr
145                 150                 155                 160

Pro Ala Ala Thr Thr Lys Asp Asp Asp Trp Ser Asp Leu Pro Leu Ala
                165                 170                 175

Glu Ser Pro Val Leu Gln Gln Pro Asp Ala Thr Ser Gly Ala Asp Gly
            180                 185                 190

Phe Gly Asp Leu Asn Leu Asp Leu Asp Leu Asp Trp Gly Ala Leu Glu
        195                 200                 205

Asn Pro Leu Asp Asn Pro Asp Leu Pro Arg Arg Ala Ala Ala Gly Lys
    210                 215                 220

Ala Glu Pro Ala Glu Glu Pro Leu Ala Phe Glu Ser Asn Leu His Glu
225                 230                 235                 240

Leu Pro Asp Val Ala Glu Tyr Glu His Leu Glu Leu Asp Gln Pro Glu
                245                 250                 255

Pro Ala Thr Val Pro Pro Glu Glu Ala Ser Ala Ser Leu Asp Arg Ala
            260                 265                 270

Arg Ala Cys Ile Asp Ser Gly Asp Leu Asp Gln Ala Ser Arg Ile Leu
        275                 280                 285

Arg Leu Val Val Ala His Gly Asp Pro Trp Gln Lys Ala Glu Ala Arg
    290                 295                 300

Glu Leu Leu Ala Leu Ile Ala
305                 310


<210> SEQ ID NO 52
<211> LENGTH: 328
<212> TYPE: PRT
<213> ORGANISM: Pseudomonas aeruginosa

<400> SEQUENCE: 52

Leu Gly Val Gly Asp Ile Ile Leu His Ser Ala Leu Asn Gln Pro Leu
1               5                   10                  15

Asp Ala Asp Ile Glu Leu Leu Asp Val Gly Asp Leu Gly Ala Asp Glu
            20                  25                  30

Ile Glu Val Arg Leu Ala Gly Ala Asp Val Phe Ala Ala Ala Gly Val
        35                  40                  45

Glu Arg Leu Gln Phe Leu Asn Glu Leu Arg Phe Ser Pro Val Leu Gln
    50                  55                  60

Gly Arg Gly Gly Asn Arg Ile His Val Ser Ser Ile Arg Pro Val Gln
65                  70                  75                  80

Glu Pro Tyr Leu Asn Phe Leu Val Glu Val Ala Arg Pro Asn Gly Arg
                85                  90                  95

Ile Val Arg Glu Phe Thr Val Leu Leu Asp Pro Leu Gly Tyr Thr Pro
            100                 105                 110

Arg Met Leu Pro Ala Ala Arg Ser Gly Ile Glu Pro Gln Arg Gln Ser
        115                 120                 125

Ser Thr Pro Val Pro Ala Pro Arg Ser Ala Ala Val Val Val Asp Pro
    130                 135                 140

Ala Leu Leu Glu Pro Gly Asp Glu Tyr Leu Ala Arg Pro Ser Asp Asn
145                 150                 155                 160

Leu Trp Ala Ile Ser Gly Arg Leu Arg Gly Ala Gly Asn Ala Asp Arg
                165                 170                 175

Ala Gln Leu Met Glu Ala Leu Tyr Gln Leu Asn Pro Gln Ala Phe Val
            180                 185                 190
```

```
Asn Ala Asp Arg His Arg Leu Lys Ala Gly Ala Arg Leu Arg Leu Pro
        195                 200                 205

Ala Gly Tyr Gln Pro Glu Arg Gly Ala Pro Gly Ala Val Lys Glu Ala
    210                 215                 220

Ala Val Glu Val Leu Pro Pro Ala Asp Ala Ala Val Val Glu Asn Ala
225                 230                 235                 240

Pro Ala Ala Leu Val Glu Ala Gln Arg Gln Ala Asp Ala Glu Ala Glu
                245                 250                 255

Ala Leu Ala Arg Gln Arg Glu Glu Leu Ser Gln Arg Met Asp Asp Leu
            260                 265                 270

Gln Arg Gln Leu Gln Ala Leu Gln Glu Gln Leu Gln Gln Arg Asp His
        275                 280                 285

Gln Val Ala Glu Leu Gln Gln Gln Leu Ala Arg Arg Gln Ala Val Arg
    290                 295                 300

Pro Ala Ala Pro Pro Pro Ala Ala Ala Ala Pro Ser Val Ala Gln Pro
305                 310                 315                 320

Val Glu Thr Pro Thr Asp Ser Gln
                325


<210> SEQ ID NO 53
<211> LENGTH: 379
<212> TYPE: PRT
<213> ORGANISM: Artificial sequence
<220> FEATURE:
<223> OTHER INFORMATION: Fusion protein

<400> SEQUENCE: 53

Ala Asp Gly Arg Pro Ser Glu Leu Pro Ser Gln Val Ile Thr Ala Asn
1               5                   10                  15

Pro Leu Gly Asn Glu Ser Pro Ala Thr Pro Ser Ser Val Leu Glu Gly
            20                  25                  30

Asp Glu Leu Thr Leu Arg Gln Lys Gly Ser Leu Gly Glu Thr Leu Asn
        35                  40                  45

Gly Leu Pro Gly Val Ser Ser Thr Tyr Phe Gly Pro Gly Ala Ser Arg
    50                  55                  60

Pro Val Ile Arg Gly Met Asp Gly Asp Arg Ile Arg Leu Leu Arg Asn
65                  70                  75                  80

Gly Val Gly Ala Leu Asp Ala Ser Ser Leu Ser Tyr Asp His Ala Val
                85                  90                  95

Pro Glu Asp Pro Asn Ser Val Glu Arg Leu Glu Val Val Arg Gly Pro
            100                 105                 110

Ala Ala Leu Leu Tyr Gly Gly Asn Ala Ile Gly Gly Val Val Asn Ser
        115                 120                 125

Phe Asp Asn Arg Ile Pro Ser Glu Pro Val Asp Gly Ile His Gly Ser
    130                 135                 140

Gly Glu Leu Arg Tyr Gly Gly Ala Asp Thr Thr Arg Ser Arg Ser Gly
145                 150                 155                 160

Ala Leu Glu Ala Gly Asp Gly Asn Phe Ala Leu His Val Asp Ala Ala
                165                 170                 175

Ser Arg Glu Phe Asn Asp Val Arg Ile Pro Gly Tyr Ala His Ser Ser
            180                 185                 190

Arg Gln Ala Glu Ala Ala Ala Lys Glu Ala Ala Ala Lys Ala Ser Gly
        195                 200                 205

Arg His Arg Asn Glu Glu Gly Glu Val Val Ala Ala Gly Asp Asp Glu
    210                 215                 220
```

```
Ala Leu Pro Glu Tyr Leu Tyr Ser Gly Val Arg Ala Asp Phe Tyr Gly
225                 230                 235                 240

Val Glu Ala Gln Asp Arg Ile His Leu Leu Glu Ser Pro Tyr Gly Asn
                245                 250                 255

Phe Asp Leu Glu Leu Ser Gly Asp Tyr Thr Arg Ala Lys Asn Lys Asp
            260                 265                 270

Thr Gly Glu Pro Leu Pro Arg Ile Ala Pro Leu Arg Leu Asn Thr Ala
        275                 280                 285

Leu Ile Trp Glu Leu Gln Gln Trp Gln Ala Arg Val Asp Val Glu His
    290                 295                 300

Ala Ala Ser Gln His Arg Val Pro Glu Glu Glu Leu Ser Thr Asp Gly
305                 310                 315                 320

Tyr Thr Thr Leu Gly Ala Ser Leu Gly Tyr Asn Phe Asp Leu Gly Glu
                325                 330                 335

Ser Arg Trp Leu Ala Phe Val Lys Gly Thr Asn Leu Thr Asn Gln Thr
            340                 345                 350

Val Arg Tyr Ala Ser Ser Ile Leu Arg Asp Arg Val Pro Ala Ala Gly
        355                 360                 365

Arg Gly Ile Glu Ala Gly Val Lys Val Ala Phe
    370                 375


<210> SEQ ID NO 54
<211> LENGTH: 649
<212> TYPE: PRT
<213> ORGANISM: Artificial sequence
<220> FEATURE:
<223> OTHER INFORMATION: Fusion protein

<400> SEQUENCE: 54

Ser Gly Arg His Arg Asn Glu Glu Gly Glu Val Val Ala Ala Gly Asp
1               5                   10                  15

Asp Glu Ala Leu Pro Glu Tyr Leu Tyr Ser Gly Val Arg Ala Asp Phe
            20                  25                  30

Tyr Gly Val Glu Ala Gln Asp Arg Ile His Leu Leu Glu Ser Pro Tyr
        35                  40                  45

Gly Asn Phe Asp Leu Glu Leu Ser Gly Asp Tyr Thr Arg Ala Lys Asn
    50                  55                  60

Lys Asp Thr Gly Glu Pro Leu Pro Arg Ile Ala Pro Leu Arg Leu Asn
65                  70                  75                  80

Thr Ala Leu Ile Trp Glu Leu Gln Gln Trp Gln Ala Arg Val Asp Val
                85                  90                  95

Glu His Ala Ala Ser Gln His Arg Val Pro Glu Glu Glu Leu Ser Thr
            100                 105                 110

Asp Gly Tyr Thr Thr Leu Gly Ala Ser Leu Gly Tyr Asn Phe Asp Leu
        115                 120                 125

Gly Glu Ser Arg Trp Leu Ala Phe Val Lys Gly Thr Asn Leu Thr Asn
    130                 135                 140

Gln Thr Val Arg Tyr Ala Ser Ser Ile Leu Arg Asp Arg Val Pro Ala
145                 150                 155                 160

Ala Gly Arg Gly Ile Glu Ala Gly Val Lys Val Ala Phe Ala Glu Ala
                165                 170                 175

Ala Ala Lys Glu Ala Ala Ala Lys Ala Ala Asp Gly Arg Pro Ser Glu
            180                 185                 190

Leu Pro Ser Gln Val Ile Thr Ala Asn Pro Leu Gly Asn Glu Ser Pro
        195                 200                 205
```

```
Ala Thr Pro Ser Ser Val Leu Glu Gly Asp Glu Leu Thr Leu Arg Gln
    210                 215                 220

Lys Gly Ser Leu Gly Glu Thr Leu Asn Gly Leu Pro Gly Val Ser Ser
225                 230                 235                 240

Thr Tyr Phe Gly Pro Gly Ala Ser Arg Pro Val Ile Arg Gly Met Asp
                245                 250                 255

Gly Asp Arg Ile Arg Leu Leu Arg Asn Gly Val Gly Ala Leu Asp Ala
            260                 265                 270

Ser Ser Leu Ser Tyr Asp His Ala Val Pro Glu Asp Pro Asn Ser Val
        275                 280                 285

Glu Arg Leu Glu Val Val Arg Gly Pro Ala Ala Leu Leu Tyr Gly Gly
    290                 295                 300

Asn Ala Ile Gly Gly Val Val Asn Ser Phe Asp Asn Arg Ile Pro Ser
305                 310                 315                 320

Glu Pro Val Asp Gly Ile His Gly Ser Gly Glu Leu Arg Tyr Gly Gly
                325                 330                 335

Ala Asp Thr Thr Arg Ser Arg Ser Gly Ala Leu Glu Ala Gly Asp Gly
            340                 345                 350

Asn Phe Ala Leu His Val Asp Ala Ala Ser Arg Glu Phe Asn Asp Val
        355                 360                 365

Arg Ile Pro Gly Tyr Ala His Ser Ser Arg Gln Arg Gln Ile Asp Gly
    370                 375                 380

Asp Thr Gly Lys His Arg Val Gln Asn Ser Asp Gly Arg Gln Asp Gly
385                 390                 395                 400

Gly Ala Val Gly Gly Ser Tyr His Trp Glu His Gly Tyr Ala Gly Leu
                405                 410                 415

Ser Tyr Ser Gly Tyr Asp Ser Asn Tyr Gly Ser Pro Ala Glu Asp Asp
            420                 425                 430

Val Arg Leu Lys Met Gln Gln Asp Arg Tyr Ala Phe Ala Ser Glu Ile
        435                 440                 445

Arg Asp Leu Glu Gly Pro Phe Thr Ser Leu Lys Leu Asp Ala Ala Tyr
    450                 455                 460

Thr Lys Tyr Glu His Lys Glu Ile Glu Asp Gly Glu Thr Gly Thr Thr
465                 470                 475                 480

Phe Lys Asn Glu Gly Tyr Glu Gly Arg Ile Glu Ala Arg His Arg Pro
                485                 490                 495

Leu Gly Pro Leu Asn Gly Val Val Gly Ala Gln Phe Ala Asn Ser Arg
            500                 505                 510

Phe Ser Ala Leu Gly Glu Glu Ala Phe Val Pro His Thr Glu Thr Asp
        515                 520                 525

Ser Ala Ala Leu Phe Ala Leu Glu Glu Trp Lys Leu Ser Asp Arg Leu
    530                 535                 540

Asp Leu Ser Phe Gly Ala Arg Leu Glu His Thr Arg Val Asp Pro Asp
545                 550                 555                 560

Ala Lys Gly Asn Glu Arg Phe Ala Glu Asn Asp Gly Ser Gln Ser Phe
                565                 570                 575

Thr Thr Gly Ser Leu Ser Thr Gly Ala Val Tyr Lys Leu Thr Pro Ile
            580                 585                 590

Trp Ser Leu Ala Ala Thr Leu Ser Tyr Thr Glu Arg Ala Pro Thr Phe
        595                 600                 605

Tyr Glu Leu Tyr Ala Asn Gly Pro His Ala Ala Thr Gly Thr Tyr Glu
    610                 615                 620

Val Gly Asp Ala Asp Ala Asp Lys Glu Lys Ala Val Ser Thr Asp Leu
```

```
625                 630                 635                 640

Ala Leu Arg Phe Asp Asn Gly Val His
                645


<210> SEQ ID NO 55
<211> LENGTH: 656
<212> TYPE: PRT
<213> ORGANISM: Pseudomonas aeruginosa

<400> SEQUENCE: 55

Ala Asp Gly Arg Pro Ser Glu Leu Pro Ser Gln Val Ile Thr Ala Asn
1               5                   10                  15

Pro Leu Gly Asn Glu Ser Pro Ala Thr Pro Ser Ser Val Leu Glu Gly
            20                  25                  30

Asp Glu Leu Thr Leu Arg Gln Lys Gly Ser Leu Gly Glu Thr Leu Asn
        35                  40                  45

Gly Leu Pro Gly Val Ser Ser Thr Tyr Phe Gly Pro Gly Ala Ser Arg
    50                  55                  60

Pro Val Ile Arg Gly Met Asp Gly Asp Arg Ile Arg Leu Leu Arg Asn
65                  70                  75                  80

Gly Val Gly Ala Leu Asp Ala Ser Ser Leu Ser Tyr Asp His Ala Val
                85                  90                  95

Pro Glu Asp Pro Asn Ser Val Glu Arg Leu Glu Val Val Arg Gly Pro
            100                 105                 110

Ala Ala Leu Leu Tyr Gly Gly Asn Ala Ile Gly Gly Val Val Asn Ser
        115                 120                 125

Phe Asp Asn Arg Ile Pro Ser Glu Pro Val Asp Gly Ile His Gly Ser
    130                 135                 140

Gly Glu Leu Arg Tyr Gly Gly Ala Asp Thr Thr Arg Ser Arg Ser Gly
145                 150                 155                 160

Ala Leu Glu Ala Gly Asp Gly Asn Phe Ala Leu His Val Asp Ala Ala
                165                 170                 175

Ser Arg Glu Phe Asn Asp Val Arg Ile Pro Gly Tyr Ala His Ser Ser
            180                 185                 190

Arg Gln Arg Gln Ile Asp Gly Asp Thr Gly Lys His Arg Val Gln Asn
        195                 200                 205

Ser Asp Gly Arg Gln Asp Gly Gly Ala Val Gly Gly Ser Tyr His Trp
    210                 215                 220

Glu His Gly Tyr Ala Gly Leu Ser Tyr Ser Gly Tyr Asp Ser Asn Tyr
225                 230                 235                 240

Gly Ser Pro Ala Glu Asp Asp Val Arg Leu Lys Met Gln Gln Asp Arg
                245                 250                 255

Tyr Ala Phe Ala Ser Glu Ile Arg Asp Leu Glu Gly Pro Phe Thr Ser
            260                 265                 270

Leu Lys Leu Asp Ala Ala Tyr Thr Lys Tyr Glu His Lys Glu Ile Glu
        275                 280                 285

Asp Gly Glu Thr Gly Thr Thr Phe Lys Asn Glu Gly Tyr Glu Gly Arg
    290                 295                 300

Ile Glu Ala Arg His Arg Pro Leu Gly Pro Leu Asn Gly Val Val Gly
305                 310                 315                 320

Ala Gln Phe Ala Asn Ser Arg Phe Ser Ala Leu Gly Glu Glu Ala Phe
                325                 330                 335

Val Pro His Thr Glu Thr Asp Ser Ala Ala Leu Phe Ala Leu Glu Glu
            340                 345                 350
```

```
Trp Lys Leu Ser Asp Arg Leu Asp Leu Ser Phe Gly Ala Arg Leu Glu
        355                 360                 365

His Thr Arg Val Asp Pro Asp Ala Lys Gly Asn Glu Arg Phe Ala Glu
    370                 375                 380

Asn Asp Gly Ser Gln Ser Phe Thr Thr Gly Ser Leu Ser Thr Gly Ala
385                 390                 395                 400

Val Tyr Lys Leu Thr Pro Ile Trp Ser Leu Ala Ala Thr Leu Ser Tyr
                405                 410                 415

Thr Glu Arg Ala Pro Thr Phe Tyr Glu Leu Tyr Ala Asn Gly Pro His
            420                 425                 430

Ala Ala Thr Gly Thr Tyr Glu Val Gly Asp Ala Asp Ala Asp Lys Glu
        435                 440                 445

Lys Ala Val Ser Thr Asp Leu Ala Leu Arg Phe Asp Asn Gly Val His
    450                 455                 460

Lys Gly Ser Val Gly Val Phe Tyr Ser Arg Phe Ser Asn Tyr Ile Gly
465                 470                 475                 480

Leu Leu Ala Ser Gly Arg His Arg Asn Glu Glu Gly Glu Val Val Ala
                485                 490                 495

Ala Gly Asp Asp Glu Ala Leu Pro Glu Tyr Leu Tyr Ser Gly Val Arg
            500                 505                 510

Ala Asp Phe Tyr Gly Val Glu Ala Gln Asp Arg Ile His Leu Leu Glu
        515                 520                 525

Ser Pro Tyr Gly Asn Phe Asp Leu Glu Leu Ser Gly Asp Tyr Thr Arg
    530                 535                 540

Ala Lys Asn Lys Asp Thr Gly Glu Pro Leu Pro Arg Ile Ala Pro Leu
545                 550                 555                 560

Arg Leu Asn Thr Ala Leu Ile Trp Glu Leu Gln Gln Trp Gln Ala Arg
                565                 570                 575

Val Asp Val Glu His Ala Ala Ser Gln His Arg Val Pro Glu Glu Glu
            580                 585                 590

Leu Ser Thr Asp Gly Tyr Thr Thr Leu Gly Ala Ser Leu Gly Tyr Asn
        595                 600                 605

Phe Asp Leu Gly Glu Ser Arg Trp Leu Ala Phe Val Lys Gly Thr Asn
    610                 615                 620

Leu Thr Asn Gln Thr Val Arg Tyr Ala Ser Ser Ile Leu Arg Asp Arg
625                 630                 635                 640

Val Pro Ala Ala Gly Arg Gly Ile Glu Ala Gly Val Lys Val Ala Phe
                645                 650                 655


<210> SEQ ID NO 56
<211> LENGTH: 546
<212> TYPE: PRT
<213> ORGANISM: Artificial sequence
<220> FEATURE:
<223> OTHER INFORMATION: Fusion protein

<400> SEQUENCE: 56

Gly Gly Thr Ser Asn Asn Pro Phe Gln Thr Ile Gln Arg Glu Asp Val
1               5                   10                  15

Gly Leu Lys Leu Asn Ile Arg Pro Gln Ile Ser Glu Gly Gly Thr Val
            20                  25                  30

Lys Leu Asp Val Tyr Gln Glu Val Ser Ser Val Asp Glu Arg Ala Ser
        35                  40                  45

Thr Ala Ala Gly Val Val Thr Asn Lys Arg Ala Ile Asp Thr Ser Ile
    50                  55                  60
```

```
Leu Leu Asp Asp Gly Gln Ile Met Val Leu Gly Gly Leu Leu Gln Asp
65                  70                  75                  80

Asn Val Gln Asp Asn Thr Asp Gly Val Pro Gly Leu Ser Ser Leu Pro
                85                  90                  95

Gly Val Gly Ser Leu Phe Arg Tyr Gln Lys Arg Ser Arg Thr Lys Thr
            100                 105                 110

Asn Leu Met Val Phe Leu Arg Pro Tyr Ile Val Arg Asp Ala Ala Ala
        115                 120                 125

Gly Arg Ser Ile Thr Leu Asn Arg Tyr Asp Phe Ile Arg Arg Ala Gln
    130                 135                 140

Gln Arg Val Gln Pro Arg His Asp Trp Ser Val Gly Asp Met Gln Ala
145                 150                 155                 160

Pro Val Leu Pro Pro Ala Gln Gln Gly Ile Pro Gln Ala Ala Tyr Asp
                165                 170                 175

Leu Arg Pro Ser Pro Arg Pro Leu Arg Ala Val Pro Leu Gly Glu Ala
            180                 185                 190

Ala Pro Leu Ala Glu Ala Ala Ala Lys Glu Ala Ala Ala Lys Ala Met
        195                 200                 205

Arg Gln Ser Ala Phe His His Ala Arg Arg Arg Trp Pro Val Leu Gly
    210                 215                 220

Val Ala Leu Gly Ala Leu Leu Val Ala Ala Cys Ser Glu Thr Pro Lys
225                 230                 235                 240

Val Pro Gly Val Pro Pro Ala Asp Glu Glu Val Gly Arg Pro Leu Ser
                245                 250                 255

Ser Val Arg Ser Gly Ala Pro Leu Arg Ser Ala Asp Val Arg Glu Arg
            260                 265                 270

Pro Gln Ala Glu Gln Ala Arg Arg Ala Leu Ser Ala Gly Arg Gly Val
        275                 280                 285

Ala Arg Ser Gly Gly Val Ala Pro Val Ser Ala Thr Ala Ala Glu Leu
    290                 295                 300

Gly Glu Gln Pro Val Ser Leu Asn Phe Val Asp Thr Glu Val Glu Ala
305                 310                 315                 320

Val Val Arg Ala Leu Ser Arg Ala Thr Gly Arg Gln Phe Leu Val Asp
                325                 330                 335

Pro Arg Val Lys Gly Lys Leu Thr Leu Val Ser Glu Gly Gln Val Pro
            340                 345                 350

Ala Arg Thr Ala Tyr Arg Met Leu Thr Ser Ala Leu Arg Met Gln Gly
        355                 360                 365

Phe Ser Val Val Asp Val Asp Gly Val Ser Gln Val Val Pro Glu Ala
    370                 375                 380

Asp Ala Lys Leu Leu Gly Gly Pro Val Tyr Gly Ala Asp Arg Pro Ala
385                 390                 395                 400

Ala Asn Gly Met Val Thr Arg Thr Phe Arg Leu Arg Tyr Glu Asn Ala
                405                 410                 415

Val Asn Leu Ile Pro Val Leu Arg Pro Ile Val Ala Gln Asn Asn Pro
            420                 425                 430

Ile Asn Ala Tyr Pro Gly Asn Asn Thr Val Val Val Thr Asp Tyr Ala
        435                 440                 445

Glu Asn Leu Asp Arg Val Ala Gly Ile Ile Ala Ser Ile Asp Ile Pro
    450                 455                 460

Ser Ala Ser Asp Thr Asp Val Val Pro Ile Gln Asn Gly Ile Ala Val
465                 470                 475                 480

Asp Ile Ala Ser Thr Val Ser Glu Leu Leu Asp Ser Gln Gly Ser Gly
```

```
                485                 490                 495

Gly Ala Glu Gln Gly Gln Lys Thr Val Val Leu Ala Asp Pro Arg Ser
            500                 505                 510

Asn Ser Ile Val Ile Arg Ser Pro Ser Pro Glu Arg Thr Gln Leu Ala
        515                 520                 525

Arg Asp Leu Ile Gly Lys Leu Asp Ser Val Gln Ser Asn Pro Gly Asn
    530                 535                 540

Leu His
545


<210> SEQ ID NO 57
<211> LENGTH: 1030
<212> TYPE: PRT
<213> ORGANISM: Pseudomonas aeruginosa

<400> SEQUENCE: 57

Gly Thr Gly Leu Gly Pro Arg Ser Tyr Ser Ile Ile Glu Gln Gly Met
1               5                   10                  15

Ile Ser Lys Leu Ile Glu Ala Arg Pro Glu Asp Leu Arg Asn Phe Ile
            20                  25                  30

Glu Glu Ala Ala Gly Ile Ser Lys Tyr Lys Glu Arg Arg Arg Glu Thr
        35                  40                  45

Glu Ser Arg Ile Arg Arg Thr Gln Glu Asn Leu Ala Arg Leu Thr Asp
    50                  55                  60

Leu Arg Glu Glu Leu Gly Arg Gln Leu Glu Arg Leu His Arg Gln Ala
65                  70                  75                  80

Gln Ser Ala Glu Lys Tyr Gln Glu His Lys Ala Glu Glu Arg Gln Leu
                85                  90                  95

Lys Ala Gln Leu Gly Ala Val Arg Trp Arg Asp Leu Asn Glu Gln Val
            100                 105                 110

Gly Gln Arg Glu Arg Val Ile Gly Asp Gln Glu Ile Ala Phe Glu Ala
        115                 120                 125

Leu Val Ala Glu Gln Arg Gly Ala Asp Ala Gly Ile Glu Arg Leu Arg
    130                 135                 140

Asp Gly His His Glu Leu Ser Glu Arg Phe Asn Gln Val Gln Ala Arg
145                 150                 155                 160

Phe Tyr Ser Val Gly Gly Asp Ile Ala Arg Val Glu Gln Ser Ile Gln
                165                 170                 175

His Gly Gln Gln Arg Gln Arg Gln Leu Gln Asp Asp Leu Arg Glu Ala
            180                 185                 190

Glu Arg Thr Arg Gln Glu Thr Glu Ser His Leu Gly His Asp Arg Thr
        195                 200                 205

Leu Leu Ala Thr Leu Ala Glu Glu Met Ala Met Leu Ala Pro Glu Gln
    210                 215                 220

Glu Leu Ser Ala Ala Ala Ala Glu Glu Ala Gly Ile Ala Leu Glu Gln
225                 230                 235                 240

Ala Glu Gln Gly Met Gln Ala Trp Gln Gln Gln Trp Asp Ala Phe Asn
                245                 250                 255

Gln Gln Ser Ala Glu Pro Arg Arg Gln Ala Glu Val Gln Gln Ser Arg
            260                 265                 270

Ile Gln His Leu Glu Gln Ser Leu Glu Arg Leu Gln Asp Arg Glu Arg
        275                 280                 285

Arg Leu Gln Glu Glu Arg Gly Gln Leu Ala Ala Asp Pro Glu Asp Ala
    290                 295                 300
```

-continued

```
Ala Ile Leu Glu Leu Asn Glu Gln Val Ala Ile Ala Glu Leu Ala Leu
305                 310                 315                 320

Glu Glu Leu Gln Leu Gln Glu Gln Gly Gln Ala Glu Arg Leu Glu Gln
                325                 330                 335

Leu Arg Gln Glu Leu Gln Gln Leu Ala Ala Glu Gln His Gln Ala Gln
            340                 345                 350

Gly Glu Leu Gln Arg Leu Asn Gly Arg Ile Ala Ser Leu Glu Ala Leu
        355                 360                 365

Gln Gln Ala Ala Leu Asp Pro Gly Gln Gly Ala Leu Glu Trp Leu Arg
    370                 375                 380

Glu Gln Gly Leu Glu Gln Arg Pro Arg Leu Ala Glu Gly Leu Arg Val
385                 390                 395                 400

Glu Pro Gly Trp Glu Leu Ala Val Glu Thr Val Leu Gly Ala Asp Leu
                405                 410                 415

Gln Ala Val Leu Leu Asp Gly Phe Asp Gly Leu Ala Leu Ala Gly Phe
            420                 425                 430

Gly Lys Gly Glu Leu Arg Leu Leu Ser Pro Ala Arg Gly Ala Ala Thr
        435                 440                 445

Ala Ala Gly Ser Leu Leu Asp Lys Val Arg Ala Asp Ala Asp Leu Ser
    450                 455                 460

Pro Trp Leu Ala Arg Val Lys Pro Val Glu Thr Leu Glu Gln Ala Leu
465                 470                 475                 480

Ala Gln Arg Gly Ala Leu Asp Asp Gly Glu Ser Leu Ile Ser Arg Asp
                485                 490                 495

Gly Tyr Trp Val Gly Arg His Phe Leu Arg Val Arg Arg Ser Asp Glu
            500                 505                 510

Ala Gln Gly Gly Met Leu Ala Arg Ala Gln Glu Leu Glu Ala Leu Gln
        515                 520                 525

Glu Arg Arg Glu Ala Leu Glu Thr Arg Val Ala Glu Gly Glu Glu Arg
    530                 535                 540

Leu Ala Ala Ala Arg Asp Glu Gln Arg Glu Leu Glu Gly Ala Arg Glu
545                 550                 555                 560

Gln Val Arg Arg Gln Val Gln Glu Glu Gly Arg Arg His Gly Glu Leu
                565                 570                 575

Lys Ala Gln Leu Ser Ala Gln Gln Ala Lys Val Glu Gln Leu Val Leu
            580                 585                 590

Arg Arg Arg Arg Leu Asp Glu Glu Val Ala Glu Leu Ala Glu Gln Arg
        595                 600                 605

Ala Leu Glu Gln Glu Gln Leu Ser Glu Ala Arg Leu Thr Leu Gln Glu
    610                 615                 620

Ala Leu Asp Ser Met Ala Leu Asp Thr Glu Arg Arg Glu Ser Leu Leu
625                 630                 635                 640

Ala Glu Arg Asp Ala Leu Arg Glu Arg Leu Asp Arg Ile Arg Gln Asp
                645                 650                 655

Ala Arg Thr His Lys Asp His Ala His Gln Leu Ala Val Arg Val Gly
            660                 665                 670

Ser Leu Lys Ala Gln His Asn Ser Thr Gln Gln Ala Leu Glu Arg Leu
        675                 680                 685

Asp Gln Gln Ser Ala Arg Leu Asn Glu Arg Cys Glu Gln Leu Asn Leu
    690                 695                 700

Asn Leu Glu Glu Gly Ala Ala Pro Leu Glu Glu Leu Arg Met Lys Leu
705                 710                 715                 720

Glu Glu Leu Leu Glu Arg Arg Met Ala Val Glu Asp Glu Leu Lys Gln
```

```
                725                 730                 735

Ala Arg Leu Ala Leu Glu Asp Ala Asp Arg Glu Leu Arg Glu Val Glu
            740                 745                 750

Lys Arg Arg Gly Gln Ala Glu Gln Gln Ser Gln Leu Leu Arg Gly Gln
        755                 760                 765

Leu Glu Gln Gln Arg Leu Glu Trp Gln Gly Leu Val Val Arg Arg Lys
    770                 775                 780

Ala Leu Gln Glu Gln Leu Ala Glu Asp Gly Tyr Asp Leu His Thr Val
785                 790                 795                 800

Leu Ala Asn Leu Pro Leu Asp Ala Ser Glu Arg Asp Trp Glu Glu Arg
                805                 810                 815

Leu Glu Ser Leu Ala Ala Arg Ile Gln Arg Leu Gly Pro Ile Asn Leu
            820                 825                 830

Ala Ala Ile Glu Glu Tyr Gln Gln Gln Ser Glu Arg Lys Arg Tyr Leu
        835                 840                 845

Asp Ser Gln Asn Asp Asp Leu Ala Glu Ala Leu Glu Thr Leu Glu Asn
    850                 855                 860

Val Ile Arg Lys Ile Asp Arg Glu Thr Arg Asn Arg Phe Lys Glu Thr
865                 870                 875                 880

Phe Asp Gln Ile Asn Ala Gly Leu Gln Ala Leu Phe Pro Lys Val Phe
                885                 890                 895

Gly Gly Gly Thr Ala Tyr Leu Glu Leu Thr Gly Glu Asp Leu Leu Asp
            900                 905                 910

Thr Gly Val Ala Ile Met Ala Arg Pro Pro Gly Lys Lys Asn Ser Thr
        915                 920                 925

Ile His Leu Leu Ser Gly Gly Glu Lys Ala Leu Thr Ala Leu Ala Leu
    930                 935                 940

Val Phe Ala Ile Phe Gln Leu Asn Pro Ala Pro Phe Cys Met Leu Asp
945                 950                 955                 960

Glu Val Asp Ala Pro Leu Asp Asp Ala Asn Val Gly Arg Tyr Ala Arg
                965                 970                 975

Leu Val Lys Glu Met Ser Glu Lys Val Gln Phe Ile Tyr Ile Thr His
            980                 985                 990

Asn Lys Ile Ala Met Glu Met Ala  Asp Gln Leu Met Gly  Val Thr Met
        995                 1000                1005

His Glu  Pro Gly Cys Ser Arg  Leu Val Ala Val Asp  Val Glu Glu
    1010                1015                1020

Ala Val  Ala Leu Ala Glu Ala
1025                1030


<210> SEQ ID NO 58
<211> LENGTH: 1363
<212> TYPE: PRT
<213> ORGANISM: Pseudomonas aeruginosa

<400> SEQUENCE: 58

Pro Ser Gly Ala Thr Val Val Ser Gly Asp Ala Gly Phe Gln Thr Ser
1               5                   10                  15

Thr Asp Gly Arg His Met Val Ile Asp Gln Gln Ser His Lys Leu Ile
            20                  25                  30

Thr Asn Trp Asn Glu Phe Ser Val Arg Ala Asp Glu Arg Val Ser Phe
        35                  40                  45

His Gln Pro Gly Gln Asp Ala Val Ala Leu Asn Arg Val Ile Gly Arg
    50                  55                  60
```

```
Asn Gly Ser Asp Ile Gln Gly Arg Ile Asp Ala Asn Gly Lys Val Phe
65                  70                  75                  80

Leu Val Asn Pro Asn Gly Val Val Phe Gly Lys Ser Ala Gln Val Asn
                85                  90                  95

Val Gly Gly Leu Val Ala Ser Thr Leu Asp Leu Ala Asp Arg Asp Phe
            100                 105                 110

Leu Ala Gly Asn Tyr Gln Phe Ser Gly Asp Ser Gly Ala Thr Val Ser
        115                 120                 125

Asn Ala Gly Ser Leu Gln Ala Ser Glu Gly Gly Ser Ile Ala Leu Leu
    130                 135                 140

Gly Ala Arg Val Ser Asn Asp Gly Leu Ile Gln Ala Gln Leu Gly Asp
145                 150                 155                 160

Val Ala Leu Gly Ala Gly Gln Gly Ile Asn Leu Asn Phe Asp Gly Asp
                165                 170                 175

Gly Leu Leu Asn Leu Gln Val Asp Lys Gly Ser Val Asp Ala Leu Ala
            180                 185                 190

His Asn Gly Gly Leu Ile Arg Ala Asp Gly Gly Gln Val Leu Met Ser
        195                 200                 205

Ala Arg Ser Ala Asp Ser Leu Leu Lys Thr Val Val Asn Asn Gln Gly
    210                 215                 220

Thr Leu Glu Ala Arg Thr Leu Arg Ser Ala Glu Gly Arg Ile Val Leu
225                 230                 235                 240

Asp Gly Gly Glu Gln Gly Thr Val Arg Val Ala Gly Lys Gln Asp Ala
                245                 250                 255

Ser Ala Ile Gly Gly Gly Asn Gly Gly Leu Val Leu Asn Gln Gly Ala
            260                 265                 270

Asn Val Glu Ile Gln Arg Thr Ala Gln Val Asp Thr His Ala Asp Gln
        275                 280                 285

Gly Ala Thr Gly Thr Trp Arg Ile Leu Ser His Glu Val Ser Val Ala
    290                 295                 300

Ala Val Gly Gln Ala Asn Ala Ala Gly Asp Gly Ser Gly Gln Val His
305                 310                 315                 320

Val Ala Gln Gly Pro Ala Gly Ala Asn Ala Ser Asp Ser Asn Gly Val
                325                 330                 335

Thr Ile Val Gln Gln Gln Pro Ala Val Asp Leu Ala Ala Gly Ala Asn
            340                 345                 350

Gly Thr Ser Ala Val Gln Ser Gln Ser Gly Ala Asn Ile Gly Ser Gly
        355                 360                 365

Ala Asn Gly Ile Ser Val Val Gln Ser Gln Asn Ser Pro Asn Ile Gly
    370                 375                 380

Ser Gly Ala Asn Gly Ile Ser Val Val Gln Ser Gln Asn Gly Ala Asn
385                 390                 395                 400

Ile Gly Ala Gly Ala Ser Gly Ile Ser Val Val Gln Ser Gln Asn Ser
                405                 410                 415

Pro Asn Ile Gly Ser Gly Val Asn Gly Val Thr Val Val Gln Ser Gln
            420                 425                 430

Asn Gly Ala Asn Ile Gly Ser Gly Ala Ser Gly Ile Thr Val Val Gln
        435                 440                 445

Ser Gln Asn Gly Ala Asn Ile Gly Ser Gly Ala Ser Gly Ile Ser Val
    450                 455                 460

Val Gln Ser Gln Ser Gly Pro Ser Ile Gly Ser Gly Val Asn Gly Val
465                 470                 475                 480

Thr Ile Val Gln Ser Gln Ser Gly Ala Asn Ile Gly Pro Gly Val Ser
```

```
                485                 490                 495

Gly Ile Asp Val Val Gln Thr Gln Thr Leu Pro Asn Leu Ser Pro Gly
            500                 505                 510

Ala Asn Gly Ser Ser Ile Val Gln Val Gln Thr Leu Pro Asp Ile Ala
        515                 520                 525

Ala Asp Ala Gly Asn Val His Val Val Gln Val Gln Thr Gly Gly Asn
    530                 535                 540

Lys Val Phe Gly Asn Ser Ala Thr Asn Val Arg Ser Arg Thr Val Gln
545                 550                 555                 560

Ala Arg Ser Asn Glu Asn Val Gly Ser Gly Leu Ala Asn Pro Ser Ser
                565                 570                 575

Ala Gly Lys Gly Ser Thr Leu His Ala Asp Thr Leu Ala Arg Asn Leu
            580                 585                 590

Ser Thr Ser Asn Val Glu Val Val Ala Thr Arg Gly Asn Ala His Val
        595                 600                 605

Gly Ala Pro Leu Ser Trp Asp Ser Gly Asn Gly Leu Thr Leu Thr Ala
    610                 615                 620

Glu Arg Gly Asp Leu Arg Ile Asn Gly Ala Leu Thr Ala Gln Gly Glu
625                 630                 635                 640

Asn Ala Ser Leu Thr Leu Asn Ala Gly Gln Arg Pro Leu Arg Ile Asp
                645                 650                 655

Asp Ser Leu Ser Leu Thr Gly Gln Gly Ala Arg Val Glu Phe Asn Ser
            660                 665                 670

Asp Lys Gly Tyr Ala Leu Ala Glu Gly Thr Arg Ile Thr Leu Ser Gly
        675                 680                 685

Lys Asn Ala Gly Phe Arg Ala Asn Gly Arg Asp Tyr Ser Val Ile Gln
    690                 695                 700

Asp Leu Gln Gln Leu Arg Gly Ile Asp Arg Asp Leu Gly Gly Ser Tyr
705                 710                 715                 720

Val Leu Gly Asn Arg Ile Ala Gly Gly Asn Ser Ser Phe Leu Ser Ile
                725                 730                 735

Gly Asn Ala Ser Ala Phe Gly Gly Thr Phe Asp Gly Leu Gly Asn Thr
            740                 745                 750

Ile Asp Asn Leu Ala Val Tyr Gly Thr Gly Ala Tyr Ser Gly Leu Phe
        755                 760                 765

Ser Val Asn Arg Gly Thr Leu Arg Asn Leu Asn Leu Glu Arg Ile Ser
    770                 775                 780

Ala Asp Gly Ala Gln Ala Thr His Tyr Asn Val Gln Val Gly Ser Leu
785                 790                 795                 800

Ala Ala Val Asn Leu Gly Arg Ile Asp Asn Val Asn Ala Ser Asp Ile
                805                 810                 815

Arg Ile Ala Ala Ala Ser Lys Leu Asn Ser Leu Gly Gly Leu Val Ala
            820                 825                 830

Leu Asn Leu Gly Ser Ile Asp Asn Ala Ser Ala Ser Gly Thr Leu Val
        835                 840                 845

Gly Asn Arg His Thr Tyr Ala Leu Gly Gly Leu Ala Ala Glu Asn Ile
    850                 855                 860

Ser Thr Ala Arg Gly Val Ala Ser Ile Ser Asn Ser Arg Ala Asp Phe
865                 870                 875                 880

Ala Ile Ser Gly Gln Leu Lys Asp His Ala Ser His Tyr Gly Ala Gly
                885                 890                 895

Gly Leu Val Gly Arg Asn Arg Gly Gly Leu Ile Arg Ser Ser Gly Ser
            900                 905                 910
```

```
Gln Gly Thr Leu Ser Leu Ser Gly His Gly Met Asn Leu Gly Gly Leu
      915                 920                 925

Val Gly Tyr Ser Ser Ala Gly Gly Leu Ala Asp Val Ser Ala Ser Val
    930                 935                 940

Asp Val Ser Gly Asn Gly Gln Arg Gly Leu Tyr Gly Gly Leu Ile Gly
945                 950                 955                 960

Leu Asn Val Asn Ser Gly Ile Ala His Ala Thr Ala Ser Gly Lys Val
                965                 970                 975

Arg Gly Thr Asp Ala Glu Ala Leu Gly Gly Leu Ile Gly Arg Asn Leu
            980                 985                 990

Asn Ala Ala Ile Asn Asn Ala Ser  Ala His Gly Asp Val  Ser Leu Gln
      995                 1000                1005

Ala Gly  Arg Tyr Leu Gly Gly  Leu Ile Gly His Asn  Gln Ala Gly
    1010                1015                1020

Asn Leu  Ala Asn Val Ser Thr  Ser Gly Asn Leu Ser  Gly Gly Ser
    1025                1030                1035

Leu Leu  Gln Ala Gly Gly Leu  Ile Gly Leu Asn Ala  Asn Ala Ser
    1040                1045                1050

Leu Val  Asn Ala Ser Ala Lys  Gly Asn Val Ala Thr  Arg Gly Ala
    1055                1060                1065

Glu Ala  Val Gly Gly Leu Leu  Gly Glu Asn Leu Tyr  Gly Ser Val
    1070                1075                1080

Ile Asn  Gly Ser Ala Ser Gly  Glu Val Thr Asp Gly  Ser Gly Lys
    1085                1090                1095

Thr Leu  Gly Gly Leu Ile Gly  Ser Asn Leu Gly Gly  Asn His Ser
    1100                1105                1110

Asn Leu  Lys Ala Ser Gly Trp  Val Asn Ala Gly Ala  Asn Ser Asp
    1115                1120                1125

Val Gly  Gly Leu Ile Gly His  Asn Arg Gly Gly Asn  His Ser Thr
    1130                1135                1140

Leu Ala  Ala Ser Gly Asn Val  Thr Gly Gly Lys Gly  Ser Arg Val
    1145                1150                1155

Gly Gly  Leu Val Gly Tyr Asn  Asp Ala Ala Ser Leu  Thr Asn Val
    1160                1165                1170

Ser Ala  Ser Gly Asn Val Ser  Ala Ser Gly Ser Arg  Ala Ile Gly
    1175                1180                1185

Gly Leu  Ile Gly Ser Asp Leu  Arg Gly Ser Leu Met  Leu Ala Ser
    1190                1195                1200

Ser His  Gly Ile Val Asn Asp  Lys Thr Ser His Asn  Leu Gly Gly
    1205                1210                1215

Leu Val  Gly Arg Gly Glu Asn  Thr Ser Ile Arg Ser  Ala Lys Ala
    1220                1225                1230

Ser Gly  Ala Val Ser Gly Gly  Ala Gly Ile Arg Ala  Gly Gly Leu
    1235                1240                1245

Val Gly  Ser Leu Glu Gly Trp  Gln Ala Leu Ile Leu  Gly Ala Ser
    1250                1255                1260

Ala Gly  Gly Asp Val Thr Ala  Gly Tyr Asp Ser Tyr  Ile Gly Gly
    1265                1270                1275

Leu Val  Gly Phe Ser Thr Ala  Thr Ile Ser Gly Ala  Ser Ala Ser
    1280                1285                1290

Gly Lys  Val Gly Gly Ser Gly  Leu Leu Gly Gly Leu  Val Ala Trp
    1295                1300                1305
```

```
Asn Gln  Gly Asn Val Met Gly  Ser Ser Ala Ser Gly  Arg Leu Glu
    1310                 1315                 1320

Pro Gln  Ile Pro Asn Gln Ile  His Gly Gly Leu Ile  Gly Ile Asn
    1325                 1330                 1335

Phe Gly  Trp Gln Ser Trp Asn  Ser Val Tyr Gly Ala  Ala Ala Thr
    1340                 1345                 1350

Val Pro  Met Ile Gly Arg His  Tyr Asn Leu
    1355                 1360
```

<210> SEQ ID NO 59
<211> LENGTH: 299
<212> TYPE: PRT
<213> ORGANISM: Pseudomonas aeruginosa

<400> SEQUENCE: 59

```
Pro Ser Gly Ala Thr Val Val Ser Gly Asp Ala Gly Phe Gln Thr Ser
1               5                   10                  15

Thr Asp Gly Arg His Met Val Ile Asp Gln Gln Ser His Lys Leu Ile
            20                  25                  30

Thr Asn Trp Asn Glu Phe Ser Val Arg Ala Asp Glu Arg Val Ser Phe
        35                  40                  45

His Gln Pro Gly Gln Asp Ala Val Ala Leu Asn Arg Val Ile Gly Arg
    50                  55                  60

Asn Gly Ser Asp Ile Gln Gly Arg Ile Asp Ala Asn Gly Lys Val Phe
65                  70                  75                  80

Leu Val Asn Pro Asn Gly Val Val Phe Gly Lys Ser Ala Gln Val Asn
                85                  90                  95

Val Gly Gly Leu Val Ala Ser Thr Leu Asp Leu Ala Asp Arg Asp Phe
            100                 105                 110

Leu Ala Gly Asn Tyr Gln Phe Ser Gly Asp Ser Gly Ala Thr Val Ser
        115                 120                 125

Asn Ala Gly Ser Leu Gln Ala Ser Glu Gly Gly Ser Ile Ala Leu Leu
    130                 135                 140

Gly Ala Arg Val Ser Asn Asp Gly Leu Ile Gln Ala Gln Leu Gly Asp
145                 150                 155                 160

Val Ala Leu Gly Ala Gly Gln Gly Ile Asn Leu Asn Phe Asp Gly Asp
                165                 170                 175

Gly Leu Leu Asn Leu Gln Val Asp Lys Gly Ser Val Asp Ala Leu Ala
            180                 185                 190

His Asn Gly Gly Leu Ile Arg Ala Asp Gly Gly Gln Val Leu Met Ser
        195                 200                 205

Ala Arg Ser Ala Asp Ser Leu Leu Lys Thr Val Val Asn Asn Gln Gly
    210                 215                 220

Thr Leu Glu Ala Arg Thr Leu Arg Ser Ala Glu Gly Arg Ile Val Leu
225                 230                 235                 240

Asp Gly Gly Glu Gln Gly Thr Val Arg Val Ala Gly Lys Gln Asp Ala
                245                 250                 255

Ser Ala Ile Gly Gly Gly Asn Gly Gly Leu Val Leu Asn Gln Gly Ala
            260                 265                 270

Asn Val Glu Ile Gln Arg Thr Ala Gln Val Asp Thr His Ala Asp Gln
        275                 280                 285

Gly Ala Thr Gly Thr Trp Arg Ile Leu Ser His
    290                 295
```

<210> SEQ ID NO 60

```
<211> LENGTH: 702
<212> TYPE: PRT
<213> ORGANISM: Artificial sequence
<220> FEATURE:
<223> OTHER INFORMATION: Fusion protein

<400> SEQUENCE: 60

Ser Gly Lys Val Arg Gly Thr Asp Ala Glu Ala Leu Gly Gly Leu Ile
1               5                   10                  15

Gly Arg Asn Leu Asn Ala Ala Ile Asn Asn Ala Ser Ala His Gly Asp
            20                  25                  30

Val Ser Leu Gln Ala Gly Arg Tyr Leu Gly Gly Leu Ile Gly His Asn
        35                  40                  45

Gln Ala Gly Asn Leu Ala Asn Val Ser Thr Ser Gly Asn Leu Ser Gly
    50                  55                  60

Gly Ser Leu Leu Gln Ala Gly Gly Leu Ile Gly Leu Asn Ala Asn Ala
65                  70                  75                  80

Ser Leu Val Asn Ala Ser Ala Lys Gly Asn Val Ala Thr Arg Gly Ala
                85                  90                  95

Glu Ala Val Gly Gly Leu Leu Gly Glu Asn Leu Tyr Gly Ser Val Ile
            100                 105                 110

Asn Gly Ser Ala Ser Gly Glu Val Thr Asp Gly Ser Gly Lys Thr Leu
        115                 120                 125

Gly Gly Leu Ile Gly Ser Asn Leu Gly Gly Asn His Ser Asn Leu Lys
    130                 135                 140

Ala Ser Gly Trp Val Asn Ala Gly Ala Asn Ser Asp Val Gly Gly Leu
145                 150                 155                 160

Ile Gly His Asn Arg Gly Gly Asn His Ser Thr Leu Ala Ala Ser Gly
                165                 170                 175

Asn Val Thr Gly Gly Lys Gly Ser Arg Val Gly Gly Leu Val Gly Tyr
            180                 185                 190

Asn Asp Ala Ala Ser Leu Thr Asn Val Ser Ala Ser Gly Asn Val Ser
        195                 200                 205

Ala Ser Gly Ser Arg Ala Ile Gly Gly Leu Ile Gly Ser Asp Leu Arg
    210                 215                 220

Gly Ser Leu Met Leu Ala Ser Ser His Gly Ile Val Asn Asp Lys Thr
225                 230                 235                 240

Ser His Asn Leu Gly Gly Leu Val Gly Arg Gly Glu Asn Thr Ser Ile
                245                 250                 255

Arg Ser Ala Lys Ala Ser Gly Ala Val Ser Gly Gly Ala Gly Ile Arg
            260                 265                 270

Ala Gly Gly Leu Val Gly Ser Leu Glu Gly Trp Gln Ala Leu Ile Leu
        275                 280                 285

Gly Ala Ser Ala Gly Gly Asp Val Thr Ala Gly Tyr Asp Ser Tyr Ile
    290                 295                 300

Gly Gly Leu Val Gly Phe Ser Thr Ala Thr Ile Ser Gly Ala Ser Ala
305                 310                 315                 320

Ser Gly Lys Val Gly Gly Ser Gly Leu Leu Gly Gly Leu Val Ala Trp
                325                 330                 335

Asn Gln Gly Asn Val Met Gly Ser Ser Ala Ser Gly Arg Leu Glu Pro
            340                 345                 350

Gln Ile Pro Asn Gln Ile His Gly Gly Leu Ile Gly Ile Asn Phe Gly
        355                 360                 365

Trp Gln Ser Trp Asn Ser Val Tyr Gly Ala Ala Ala Thr Val Pro Met
    370                 375                 380
```

```
Ile Gly Arg His Tyr Asn Leu Ala Glu Ala Ala Ala Lys Glu Ala Ala
385                 390                 395                 400

Ala Lys Ala Pro Ser Gly Ala Thr Val Val Ser Gly Asp Ala Gly Phe
                405                 410                 415

Gln Thr Ser Thr Asp Gly Arg His Met Val Ile Asp Gln Gln Ser His
            420                 425                 430

Lys Leu Ile Thr Asn Trp Asn Glu Phe Ser Val Arg Ala Asp Glu Arg
        435                 440                 445

Val Ser Phe His Gln Pro Gly Gln Asp Ala Val Ala Leu Asn Arg Val
    450                 455                 460

Ile Gly Arg Asn Gly Ser Asp Ile Gln Gly Arg Ile Asp Ala Asn Gly
465                 470                 475                 480

Lys Val Phe Leu Val Asn Pro Asn Gly Val Val Phe Gly Lys Ser Ala
                485                 490                 495

Gln Val Asn Val Gly Gly Leu Val Ala Ser Thr Leu Asp Leu Ala Asp
            500                 505                 510

Arg Asp Phe Leu Ala Gly Asn Tyr Gln Phe Ser Gly Asp Ser Gly Ala
        515                 520                 525

Thr Val Ser Asn Ala Gly Ser Leu Gln Ala Ser Glu Gly Gly Ser Ile
    530                 535                 540

Ala Leu Leu Gly Ala Arg Val Ser Asn Asp Gly Leu Ile Gln Ala Gln
545                 550                 555                 560

Leu Gly Asp Val Ala Leu Gly Ala Gly Gln Gly Ile Asn Leu Asn Phe
                565                 570                 575

Asp Gly Asp Gly Leu Leu Asn Leu Gln Val Asp Lys Gly Ser Val Asp
            580                 585                 590

Ala Leu Ala His Asn Gly Gly Leu Ile Arg Ala Asp Gly Gly Gln Val
        595                 600                 605

Leu Met Ser Ala Arg Ser Ala Asp Ser Leu Leu Lys Thr Val Val Asn
    610                 615                 620

Asn Gln Gly Thr Leu Glu Ala Arg Thr Leu Arg Ser Ala Glu Gly Arg
625                 630                 635                 640

Ile Val Leu Asp Gly Gly Glu Gln Gly Thr Val Arg Val Ala Gly Lys
                645                 650                 655

Gln Asp Ala Ser Ala Ile Gly Gly Gly Asn Gly Gly Leu Val Leu Asn
            660                 665                 670

Gln Gly Ala Asn Val Glu Ile Gln Arg Thr Ala Gln Val Asp Thr His
        675                 680                 685

Ala Asp Gln Gly Ala Thr Gly Thr Trp Arg Ile Leu Ser His
    690                 695                 700
```

<210> SEQ ID NO 61
<211> LENGTH: 6
<212> TYPE: PRT
<213> ORGANISM: Artificial sequence
<220> FEATURE:
<223> OTHER INFORMATION: Peptide linker

<400> SEQUENCE: 61

```
Gly Ser Gly Gly Gly Ala
1               5
```

<210> SEQ ID NO 62
<211> LENGTH: 12
<212> TYPE: PRT
<213> ORGANISM: Artificial sequence
<220> FEATURE:
<223> OTHER INFORMATION: Peptide linker

<400> SEQUENCE: 62

Gly Ser Gly Gly Gly Ala Gly Ser Gly Gly Gly Ala
1               5                   10

<210> SEQ ID NO 63
<211> LENGTH: 18
<212> TYPE: PRT
<213> ORGANISM: Artificial sequence
<220> FEATURE:
<223> OTHER INFORMATION: Peptide linker

<400> SEQUENCE: 63

Gly Ser Gly Gly Gly Ala Gly Ser Gly Gly Gly Ala Gly Ser Gly Gly
1               5                   10                  15

Gly Ala

<210> SEQ ID NO 64
<211> LENGTH: 24
<212> TYPE: PRT
<213> ORGANISM: Artificial sequence
<220> FEATURE:
<223> OTHER INFORMATION: Peptide linker

<400> SEQUENCE: 64

Gly Ser Gly Gly Gly Ala Gly Ser Gly Gly Gly Ala Gly Ser Gly Gly
1               5                   10                  15

Gly Ala Gly Ser Gly Gly Gly Ala
            20

<210> SEQ ID NO 65
<211> LENGTH: 10
<212> TYPE: PRT
<213> ORGANISM: Artificial sequence
<220> FEATURE:
<223> OTHER INFORMATION: Peptide linker

<400> SEQUENCE: 65

Gly Glu Asn Leu Tyr Phe Gln Ser Gly Gly
1               5                   10

<210> SEQ ID NO 66
<211> LENGTH: 12
<212> TYPE: PRT
<213> ORGANISM: Artificial sequence
<220> FEATURE:
<223> OTHER INFORMATION: Peptide linker

<400> SEQUENCE: 66

Lys Pro Glu Pro Lys Pro Ala Pro Ala Pro Lys Pro
1               5                   10

<210> SEQ ID NO 67
<211> LENGTH: 8
<212> TYPE: PRT
<213> ORGANISM: Artificial sequence
<220> FEATURE:
<223> OTHER INFORMATION: Peptide linker

<400> SEQUENCE: 67

Ser Ala Cys Tyr Cys Glu Leu Ser
1               5